US007504381B2

(12) United States Patent
Mor et al.

(10) Patent No.: US 7,504,381 B2
(45) Date of Patent: Mar. 17, 2009

(54) ANTIMICROBIAL AGENTS

(75) Inventors: Amram Mor, Haifa (IL); Inna Radzishevsky, Haifa (IL)

(73) Assignee: Technion Research & Development Foundation Ltd., Haifa (IL)

(*) Notice: Subject to any disclaimer, the term of this patent is extended or adjusted under 35 U.S.C. 154(b) by 153 days.

(21) Appl. No.: 11/234,183

(22) Filed: Sep. 26, 2005

(65) Prior Publication Data
US 2006/0074021 A1   Apr. 6, 2006

Related U.S. Application Data

(60) Provisional application No. 60/612,778, filed on Sep. 27, 2004.

(51) Int. Cl.
*A61K 38/08* (2006.01)
*A61K 38/10* (2006.01)
*C07K 7/06* (2006.01)
*C07K 7/08* (2006.01)

(52) U.S. Cl. .................. 514/14; 514/15; 514/16; 530/326; 530/327; 530/329; 530/332

(58) Field of Classification Search ................ None
See application file for complete search history.

(56) References Cited

U.S. PATENT DOCUMENTS

| | | | | |
|---|---|---|---|---|
| 5,965,525 | A * | 10/1999 | Burkhardt et al. | 514/11 |
| 6,127,337 | A * | 10/2000 | Konishi et al. | 514/3 |
| 6,548,048 | B1 * | 4/2003 | Cuthbertson et al. | 424/9.52 |
| 6,566,324 | B2 | 5/2003 | Nadel et al. | |
| 6,571,790 | B1 | 6/2003 | Weinstein | |
| 6,637,430 | B1 | 10/2003 | Voges et al. | |
| 6,652,323 | B2 | 11/2003 | Yanda | |
| 2003/0036628 | A1 * | 2/2003 | Zhelva et al. | 530/327 |
| 2003/0171539 | A1 * | 9/2003 | Quentin et al. | 530/329 |
| 2005/0118678 | A1 * | 6/2005 | Mayo | 435/69.1 |

FOREIGN PATENT DOCUMENTS

| | | | |
|---|---|---|---|
| WO | WO 98/18501 | A2 * | 5/1998 |
| WO | WO 98/25953 | | 6/1998 |
| WO | WO 03/035677 | | 1/2003 |

OTHER PUBLICATIONS

Doyle et al. Synthesis of Potential Anti-HIV GP120 Inhibitors Using A Lysine Template. Journal of Enzyme Inhibition and Medicinal Chemistry. 2002, vol. 17, No. 3, pp. 175-182.*
Stark et al. "Cationic Hydrophobic Peptides With Antimicrobial Activity", Antimicrobial Agents and Chemotherapy, 46(11): 3585-3590, 2002. Abstract, Table 2, p. 3587, p. 3586, Lines 17-22.
Haynie et al. "Antimicrobial Activities of Amphiphilic Peptides Covalently Bonded to A Water-Insoluble Resin", Antimicrobial Agents and Chemotherapy, 39(2): 301-307, 1995. Abstract, Table 1, p. 303.
Tossi et al. "Amphipathic, Alpha-Helical Antimicrobial Peptides", Biopolymers, 55(1): 4-30, 2000. Abstract, Table 1, p. 7-8, Table II, p. 13.
Huang "Peptide-Lipid Interactions and Mechanisms of Antimicrobial Peptides", Novartis Found Symposium, 225: 188-200, 1999. Discussion 200-206.
Epand et al. "Mechanisms for the Modulation of Membrane Bilayer Properties by Amphipathic Helical Peptides", Biopolymers, 37(5): 319-338, 1995. Abstract.
Ono et al. "Design and Synthesis of Basic Peptides Having Amphipathic Beta-Structure and Their Interaction With Phospholipid Membranes", Biochimica et Biophysica Acta (BBA)—Biomembranes, 1022(2): 237-244, 1990. Abstract.
Aarbiou et al. "Human Neutrophil Defensins Induce Lung Epithelial Cell Proliferation In Vitro", Journal of Leukocyte Biology, 72: 167-174, 2002.
Acar "Consequences of Bacterial Resistance to Antibiotics in Medical Practice", Clinical Infectious Diseases, 24(Suppl.1): S17-S18, 1997.
Alan et al. "Expression of A Magainin-Type Antimicrobial Peptide Gene (MSI-99) in Tomato Enhances Resistance to Bacterial Speck Disease", Plant Cell Reports, 22: 388-396, 2004.
National Nosocomial Infections Surveillance "National Nosocomial Infections Surveillance (NNIS) Report, Data Summary From Oct. 1986-Apr. 1996, Isued May 1996. A Report From the National Nosocomial Infections Surveillance (NNIS) System", AJIC, American Journal of Infection Control, 24: 380-388, 1996.
National Nosocomial Infections Surveillance "National Nosocomial Infections Surveillance (NNIS) System Report, Data Summary From Jan. 1990-May 1999, Issued Jun. 1999", AJIC, American Journal of Infection Control, 27: 520-532, 1999.
Ammar et al. "Dermaseptin, A Peptide Antibiotic, Stimulates Microbicidal Activities of Polymorphonuclear Leukocytes", Biochemical and Biophysical Research Communications, 247: 870-875, 1998.
Andreau et al. "Animal Antimicrobial Peptides: An Overview", Biopolymers, 47: 415-433, 1998.
Appendini et al. "Antimicrobial Activity of A 14-Residue Synthetic Peptide Against Foodborne Microorganisms", Journal of Food Protection, 63(7): 889-893, 2000.
Avrahami et al. "Conjugation of a Magainin Analogue With Lipophilic Acids Controls Hydrophobicity, Solution Assembly, and Cell Selectivity", Biochemistry, 41: 2254-2263, 2002.

(Continued)

*Primary Examiner*—Jeffrey E Russel

(57) ABSTRACT

A novel class of antimicrobial polymeric agents, which include a plurality of amino acid residues, such as positively charged amino acid residues, and at least one hydrophobic residue linking there between. such as an omega-amino-fatty acid residue designed to exert antimicrobial activity while being stable, non-toxic and avoiding development of resistance thereto and a process of preparing same are disclosed. Further disclosed are pharmaceutical compositions containing same and a method of treating medical conditions associated with pathological microorganisms, a medical device, an imaging probe and a food preservative utilizing same. Further disclosed are conjugates of an amino acid residue and a hydrophobic moiety residue and a process of preparing same.

6 Claims, 8 Drawing Sheets
(8 of 8 Drawing Sheet(s) Filed in Color)

OTHER PUBLICATIONS

Avrahami et al. "Effect of Multiple Aliphatic Amino Acids Substitutions on the Structure, Function, and Mode of Action of Diastereomeric Membrane Active Peptides", Biochemistry, 40: 12591-12603, 2001.

Baker et al. "Anticancer Efficacy of Magainin2 and Analogue Peptides", Cancer Research, 53: 3052-3057, 1993.

Balaban et al. "A Chimeric Peptide Composed of A Dermaseptin Derivative and An RNA III-Inhibiting Peptide Prevents Graft-Associated Infections by Antibiotic-Resistant Staphylococci", Antimicrobial Agents and Chemotherapy, 48(7): 2544-2550, 2004.

Bassarello et al. "Tolaasins A—E, Five New Lipodepsipeptides Produced by Pseudomonas Tolaasii", Journal of Natural Products, 67: 811-816, 2004.

Belaid et al. "In Vitro Antiviral Activity of Dermaseptins Against Herpes Simplex Virus Type 1", Journal of Medical Virology, 66: 229-234, 2002.

Blazyk et al. "A Novel Linear Amphipathic Beta-Sheet Cationic Antimicrobial Peptide With Enhanced Selectivity for Bacterial Lipids", The Journal of Biological Chemistry, 276(30): 27899-27906, 2001.

Blondelle et al. "Combinatorial Libraries: A Tool to Design Antimicrobial and Antifungal Peptide Analogues Having Lytic Specificities for Structure-Activity Relationship Studies", Biopolymers, 55: 74-87, 2000.

Boman "Antibacterial Peptides: Basic Facts and Emerging Concepts", Journal of Internal Medicine, 254: 197-215, 2003.

Brand et al. "Dermaseptins From Phyllomedusa Oreades and Phyllomedusa Distincta. Anti-Tryponasoma Cruzi Activity Without Cytotoxicity to Mammalian Cells", The Journal of Biological Chemistry, 277(51): 49332-49340, 2002.

Brogden et al. "Antimicrobial Peptides in Animals and Their Role in Host Defences", International Journal of Antimicrobial Agents, 22: 465-478, 2003.

Brul et al. "Preservative Agents in Foods. Mode of Action and Microbial Resistance Mechanisms", International Journal of Food Microbiology, 50: 1-17, 1999.

Chapple et al. "Structure-Function Relationship of Antibacterial Synthetic Peptides Homologous to A Helical Surface Region on Human Lactoferrin Against *Escherichia coli* Serotype O 1 1 1", Infection and Immunity, 66(6): 2434-2440, 1998.

Charpentier et al. "Structure Synthesis, and Molecular Cloning of Dermaseptins B, A Family of Skin Peptide Antibiotics", The Journal of Biological Chemistry, 273(24): 14690-14697, 1998.

Chicharro et al. "N-Terminal Fatty Substitution Increases the Leishmanicidal Activity of CA(1-7)M(2-9), A Cecropin-Melittin Hybrid Peptide", Antimicrobial Agents and Chemotherapy, 45(9): 2441-2449, 2001.

Chu-Kung et al. "Promotion of Peptide Antimicrobial Activity by Fatty Acid Conjugation", Bioconjugate Chemistry, 15: 530-535, 2004.

Cohen "Epidemiology of Drug Resistance: Implications for A Post-Antimicrobial Era", Science, 257, 1050-1055, 1992.

Coote et al. "Inhibitory Action of a Truncated Derivative of the Amphibian Skin Peptide Dermaseptin S3 on *Saccharomyces cerevisiae*", Antimicrobial Agents and Chemotherapy, 42(9): 2160-2170, 1998.

Cosgrove et al. "The Impact of Antimicrobial Resistance on Health and Economic Outcomes", Clinical Infectious Diseases, 36: 1433-1437, 2003.

Dagan et al. "In Vitro Antiplasmodium Effects of Dermaseptin S4 Derivatives", Antimicrobial Agents and Chemotherapy, 46(4): 1059-1066, 2002.

Darveau et al. "Beta-Lactam Antibiotics Potentiate Magainin 2 Antimicrobial Activity In Vitro and In Vivo", Antimicrobial Agents and Chemotherapy, 35(6): 1153-1159, 1991.

De Lucca et al. "Fungicidal and Binding Properties of the Natural Peptides Cecropin B and Dermaseptin", Medical Mycology, 36: 291-298, 1998.

DeGray et al. "Expression of An Antimicrobial Peptide Via the Chloroplast Genome to Control Phytopathogenic Bacteria and Fungi", Plant Physiology, 127: 852-862, 2001.

Devine et al. "Cationic Peptides: Distribution and Mechanisms of Resistance", Current Pharmaceutical Design, 8: 703-714, 2002.

Elsbach et al. "Role of the Bactericidal/Peremeability-Increasing Protein in Host Defence", Current Opinion in Immunology, 10: 45-49, 1998.

Epand "Biophysical Studies of Lipopeptide-Membrane Interactions", Biopolymers, 43: 15-24, 1997.

Epand et al. "Diversity of Antimicrobial Peptides and Their Mechansims of Action", Biochimica et Biophysica Acta, 1462: 11-28, 1999.

Fahrner et al. "Solution Structure of Protegrin-1, A Broad-Spectrum Antimicrobial Peptide From Porcine Leukocytes", Chemistry & Biology, 3: 543-550, 1996.

Fritig et al. "Antimicrobial Proteins in Induced Plant Defense", Current Opinion in Immunology, 10: 16-22, 1998.

Gaidukov et al. "Analysis of Membrane-Binding Properties of Dermaseptin Analogues: Relationships Between Binding and Cytotoxicity", Biochemistry, 42: 12866-12874, 2003.

Gallo et al. "Antimicrobial Peptides: An Emerging Concept in Cutaneous Biology", Journal of Investigative Dermatology, 111: 739-743, 1998.

Gennaro et al. "Pro-Rich Antimicrobial Peptides From Animals: Structure, Biological Functions and Mechanism of Action", Current Pharmaceutical Design, 8: 763-778, 2002.

Ghosh et al. "Selective Cytotoxicity of Dermaseptin S3 Toward Intraerythrocytic Plasmodium Falciparum and the Underlying Molecular Basis", The Journal of Biological Chemistry, 272(50): 31609-31616, 1997.

Giacometti et al. "In-Vitro Activity and Killing Effect of Polycationic Peptides on Methicillin-Resistant Staphyloccus Aureus and Interactions With Clinically Used Antibiotics", Diagnostic Microbiology and Infectious Disease, 38: 115-118, 2000.

Giacometti et al. "Antiendotoxin Acitivity of Antimicrobial Peptides and Glycopeptides", Journal of Chemotherapy, 15(2): 129-133, 2003.

Gough et al. "Antiendotoxin Activity of Cationic Peptide Antimicrobial Agents", Infection and Immunity, 64(12): 4922-4927, 1996.

Gudmundsson et al. "Neutrophil Antibacterial Peptides, Multifunctional Effector Molecules in the Mammalian Immune System", Journal of Immunological Methods, 232: 45-54, 1999.

Hancock "Cationic Peptides: Effectors in Innate Immunity and Novel Antimicrobials", The Lancet Infectious Diseases, 1: 156-164, 2001.

Hancock et al. "Peptide Antibiotics", Antimicrobial Agents and Chemotherapy, 43(6): 1317-1323, 1999.

Hancock et al. "Cationic Peptides: A New Source of Antibiotics", TIBTECH, Trends in Biotechnology, 16: 82-88, 1998.

Hancock et al. "Role of Membranes in the Activities of Antimicrobial Cationic Peptides", FEMS Microbiology Letters, 206: 143-149, 2002.

Hansen "Nisin as A Model Food Preservative", Critical Reviews in Food Sciences and Nutrition, 34(1): 69-93, 1994.

Hernandez et al. "Functional and Structural Damage in Leishmania Mexicana Exposed to the Cationic Peptide Dermaseptin", European Journal of Cell Biology, 59: 414-424, 1992.

Hoffmann et al. "Drosophila Innate Immunity: An Evolutionary Perspective", Nature Immunology, 3(2): 121-126, 2002.

Holmberg et al. "Health and Economic Impacts of Antimicrobial Resistance", Reviews of Infectious Diseases, 9(6): 1065-1078, 1987.

Hong et al. "Structure and Organization of Hemolytic and Nonhemolytic Diastereomers on Antimicrobial Peptides in Membranes", Biochemistry, 38: 16963-16973, 1999.

House of Lords "Resistance to Antibiotics and Other Antimicrobial Agents", The United Kingdom Parliament, Science and Technology—7th Report, HL Paper 81-II, Session 1997-1998.

Hwang et al. "Structure-Function Relationships of Antimicrobial Peptides", Biochemistry and Cell Biology, 76(2/3): 235-246, 1998.

Jacob et al. "Potential Therapeutic Applications of Magainins and Other Antimicrobial Agents of Animal Origin", Ciba Foundation Symposium, 186: 197-223, 1994.

Johnstone et al. "In Vitro Characterization of the Anticancer Activity of Membrane-Active Cationic Peptides. I. Peptide-Mediated Cytotoxicity and Peptide-Enhanced Cytotoxic Activity of Doxorubicin Against Wild-Type and P-Glycoprotein Over-Expressing Tumor Cell Lines" Anti-Cancer Drug Design, 15: 151-160, 2000.

Knight "Non-Oncologic Applications of Radiolabeled Peptides in Nuclear Medicine", The Quarterly Journal of Nuclear Medicine, 47: 279-291, 2003.

Krugliak et al. "Antimalarial Activities of Dermaseptin S4 Derivatives", Antimicrobial Agents and Chemotherapy, 44(9): 2442-2451, 2000.

Kustanovich et al. "Structural Requirements for Potent Versus Selective Cytotoxicity for Antimicrobial Dermaseptin S4 Derivatives", The Journal of Biological Chemistry, 277(19): 16941-16951, 2002.

Kutner et al. "Characterization of Permeation Pathways in the Plasma Membrane of Human Erythrocytes Infected With Early Stages of Plasmodium Falciparum: Association Wtih Parasite Development", Journal of Cellular Physiology, 125: 521-527, 1985.

Lambros et al. "Synchronization of Plasmodium Falciparum Erythocytic Stages in Culture", Journal of Parasitology, 65(3): 418-420, 1979.

Latham "Therapeutic Peptides Revisited", Nature Biotechnology, 17: 755-757, 1999.

Lee et al. "The Protective Effects of Lactoferrin Feeding Against Endotoxin Lethal Shock in Germfree Piglets", Infection and Immunity, 66(4): 1421-1426, 1998.

Lehrer et al. "Antimicrobial Peptides in Mammalian and Insect Host Defense", Current Opinion in Immunology, 11: 23-27, 1999.

Lehrer et al. "Defensins: Antimicrobial and Cytotoxic Peptides of Mammalian Cells", Annual Reviews in Immunology, 11: 105-128, 1993.

Levy "Antimicrobial Proteins and Peptides of Blood: Templates for Novel Antimicrobial Agents", Blood, 96: 2664-2672, 2000.

Lockwood et al. "Acylation of SC4 Dodecapeptide Increases Bactericidal Potency Against Gram-Positive Bacteria, Including Drug-Resistant Strains", Biochemical Journal, 378: 93-103, 2004.

Loury et al. "Effect of Local Application of the Antimicrobial Peptide IB-367 on the Incidence and Severity of Oral Mucositis in Hamsters", Oral Surgery Oral Medicine Oral Pathology Oral Radiology Endod., 87(5): 544-551, 1999.

Lupetti et al. "Radiolabelled Antimicrobial Peptides for Infection Detection", The Lancet Infectious Diseases, 3: 223-229, 2003.

Mak et al. "The Increases Bactericidal Activity of A Fatty Acid-Modified Synthetic Antimicrobial Peptide of Human Cathepsin G Correlates With Its Enhanced Capacity to Interact With Model Membranes", International Journal of Antimicrobial Agents, 21: 13-19, 2003.

Matsuzaki "Why and How are Peptide-Lipid Interactions Utilized for Self-Defense? Magainins and Tachyplesins as Archetypes", Biochimica et Biophysica, 1462: 1-10, 1999.

Merrifield "Solid Phase Peptide Synthesis. I. The Synthesis of A Tetrapeptide", Journal of the American Chemical Society, 85: 2149-2154, 1963.

Moore et al. "Preliminary Experimental Anticancer Activity of Cecropins", Peptide Research, 7(5): 265-269, 1994.

Mor et al. "The NH2-Terminal Alpha-Helical Domain 1-18 of Dermaseptin Is Responsible for Antimicrobial Activity", The Journal of Biological Chemistry, 269(3): 1934-1939, 1994.

Mor et al. "Isolation and Structure of Novel Defensive Peptides From Frog Skin", European Journal of Biochemistry, 219: 145-154, 1994.

Mor et al. "Isolation, Amino Acid Sequence, and Sunthesis of Dermaseptin, A Novel Antimicrobial Peptide of Amphibian Skin", Biochemistry, 30: 8824-8830, 1991.

Mor et al. "Antifungal Activity of Dermaseptin, A novel Vertebrate Skin Peptide", Journal de Mycologique Medicine, 1: 216-220, 1991.

Mor et al., "Structure, Synthesis, and Activity of Dermaseptin B, A Novel Vertebrate Defensive Peptide From Frog Skin: Relationship With Adenoregulin", Biochemistry, 33: 6642-6650, 1994.

Mor "Peptide-Based Antibiotics: A Potential Answer to Raging Antimicrobial Resistance", Drug Development Research, 50: 440-447, 2000.

Mor et al. "The Vertebrate Peptide Antibiotics Dermaseptins Have Overlapping Structural Features But Target Specific Microorganisms", The Journal of Biological Chemistry, 269(50): 31635-31641, 1994.

Mueller et al. "Antimicrobial Peptides as Potential New Antifungals", Mycoses, 42(Suppl.2): 77-82, 1999.

Murphy et al. "Defensins Are Mitogenic for Epithelial Cells and Fibroblasts", Journal of Cellular Physiology, 155: 408-413, 1993.

Nicolas et al. "Peptides as Weapons Against Microorganisms in the Chemical Defense System of Vertebrates", Annual Reviews of Microbiology, 49: 277-304, 1995.

Nissen-Meyer et al. "Ribosomally Synthesized Antimicrobial Peptides: Their Function, Structure, Biogenesis, and Mechanism of Action", Archives in Microbiology, 167:67-77, 1997.

Nizet et al. "Surviving Innate Immunity", Trends in Microbiology, 10(8): 358-359, 2002.

Oh et al. "Role of the Hinge Region and the Tryptophan Residue in the Synthetic Antimicrobial Peptides, Cecropin A(1-8)-Magainin 2(1-12) and Its Analogues, on Their Antibiotic Activities and Structures", Biochemistry, 39: 11855-11864, 2000.

Osusky et al. "Transgenic Plants Expressing Cationic Peptide Chimeras Exhibit Broad-Spectrum Resistance to Phytopathogens", Nature Biotechnology, 18: 1162-1166, 2000.

Osusky et al. "Transgenic Potatoes Expressing A Novel Cationic Peptide Are Resistant to Late Blight and Pink Rot", Transgenic Research, 13: 181-190, 2004.

Pagagianni "Ribosomally Synthesized Peptides With Antimicrobial Properties: Biosynthesis, Structure, Function, and Applications", Biotechnology Advances, 21: 465-499, 2003.

Papo et al. "New Lytic Peptides Based on the D,L-Amphipathic Helix Motif Preferentially Kill Tumor Cells Compared to Normal Cells", Biochemistry, 42: 9346-9354, 2003.

Patrzykat et al. "Sublethal Concentrations of Pleurocidin-Derived Antimicrobial Peptides Inhibit Macromolecular Synthesis in *Escherichia coli*", Antimicrobial Agents and Chemotherapy, 46(3): 605-614, 2002.

Peggion et al. "Trichogin: A Paradigm for Lipopeptaibols", Journal of Peptide Science, 9:679-689, 2003.

Peschel "How Do Bacteria Resist Human Antimicrobial Peptides?", Trends in Microbiology, 10(4): 179-186, 2002.

Piers et al. "The Interaction of A Recombinant Cecropin/Melittin Hybrid Peptide With the Outer Membrane of *Pseudomonas aeruginosa*", Molecular Microbiology, 12(6): 951-958, 1994.

Powell et al. "Design of Self-Processing Antimicrobial Peptides for Plant Protection", Letters in Applied Microbiology, 31: 163-168; 2000.

Sahl et al. "Lantibiotics: Biosynthesis and Biological Activities of Uniquely Modified Peptides From Gram-Positive Bacteria", Annual Reviews in Microbiology, 52: 41-79, 1998.

Salzet "Antimicrobial Peptides Are Signaling Molecules", Trends in Immunology, 23(6): 283-284, 2002.

Scott et al. "An Alpha-Helical Cationic Antimicrobial Peptide Selectively Modulates Macrophage Responses to Lipopolysaccharide and Directly Alters Macrophage Gene Expression", The Journal Immunology, 165: 3358-3365, 2000.

Scott et al. "The Human Antimicrobial Peptide LL-37 Is A Multifunctional Modulator of Innate Immune Responses", The Journal of immunology, 169: 3883-3891, 2002.

Shai "Molecular Recognition Between Membrane-Spanning Polypeptides", TIBS, Trends in Biochemical Science, 20: 460-464, 1995.

Shai "From Innate Immunity to De-Novo Designed Antimicrobial Peptides", Current Pharmaceutical Design, 8: 715-725, 2002.

Shai "Mode of Action of Membrane Active Antimicrobial Peptides", Biopolymers, 66: 236-248, 2002.

Shepherd et al. "Interactions of the Designed Antimicrobial Peptide MB21 and Truncated Dermaseptin S3 With Lipid Bilayers: Molecular-Dynamics Simulations", Biochemical Journal, 370: 233-243, 2003.

Simmaco et al. "Antimicrobial Peptides From Amphibian Skin: What do Tehy Tell Us?", Biopolymers, 47: 435-450, 1998.

Tiozzo et al. "Wide-Spectrum Antibiotic Activity of Synthetic, Amphipathic Peptides", Biochemical and Biophysical Research Communications, 249: 202-206, 1998.

Toniolo et al. "Lipopeptaibols, A Novel Family of Membrane Active, Antimicrobial Peptides", CMLS, Cellular and Molecular Life Sciences, 58: 1179-1188, 2001.

Tossi et al. "Molecular Diversity in Gene-Encoded, Cationic Antimicrobial Polypeptides", Current Pharmaceutical Design, 8: 743-761, 2002.

Vizioli et al. "Antimicrobial Peptides from Animals: Focus on Invertebrates", Trends in Pharmacological Sciences, 23(11): 494-496, 2002.

Wakabayashi et al. "N-Acylated and D Enantiomer Derivatives of A Nonamer Core Peptide of Lactoferricin B Showing Improved Antimicrobial Acitivity", Antimicrobial Ganets and Chemotherapy, 43(5): 1267-1269, 1999.

Wechselberger "Cloning of cDNAs Encoding New Peptides of the Dermaseptin-Family", Biochimica et Biophysica Acta, 1388: 279-283, 1998.

Welling et al. "Technetium-99m Labelled Antimicrobial Peptides Discriminate Between Bacterial Infections and Sterile Inflammations", European Journal of Nuclear Medicine, 27: 292-301, 2000.

Yang et al. "Crystallization of Antimicrobial Pores in Membranes: Magainin and Protegrin", Biophysical Journal, 79: 2002-2009, 2000.

Yeaman et al. "Mechanisms of Antimicrobial Peptide Action and Resistance", Pharmacological Reviews, 55(1): 27-55, 2003.

Zasloff "Antimicrobial Peptides of Multicellular Organisms", Nature, 415: 389-395, 2002.

Zasloff "Innate Immunity, Antimicrobial Peptides, and Protection of the Oral Cavity", The Lancet, 360: 1116-1117, 2002.

Zasloff "Antimicrobial Peptides in Health and Disease", New England Journal of Medicine, 347(15): 1199-1200, 2002.

Zasloff et al. "Antimicrobial Activity of Synthetic Magainin Peptides and Several Analogues", Proc. Natl. Acad. Sci. USA, 85: 910-913, 1988.

Efron et al. "Direct Interaction of Dermaseptin S4 Aminoheptanoyl Derivative With Intraerythrocytic Malaria Parasite Leading to Increased Specific Antiparasitic Activity in Culture", The Journal of Biological Chemistry, 277(27): 24067-24072, 2002. p. 24068, Table 1, 1st Col.

Epand et al. "Direct Comparison of Membrane Interactions of Model Peptides Composed of Only Leu and Lys Residues", Biopolymers (Peptide Science), 71: 2-16, 2003. p. 5, Table 1, p. 6, 2nd Paragraph.

Feder et al. "Structure-Activity Relationship Study of Antimicrobial Dermaseptin S4 Showing the Consequences of Peptide Oligomerization on Selective Cytotoxicity", The Journal of Biological Chemistry, 275(6): 4230-4238, 2000. p. 4232, Table 1, p. 4234, 2nd Col.

Jing et al. "Structure of the Antimicrobial Peptide Ac-RRWWRF-NH2 Bound to Micelles and Its Interactions With Phospholipid Bilayers", Journal of Peptide Research, 61: 219-229, 2003.

Johnson et al. "Engineering Increased Stability in the Antimicrobial Peptide Pediocin PA-1", Applied and Environmental Microbiology, 66(11): 4798-4802, 2000.

Yaron et al. "Activity of Dermaseptin K4-S4 Against Foodborne Pathogens", Peptides, 24: 1815-1821, 2003.

Huang, "Peptide-Lipid Interactions and Mechanisms of Antimicrobial Peptides", Novartis Found Symposium, 225: 188-200, 1999.

\* cited by examiner

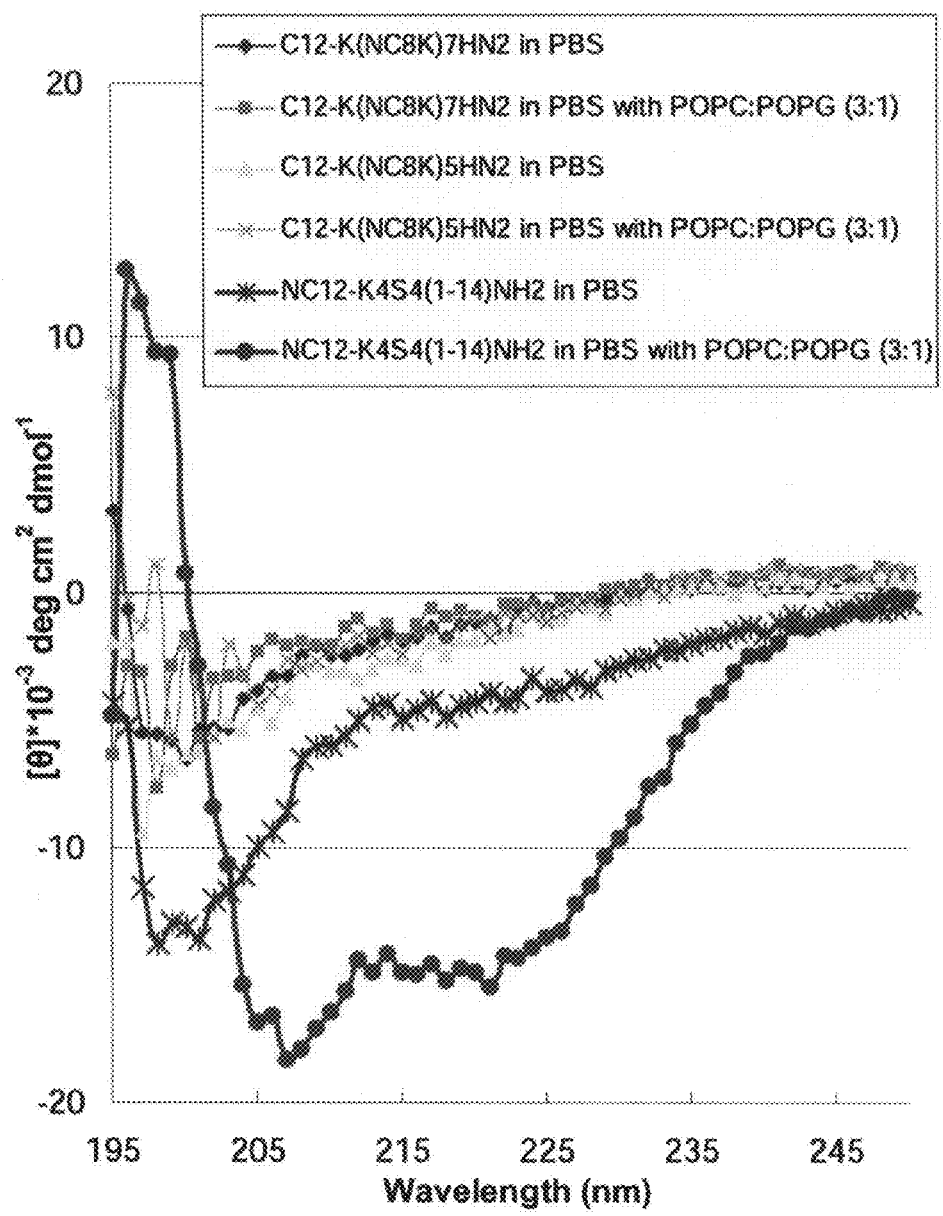

ANTIMICROBIAL AGENTS

RELATED APPLICATIONS

This application claims the benefit of priority from U.S. Provisional Patent Application No. 60/612,778, filed on Sep. 27, 2004, which is incorporated herein by reference in its entirety.

FIELD AND BACKGROUND OF THE INVENTION

The present invention relates to novel antimicrobial agents and, more particularly, to a novel class of polymers which are designed to exert antimicrobial activity while being stable, non-toxic and avoiding development of resistance thereto. The present invention further relates to pharmaceutical compositions, medical devices and food preservatives containing such polymers and to methods of treating medical conditions associated with pathogenic microorganisms utilizing same.

Antibiotics, which are also referred to herein and in the art as antibacterial or antimicrobial agents, are natural substances of relatively small size in molecular terms, which are typically released by bacteria or fungi. These natural substances, as well as derivatives and/or modifications thereof, are used for many years as medications for treating infections caused by bacteria.

As early as 1928, Sir Alexander Fleming observed that colonies of the bacterium *Staphylococcus aureus* could be destroyed by the mold *Penicillium notatum*. His observations lead Fleming to postulate the existence and principle of action of antibiotic substances. It was established that the fungus releases the substance as a mean of inhibiting other organisms in a chemical warfare of microscopic scale. This principle was later utilized for developing medicaments that kill certain types of disease-causing bacteria inside the body. In 1940's Howard Florey and Ernst Chain isolated the active ingredient penicillin and developed a powdery form of the medicine.

These advancements had transformed medical care and dramatically reduced illness and death from infectious diseases. However, over the decades, almost all the prominent infection-causing bacterial strains have developed resistance to antibiotics.

Antibiotic resistance can result in severe adverse outcomes, such as increased mortality, morbidity and medical care costs for patients suffering from common infections, once easily treatable with antibiotics (*Am. J. Infect. Control* 24 (1996), 380-388; *Am. J. Infect. Control* 27 (1999), 520-532; Acar, J. F. (1997), *Clin. Infect. Dis.* 24, Suppl 1, S17-S18; Cohen, M. L. (1992), *Science* 257, 1050-1055; Cosgrove, S. E. and Carmeli, Y. (2003), *Clin. Infect. Dis.* 36, 1433-1437; Holmberg, S. D. et al. (1987), *Rev. Infect. Dis.* 9, 1065-1078) and therefore became one of the most recognized clinical problems of today's governmental, medicinal and pharmaceutical research (U.S. Congress, Office of Technology Assessment, *Impacts of Antibiotic-Resistant Bacteria*, OTA-H-629, Washington, D.C., U.S. Government Printing Office (1995); House of Lords, Science and Technology 7th Report: *Resistance to Antibiotics and Other Antimicrobial Agents*, HL Paper 81-II, session (1997-98); and *Interagency Task Force on Antimicrobial Resistance*, A Public Health Action Plan to Combat Antimicrobial Resistance. Part 1: Domestic issues).

Due to the limitations associated with the use of classical antibiotics, extensive studies have been focused on finding novel, efficient and non-resistance inducing antimicrobial/antibacterial agents.

Within these studies, a novel class of short, naturally occurring peptides, which exert outstanding antimicrobial/antibacterial activity, was uncovered.

These peptides, which are known as antimicrobial peptides (AMPs), are derived from animal sources and constitute a large and diverse family of peptides, which may serve as effective antimicrobial agents against antibiotic-resistant microorganisms (for recent reviews see, for example, Levy, O. (2000) *Blood* 96, 2564-2572; Mor, A. (2000) *Drug Development Research* 50, 440-447; Zasloff, M. (2002) *New England Journal of Medicine* 347, 1199-1200; Zasloff, M. (2002) *Nature* 415, 389-395; Zasloff, M. (2002) *Lancet* 360, 1116-1117). In the past 20 years, over 700 AMPs derived from various sources, from unicellular organisms to mammalians and including humans, have been identified (for recent reviews see, for example, Andreu, D. and Rivas, L. (1998) *Biopolymers* 47, 415-433; Boman, H. G. (2003) *J. Intern. Med.* 254, 197-215; Devine, D. A. and Hancock, R. E. (2002) *Curr. Pharm. Des.* 8, 703-714; Hancock, R. E. and Lehrer, R. (1998) *Trends Biotechnol.* 16, 82-88; Hancock, R. E. (2001) *Lancet Infect. Dis.* 1, 156-164; Hancock, R. E. and Rozek, A. (2002) *FEMS Microbiol. Lett.* 206, 143-149; Hoffmann, J. A. and Reichhart, J. M. (2002) *Nat. Immunol.* 3, 121-126; Lehrer, R. I. and Ganz, T. (1999) *Curr. Opin. Immunol.* 11, 23-27; Nicolas, P. and Mor, A. (1995) *Annu. Rev. Microbiol.* 49, 277-304; Nizet, V. and Gallo, R. L. (2002) *Trends Microbiol.* 10, 358-359; Shai, Y. (2002) *Curr. Pharm. Des.* 8, 715-725; Simmaco, M. et al. (1998) *Biopolymers* 47, 435-450; Tossi, A. et al. (2000) *Biopolymers* 55, 4-30; Tossi, A. and Sandri, L. (2002) *Curr. Pharm. Des.* 8, 743-761; Vizioli, J. and Salzet, M. (2002) *Trends Pharmacol. Sci.* 23, 494-496; Brogden, K. et al. (2003) *Int. J. Antimicrob. Agents* 22, 465-478 and Papagianni, M. (2003) *Biotechnol. Adv.* 21, 465-499).

AMPs are now recognized to have an important role in the innate host defense. They display a large heterogeneity in primary and secondary structures but share common features such as amphiphatic character and net positive charge. These features appear to form the basis for their cytolytic function. Ample data indicate that AMPs cause cells death by destabilizing the ordered structure of the cell membranes, although the detailed mechanism has not been fully understood yet (for recent reviews see, for example, Epand, R. M. et al. (1995), *Biopolymers* 37, 319-338; Epand, R. M. and Vogel, H. J. (1999), *Biochim. Biophys. Acta* 1462, 11-28; Gallo, R. L. and Huttner, K. M. (1998), *J. Invest Dermatol.* 111, 739-743; Gennaro, R. et al. (2002), *Curr. Pharm. Des.* 8, 763-778; Hansen, J. N. (1994), *Crit Rev. Food Sci. Nutr.* 34, 69-93; Huang, H. W. (1999), *Novartis. Found. Symp.* 225, 188-200; Hwang, P. M. and Vogel, H. J. (1998), *Biochem. Cell Biol.* 76, 235-246; Lehrer, R. I. et al. (1993), *Annu. Rev. Immunol.* 11, 105-128; Matsuzaki, K. (1999), *Biochim. Biophys. Acta* 1462, 1-10; Muller, F. M. et al. (1999), *Mycoses* 42 Suppl 2, 77-82; Nissen-Meyer, J. and Nes, I. F. (1997), *Arch. Microbiol.* 167, 67-77; Peschel, A. (2002), *Trends Microbiol.* 10, 179-186; Sahl, H. G. and Bierbaum, G. (1998), *Annu. Rev. Microbiol.* 52, 41-79; Shai, Y. (1995), *Trends Biochem. Sci.* 20, 460-464; and Yeaman, M. R. and Yount, N.Y. (2003), *Pharmacol. Rev.* 55, 27-55). It is assumed that disturbance in membrane structure leads to leakage of small solutes (for example $K^+$, amino acids and ATP) rapidly depleting the proton motive force, starving cells of energy and causing cessation of certain biosynthetic processes (Sahl, H. G. and Bierbaum, G. (1998), *Annu. Rev. Microbiol.* 52, 41-79). This mechanism is consistent with the hypothesis that antimicrobial activity is not mediated by interaction with a chiral center and may thus significantly prevent antibiotic-resistance by circumventing many of the mechanisms known to induce resistance.

In addition to their direct well-documented cytolytic (membrane-disrupting) activity, AMPs also display a variety of interesting biological activities in various antimicrobial fields. Some AMPs were shown to activate microbicidal activity in cells of the innate immunity including leukocytes and monocyte/macrophages (Ammar, B. et al. (1998), *Biochem. Biophys. Res. Commun.* 247, 870-875; Salzet, M. (2002) *Trends Immunol.* 23, 283-284; Scott, M. G. et al. (2000), *J. Immunol.* 165, 3358-3365; and Scott, M. G. et al. (2002), *J. Immunol.* 169, 3883-3891). Many cationic peptides are endowed with lipopolysaccharide binding activity, thus suppress the production of inflammatory cytokines and protect from the cascade of events that leads to endotoxic shock (Chapple, D. S. et al. (1998), *Infect. Immun.* 66, 2434-2440; Elsbach, P. and Weiss, J. (1998), *Curr. Opin. Immunol.* 10, 45-49; Lee, W. J. et al. (1998), *Infect. Immun.* 66, 1421-1426; Giacometti, A. et al. (2003), *J. Chemother.* 15, 129-133; Gough, M. et al. (1996), *Infect. Immun.* 64, 4922-4927; and Hancock, R. E. and Chapple, D. S. (1999), *Antimicrob. Agents Chemother.* 43, 1317-1323). Antimicrobial genes introduced into the genome of plants granted the plant the resistance to pathogens by expressing the peptide (Alan, A. R. et al. (2004), *Plant Cell Rep.* 22, 388-396; DeGray, G. et al. (2001), *Plant Physiol* 127, 852-862; Fritig, B., Heitz, T. and Legrand, M. (1998), *Curr. Opin. Immunol.* 10, 16-22; Osusky, M. et al. (2000), *Nat. Biotechnol.* 18, 1162-1166; Osusky, M. et al. (2004), *Transgenic Res.* 13, 181-190; and Powell, W. A. et al. (2000), *Lett. Appl. Microbiol.* 31, 163-168).

On top of the ribosomally synthesized antimicrobial peptides that have been identified and studied during the last 20 years, thousands of de-novo designed AMPs, were developed (Tossi, A. et al. (2000), *Biopolymers* 55, 4-30). These de-novo designed peptides are comprised of artificially designed sequences and were produced by genetic engineering or by chemical peptide syntheses. The finding that various antimicrobial peptides, having variable lengths and sequences, are all active at similar concentrations, has suggested a general mechanism for the anti-bacterial activity thereof rather than a specific mechanism that requires preferred active structures (Shai, Y. (2002), *Biopolymers* 66, 236-248). Naturally occurring peptides, and de-novo peptides having artificially designed sequences, either synthesized by humans or genetically engineered to be expressed in organisms, exhibit various levels of antibacterial and antifungal activity as well as lytic activity toward mammalian cells. As a result, AMPs are attractive targets for bio-mimicry and peptidomimetic development, as reproduction of critical peptide biophysical characteristics in an unnatural, sequence-specific oligomer should presumably be sufficient to endow antibacterial efficacy, while circumventing the limitations associated with peptide pharmaceuticals (Latham, P. W. (1999), *Nat. Biotechnol.* 17, 755-757).

One of the challenges in designing new antimicrobial peptides relies on developing peptidomimetics that would have high specificity toward bacterial or fungal cells, and consequently, would allow better understanding of the mechanism underlying the peptide lytic specificity, i.e., discrimination between cell membranes. Structure-activity relationships (SAR) studies on AMPs typically involve the systematic modification of naturally occurring molecules or the de-novo design of model peptidomimetics predicted to form amphiphatic alpha-helices or beta-sheets, and the determination of structure and activity via various approaches (Tossi, A. et al. (2000), *Biopolymers* 55, 4-30), as follows:

Minimalist methods for designing de-novo peptides are based on the requirement for an amphiphatic, alpha-helical or beta-sheet structure. The types of residues used are generally limited to the basic, positively charged amino acids lysine or arginine, and one to three of the hydrophobic residues alanine, leucine, isoleucine, glycine, valine, phenylalanine, or tryptophan (Blazyk, J. et al. (2001), *J. Biol. Chem.* 276, 27899-27906; Epand, R. F. et al. (2003), *Biopolymers* 71, 2-16; Hong, J. et al. (1999), *Biochemistry* 38, 16963-16973; Jing, W. et al. (2003), *J. Pept. Res.* 61, 219-229; Ono, S. et al. (1990), *Biochim. Biophys. Acta* 1022, 237-244; and Stark, M. et al. (2002), *Antimicrob. Agents Chemother.* 46, 3585-3590). While these approaches may lead to the design of potent antimicrobial agents, subtleties to the sequence of AMPs that may have been selected for by evolution are not considered and their absence may lead to a loss of specificity.

Sequence template methods for designing and synthesizing amphiphatic AMPs typically consists of extracting sequence patterns after comparison of a large series of natural counterparts. The advantage of this method, as compared with conventional sequence modification methods, is that it reduces the number of peptides that need to be synthesized in order to obtain useful results, while maintaining at least some of the sequence based information. As discussed hereinabove, the latter is lost in minimalist approaches (Tiozzo, E. et al. (1998), *Biochem. Biophys. Res. Commun.* 249, 202-206).

Sequence modification method includes all of the known and acceptable methods for modifying natural peptides, e.g., by removing, adding, or replacing one or more residues, truncating peptides at the N- or C-termini, or assembling chimeric peptides from segments of different natural peptides. These modifications have been extensively applied in the study of dermaseptins, cecropins, magainins, and melittins in particular (Scott, M. G. et al. (2000), *J. Immunol.* 165, 3358-3365; Balaban, N. et al. (2004), *Antimicrob. Agents Chemother.* 48, 2544-2550; Coote, P. J. et al. (1998), *Antimicrob. Agents Chemother.* 42, 2160-2170; Feder, R. et al. (2000), *J. Biol. Chem.* 275, 4230-4238; Gaidukov, L. et al. (2003), *Biochemistry* 42, 12866-12874; Kustanovich, I. et al. (2002), *J. Biol. Chem.* 277, 16941-16951; Mor, A. and Nicolas, P. (1994) *J. Biol. Chem.* 269, 1934-1939; Mor, A. et al. (1994), *J. Biol. Chem.* 269, 31635-31641; Oh, D. et al. (2000), *Biochemistry* 39, 11855-11864; Patrzykat, A. et al. (2002), *Antimicrob. Agents Chemother.* 46, 605-614; Piers, K. L. and Hancock, R. E. (1994) *Mol. Microbiol.* 12, 951-958; and Shepherd, C. M. et al. (2003), *Biochemistry* 370, 233-243).

The approaches described above have been applied in many studies aiming at designing novel AMPs. In these studies, the use of alpha-helix and/or beta-sheet inducing building blocks, the use of the more flexible beta-amino acid building blocks, the use of mixed D- and L-amino acid sequences and the use of facially amphiphilic arylamide polymers, have all demonstrated the importance of induced amphiphatic conformations on the biological activity of AMPs.

Antimicrobial peptides can act in synergy with classical antibiotics, probably by enabling access of antibiotics into the bacterial cell (Darveau, R. P. et al. (1991), *Antimicrob. Agents Chemother.* 35, 1153-1159; and Giacometti, A. et al. (2000), *Diagn. Microbiol. Infect. Dis.* 38, 115-118). Other potential uses include food preservation (Brul, S. and Coote, P. (1999), *Int. J. Food Microbiol.* 50, 1-17; Yaron, S., Rydlo, T. et al. (2003), *Peptides* 24, 1815-1821; Appendini, P. and Hotchkiss, J. H. (2000), *J. Food Prot.* 63, 889-893; and Johnsen, L. et al. (2000), *Appl. Environ. Microbiol.* 66, 4798-4802), imaging probes for detection of bacterial or fungal infection loci (Welling, M. M. et al. (2000), *Eur. J. Nucl. Med.* 27, 292-301; Knight, L. C. (2003), *Q. J. Nucl. Med.* 47, 279-291; and Lupetti, A. et al. (2003), *Lancet Infect. Dis.* 3, 223-229), antitumor activity (Baker, M. A. et al. (1993), *Cancer Res.* 53, 3052-3057; Jacob, L. and Zasloff, M. (1994), *Ciba Found. Symp.* 186, 197-216; Johnstone, S. A. et al. (2000), *Anticancer Drug Des* 15, 151-160; Moore, A. J. et al. (1994), *Pept. Res.* 7, 265-269; and Papo, N. and Shai, Y. (2003), *Biochemistry* 42, 9346-9354), mitogenic activity (Aarbiou, J. et al. (2002), *J. Leukoc. Biol.* 72, 167-174; Murphy, C. J. et al. (1993), *J. Cell Physiol* 155, 408-413; and Gudmundsson, G. H. and Agerberth, B. (1999), *J. Immunol. Methods* 232, 45-54) and lining of medical/surgical devices (Haynie, S. L. et al. (1995), *Antimicrob. Agents Chemother.* 39, 301-307).

However, while the potential of AMPs as new therapeutic agents is well recognized, the use of the presently known AMPs is limited by lack of adequate specificity, and optional systemic toxicity (House of Lords, *Science and Technology 7th Report*: Resistance to antibiotics and other antimicrobial agents. HL Paper 81-II, session, 1997-98; and Alan, A. R. et al. (2004), *Plant Cell Rep.* 22, 388-396). Thus, there is a clear need for developing new antimicrobial peptides with improved specificity and toxicity profile.

Moreover, although peptides are recognized as promising therapeutic and antimicrobial agents, their use is severely limited by their in vivo and ex vivo instability and by poor pharmacokinetics. Peptides and polypeptides are easily degraded in oxidative and acidic environments and therefore typically require intravenous administration (so as to avoid, e.g., degradation in the gastrointestinal tract). Peptides are further broken down in the blood system by proteolytic enzymes and are rapidly cleared from the circulation. Moreover, peptides are typically characterized by poor absorption after oral ingestion, in particular due to their relatively high molecular mass and/or the lack of specific transport systems. Furthermore, peptides are characterized by high solubility and therefore fail to cross biological barriers such as cell membranes and the blood brain barrier, but exhibit rapid excretion through the liver and kidneys. The therapeutic effect of peptides is further limited by the high flexibility thereof, which counteracts their receptor-affinity due to the steep entropy decrease upon binding and a considerable thermodynamic energy cost. In addition, peptides are heat and humidity sensitive and therefore their maintenance requires costly care, complex and inconvenient modes of administration, and high-cost of production and maintenance. The above disadvantages impede the use of peptides and polypeptides as efficient drugs and stimulate the quest for an alternative, which oftentimes involves peptidomimetic compounds.

Peptidomimetic compounds are modified polypeptides which are designed to have a superior stability, both in vivo and ex vivo, and yet at least the same receptor affinity, as compared with their parent peptides. In order to design efficacious peptidomimetics, an utmost detailed three-dimensional understanding of the interaction with the intended target is therefore required.

One method attempting at achieving the above goal utilizes synthetic combinatorial libraries (SCLs), a known powerful tool for rapidly obtaining optimized classes of active compounds. Thus, a number of novel antimicrobial compounds ranging from short peptides to small heterocyclic molecules have been identified from SCLs (Blondelle, S. E. and Lohner, K. (2000), *Biopolymers* 55, 74-87).

Several families of naturally occurring modified peptides which exhibit strong antimicrobial activity, have been uncovered in many organisms. These compounds, and their effective chemical alterations, have proposed a lead towards a general solution to the challenge of creating an antimicrobial compound devoid of the disadvantages associated with natural AMPs.

Thus, for example, naturally occurring short antimicrobial peptides characterized by a lipophilic acyl chain at the N-terminus were uncovered in various microorganisms (Bassarello, C. et al. (2004), *J. Nat. Prod.* 67, 811-816; Peggion, C., et al. (2003), *J. Pept. Sci.* 9, 679-689; and Toniolo, C. et al. (2001), *Cell Mol. Life Sci.* 58, 1179-1188). Acylation of AMPs was hence largely used as a technique to endow AMPs with improved antimicrobial characteristics (Avrahami, D. et al. (2001), *Biochemistry* 40, 12591-12603; Avrahami, D. and Shai, Y. (2002), *Biochemistry* 41, 2254-2263; Chicharro, C. et al. (2001), *Antimicrob. Agents Chemother.* 45, 2441-2449; Chu-Kung, A. F. et al. (2004), *Bioconjug. Chem.* 15, 530-535; Efron, L. et al. (2002), *J. Biol. Chem.* 277, 24067-24072; Lockwood, N. A. et al. (2004), *Biochem. J.* 378, 93-103; Mak, P. et al. (2003), *Int. J. Antimicrob. Agents* 21, 13-19; and Wakabayashi, H. et al. (1999), Antimicrob. Agents Chemother. 43, 1267-1269). However, some studies indicate that attaching a hydrocarbon chain to the peptide, results in only marginal increase in the affinity of the lipopeptide to the membrane (Epand, R. M. (1997), *Biopolymers* 43, 15-24).

One family of AMPs capable of alluding towards the main goal is the family of dermaseptins. Dermaseptins are peptides isolated from the skin of various tree frogs of the *Phyllomedusa* species (Brand, G. D. et al. (2002), *J. Biol. Chem.* 277, 49332-49340; Charpentier, S. et al. (1998), *J. Biol. Chem.* 273, 14690-14697; Mor, A. et al. (1991), *Biochemistry* 30, 8824-8830; Mor, A. et al. (1994), *Biochemistry* 33, 6642-6650; Mor, A. and Nicolas, P. (1994), *Eur. J. Biochem.* 219, 145-154; and Wechselberger, C. (1998), *Biochim. Biophys. Acta* 1388, 279-283). These are structurally and functionally related cationic peptides, typically having 24-34 amino acid residues. Dermaseptins were found to exert rapid cytolytic activity, from seconds to minutes, in vitro, against a variety of microorganisms including viruses, bacteria, protozoa, yeast and filamentous fungi (Coote, P. J. et al. (1998), *Antimicrob. Agents Chemother.* 42, 2160-2170; Mor, A. and Nicolas, P. (1994), *J. Biol. Chem.* 269, 1934-1939; Mor, A. et al. (1994), *J. Biol. Chem.* 269, 31635-31641; Mor, A. and Nicolas, P. (1994), *Eur. J. Biochem.* 219, 145-154; Belaid, A. et al. (2002), *J. Med. Virol.* 66, 229-234; De Lucca, A. J. et al. (1998), *Med. Mycol.* 36, 291-298; Hernandez, C. et al. (1992), *Eur. J. Cell Biol.* 59, 414-424; and Mor, A. et al. (1991), *J. Mycol. Med* 1, 5-10) as well as relatively inaccessible pathogens such as intracellular parasites (Efron, L. et al. (2002), *J. Biol. Chem.* 277, 24067-24072; Dagan, A. et al. (2002), *Antimicrob. Agents Chemother.* 46, 1059-1066; Ghosh, J. K. et al. (1997), *J. Biol. Chem.* 272, 31609-31616; and Krugliak, M. et al. (2000), *Antimicrob. Agents Chemother.* 44, 2442-2451).

Since dermaseptins portray the biodiversity existing in a very large group of antimicrobial peptides in terms of structural and biological properties, they serve as a general model system for understanding the function(s) of cationic antimicrobial peptides.

The 28-residue peptide dermaseptin S4 is known to bind avidly to biological membranes and to exert rapid cytolytic activity against a variety of pathogens as well as against erythrocytes (Mor, A. et al. (1994), *J. Biol. Chem.* 269(50): 31635-41).

In a search for an active derivative (peptidomimetic) of S4, a 28-residue derivative in which the amino acid residues at the fourth and twentieth positions were replaced by lysine residues, known as $K_4K_{20}$-S4, and two short derivatives of 16 and 13 residues in which the amino acid residue at the fourth position was replaced by a lysine residue, known as $K_4$-S4 (1-16) and $K_4$-S4(1-13), respectively, were prepared and tested for the inhibitory effect thereof (Feder, R. et al. (2000), *J. Biol. Chem.* 275, 4230-4238). The minimal inhibitory concentrations (MICs) of these derivatives for 90% of the 66 clinical isolates tested (i.e., $MIC_{90}$ for *S. aureus, P. aeruginosa* and *E. coli*), varied between 2 and 8 µg/ml for the various species, whereby the 13-mer derivative $K_4$-S4(1-13) was found to be significantly less hemolytic when incubated with human erythrocytes, as compared with similarly active derivatives of magainin and protegrin, two confirmed antimicrobial peptide families (Fahrner, R. L. et al. (1996), *Chem. Biol.* 3(7): 543-50; Zasloff, M. et al. (1988), *Proc. Natl. Acad. Sci. USA* 85(3): 910-3; Yang L. et al. (2000), *Biophys. J*, 79 2002-2009). Additional studies further confirmed that short, lysine-enriched S4 derivatives, are promising anti-microbial agents by being characterized by reduced toxicity and by showing efficacy also after pre-exposure of the subjects thereto.

N-terminal acylation of the C-terminally truncated 13-mer S4 derivative $K_4$-S4(1-13) also resulted in reduced hemolytic activity, whereby several derivatives, such as its aminoheptanoyl derivative, displayed potent and selective activity against the intracellular parasite, i.e., increased antiparasitic efficiency and reduced hemolysis. These studies indicate that increasing the hydrophobicity of anti-microbial peptides enhance their specificity, presumably by allowing such AMPs to act specifically on the membrane of intracellular parasites and thus support a proposed mechanism according to which the lipopeptide crosses the host cell plasma membrane and selectively disrupts the parasite membrane(s).

Overall, the data collected from in-vitro and in-vivo experiments indicated that some dermaseptin derivatives could be useful in the treatment of a variety of microbial-associated conditions including infections caused by multidrug-resistant pathogens. These agents were found highly efficacious, and no resistance was appeared to develop upon their administration. Nevertheless, the therapeutic use of these agents is still limited by the in vivo and ex vivo instability thereof, by poor pharmacokinetics, and by other disadvantageous characteristics of peptides, as discussed hereinabove.

In conclusion, most of the presently known antimicrobial peptides and peptidomimetics are of limited utility as therapeutic agents despite their promising antimicrobial activity. The need for compounds which have AMP characteristics, and are devoid of the limitations associated with AMPs is still present, and the concept of providing chemically and metabolically-stable active compounds in order to achieve enhanced specificity and hence enhanced clinical selectivity has been widely recognized.

There is thus a widely recognized need for, and it would be highly advantageous to have, novel, metabolically-stable, non-toxic and cost-effective antimicrobial agents devoid of the above limitations.

SUMMARY OF THE INVENTION

The present inventors have now designed and successfully prepared a novel class of polymeric compounds, which are based on positively charged amino acid residues and hydrophobic moieties. These novel polymers were found highly efficient as selective antimicrobial agents, while being devoid of toxicity and resistance induction.

Thus, according to one aspect of the present invention there is provided a polymer which includes two or more amino acid residues and one or more hydrophobic moiety residues, wherein one or more of the hydrophobic moiety residues is being covalently linked to at least two amino acid residues via the N-alpha of one amino acid residue and via the C-alpha of another amino acid residue.

According to further features in preferred embodiments of the invention described below, the polymer is having an antimicrobial activity.

According to still further features in the described preferred embodiments the polymer is capable of selectively destructing at least a portion of the cells of a pathogenic microorganism.

According to still further features in the described preferred embodiments the pathogenic microorganism is selected from the group consisting of a prokaryotic organism, an eubacterium, an archaebacterium, a eukaryotic organism, a yeast, a fungus, an alga, a protozon and a parasite.

According to still further features in the described preferred embodiments the polymer includes at least two hydrophobic moiety residues, wherein one or more of the hydrophobic moiety residues is linked to the N-alpha of an amino acid residue at the N-terminus of one of the amino acid residues and/or the C-alpha of another amino acid residue at the C-terminus.

According to still further features in the described preferred embodiments the polymer includes two or more hydrophobic moiety residues, wherein one or more of the hydrophobic moiety residues is linked to the side-chain of an amino acid residue in the polymer.

According to still further features in the described preferred embodiments one or more of the amino acid residues is a positively charged amino acid residue.

According to still further features in the described preferred embodiments the positively charged amino acid residue is selected from the group consisting of a histidine residue, a lysine residue, an ornithine residue and an arginine residue.

According to yet further features of the present invention, one or more of the hydrophobic moiety residues is linked to one or more of the amino acid residues via a peptide bond.

According to still further features in the described preferred embodiments one or more of the hydrophobic moiety residues is linked to two amino acid residues via a peptide bond According to still further features in the described preferred embodiments one or more of the hydrophobic moiety residues is linked to each of the amino acid residues via a peptide bond.

According to still further features in the described preferred embodiments one or more of the hydrophobic moiety residues is linked to the N-alpha of the amino acid residue via a peptide bond.

According to still further features in the described preferred embodiments one or more of the hydrophobic moiety residues is linked to the C-alpha of the amino acid residue via a peptide bond.

According to still further features in the described preferred embodiments one or more of the hydrophobic moieties has a carboxylic group at one end thereof and an amine group at the other end thereof.

According to still further features in the described preferred embodiments the polymer includes from 2 to 50 amino acid residues, preferably from 2 to 12 amino acid residues and more preferably from 2 to 8 amino acid residues.

According to still further features in the described preferred embodiments the polymer includes from 1 to 50 hydrophobic moiety residues, preferably from 1 to 12 hydrophobic moiety residues and more preferably from 1 to 8 hydrophobic moiety residues.

According to still further features in the described preferred embodiments the hydrophobic moiety residue includes one or more hydrocarbon chains which has from 4 to 30 carbon atoms.

According to still further features in the described preferred embodiments the hydrophobic moiety residue includes one or more fatty acid residues which are selected from the group consisting of an unbranched saturated fatty acid residue, a branched saturated fatty acid residue, an unbranched unsaturated fatty acid residue, a branched unsaturated fatty acid residue and any combination thereof, and the fatty acid residue has from 4 to 30 carbon atoms.

According to still further features in the described preferred embodiments the fatty acid residue is selected from the group consisting of a butyric acid residue, a caprylic acid residue and a lauric acid residue.

According to still further features in the described preferred embodiments one or more of the hydrophobic moieties is an ω-amino-fatty acid residue. The ω-amino-fatty acid residue is selected from the group consisting of 4-aminobutyric acid, 6-amino-caproic acid, 8-amino-caprylic acid, 10-amino-capric acid, 12-amino-lauric acid, 14-amino-myristic acid, 16-amino-palmitic acid, 18-amino-stearic acid, 18-amino-oleic acid, 16-amino-palmitoleic acid, 18-amino-linoleic acid, 18-amino-linolenic acid and 20-amino-arachidonic acid. Preferably, the ω-amino-fatty acid residue is selected from the group consisting of 4-amino-butyric acid, 8-amino-caprylic acid and 12-amino-lauric acid.

According to still further features in the described preferred embodiments all of the amino acid residues of the polymer are positively charged amino acid residues, such as lysine residues, histidine residues, ornithine residues, arginine residues and any combinations thereof.

According to still further features of the preferred embodiments of the invention described below, the polymer further includes one or more active agent attached thereto.

According to still further features in the described preferred embodiments the active agent is attached to a side chain of an amino acid residue, either via the N-alpha of the amino acid residue at the N-terminus and/or the C-alpha of the amino acid residue at the C-terminus, and/or to one or more of the hydrophobic moiety residues of the polymer.

According to still further features in the described preferred embodiments the active agent is a labeling agent, which is selected from the group consisting of a fluorescent agent, a radioactive agent, a magnetic agent, a chromophore, a phosphorescent agent and a heavy metal cluster.

According to still further features in the described preferred embodiments the active agent comprises at least one therapeutically active agent, which is selected from the group consisting of an agonist residue, an amino acid residue, an analgesic residue, an antagonist residue, an antibiotic agent residue, an antibody residue, an antidepressant agent, an antigen residue, an anti-histamine residue, an anti-hypertensive agent, an anti-inflammatory drug residue, an anti-metabolic agent residue, an antimicrobial agent residue, an antioxidant residue, an anti-proliferative drug residue, an antisense residue, a chemotherapeutic drug residue, a co-factor residue, a cytokine residue, a drug residue, an enzyme residue, a growth factor residue, a heparin residue, a hormone residue, an immunoglobulin residue, an inhibitor residue, a ligand residue, a nucleic acid residue, an oligonucleotide residue, a peptide residue, a phospholipid residue, a prostaglandin residue, a protein residue, a toxin residue, a vitamin residue and any combination thereof.

According to still further features in the described preferred embodiments the polymer is capable of delivering one or more active agents, such as a labeling agent or a therapeutically active agent, to at least a portion of the cells of a pathogenic microorganism as described herein.

According to still further features in the described preferred embodiments the polymer described herein can be represented by the general formula I:

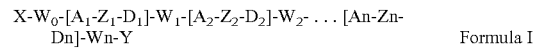

$$X\text{-}W_0\text{-}[A_1\text{-}Z_1\text{-}D_1]\text{-}W_1\text{-}[A_2\text{-}Z_2\text{-}D_2]\text{-}W_2\text{-} \ldots [A_n\text{-}Z_n\text{-}D_n]\text{-}W_n\text{-}Y$$

Formula I wherein:

n is an integer from 2 to 50, preferably from 2 to 12 and more preferably from 2 to 8;

$A_1, A_2, \ldots, A_n$ are each independently an amino acid residue, preferably a positively charged amino acid residue, and more preferably all of $A_1, A_2, \ldots, A_n$ are positively charged amino acid residues as discussed hereinabove, such as histidine residues, lysine residues, ornithine residues and arginine residues;

$D_1, D_2, \ldots, D_n$ are each independently a hydrophobic moiety residue, as described herein, or absent, provided that at least one such hydrophobic moiety residue exists in the polymer, and preferably at least one of the hydrophobic moiety residues is a ω-amino-fatty acid residue;

$Z_1, Z_2, \ldots, Z_n$ and $W_0, W_1, W_2, \ldots, W_n$ are each independently a linking moiety linking an amino acid residue and a hydrophobic moiety residue or absent, preferably at least one of the linking moieties is a peptide bond and most preferable all the linking moieties are peptide bonds; and X and Y may each independently be hydrogen, an amino acid residue, a hydrophobic moiety residue or another polymer having the general Formula I.

According to still further features in the described preferred embodiments the polymer further includes one or more active agent, as described herein, attached to one or more of either X, Y, $W_0$, $A_1$, An and/or Wn.

According to another aspect of the present invention there is provided a conjugate which includes an amino acid residue and a hydrophobic moiety residue attached to the N-alpha or the C-alpha of the amino acid residue, the hydrophobic moiety residue being designed capable of forming a bond with an N-alpha or a C-alpha of an additional amino acid residue.

According to further features in the preferred embodiments of the invention described below, the hydrophobic moiety residue is attached to the N-alpha or the C-alpha of the amino acid residue via a peptide bond.

According to still further features in the described preferred embodiments the hydrophobic moiety has a carboxylic group at one end thereof and an amine group at the other end thereof and further includes a hydrocarbon chain as described herein.

According to still further features in the described preferred embodiments the hydrophobic moiety includes a fatty acid residue as described herein.

According to still further features in the described preferred embodiments the hydrophobic moiety is an ω-amino-fatty acid residue as described herein.

According to still another aspect of the present invention there is provided a process of preparing the conjugate described hereinabove, the process comprises providing an amino acid; providing a hydrophobic moiety having a first functional group that is capable of reacting with an N-alpha of an amino acid residue and/or a second functional group capable of reacting with a C-alpha of an amino acid; linking the first functional group in the hydrophobic moiety to the amino acid via the N-alpha of said amino acid; or linking the second functional group in the hydrophobic moiety to the amino acid via the C-alpha of the amino acid. Preferably the hydrophobic moiety is linked to the amino acid via a peptide bond.

According to further features in the preferred embodiments if the invention described below, the amino acid is a positively charged amino such as, for example, histidine, lysine, ornithine and arginine.

According to still further features in the described preferred embodiments the hydrophobic moiety has a carboxylic group at one end thereof, an amine group at the other end thereof and a hydrocarbon chain, as described herein.

According to still further features in the described preferred embodiments the hydrophobic moiety includes a fatty acid residue as described herein.

According to still further features in the described preferred embodiments the hydrophobic moiety is an ω-aminofatty acid residue as described herein.

According to yet another aspect of the present invention there is provided a pharmaceutical composition which includes as an active ingredient the polymer of the present invention, described herein, and a pharmaceutically acceptable carrier.

According to further features in the preferred embodiments of the invention described below, the pharmaceutical composition is packaged in a packaging material and identified in print, in or on said packaging material, for use in the treatment of a medical condition associated with a pathogenic microorganism such as a prokaryotic organism, an eubacterium, an archaebacterium, a eukaryotic organism, a yeast, a fungus, an alga, a protozon and a parasite.

According to still further features in the described preferred embodiments the pharmaceutical composition further includes one or more additional therapeutically active agent as described herein, whereby preferably the therapeutically active agent includes an antibiotic agent.

According to another aspect of the present invention there is provided a method of treating a medical condition associated with a pathogenic microorganism, as described herein, the method includes administering to a subject in need thereof a therapeutically effective amount of the polymer described herein.

According to further features in the preferred embodiments of the invention described below, the administration is effected orally, rectally, intravenously, topically, intranasally, intradermally, transdermally, subcutaneously, intramuscularly, intrperitoneally or by intrathecal catheter.

According to still further features in the described preferred embodiments the method further includes administering to the subject one or more therapeutically active agent as described herein, preferably, an antibiotic agent.

According to still further features in the described preferred embodiments the polymer of the present invention is administered either per se or as a part of a pharmaceutical composition; the pharmaceutical composition further includes a pharmaceutically acceptable carrier, as described herein.

According to an additional aspect of the present invention there is provided a medical device which includes the polymer of the present invention and a delivery system configured for delivering the polymer to a bodily site of a subject.

According to further features in the preferred embodiments of the invention described below, the polymer forms a part of a pharmaceutical composition, and the pharmaceutical composition further includes a pharmaceutically acceptable carrier.

According to still further features in the described preferred embodiments the delivery is effected by inhalation, and the delivery system is selected from the group consisting of a metered dose inhaler, a respirator, a nebulizer inhaler, a dry powder inhaler, an electric warmer, a vaporizer, an atomizer and an aerosol generator.

According to still further features in the described preferred embodiments the delivery is effected transdermally, and the delivery system is selected from the group consisting of an adhesive plaster and a skin patch.

According to still further features in the described preferred embodiments the delivery is effected topically and the delivery system is selected from the group consisting of an adhesive strip, a bandage, an adhesive plaster, a wound dressing and a skin patch.

According to still further features in the described preferred embodiments the delivery is effected by implanting the medical device in a bodily organ. Preferably the delivery system further includes a biocompatible matrix which in turn includes a biodegradable polymer and further includes a slow release carrier.

According to still an additional aspect of the present invention there is provided a food preservative which includes an effective amount of the polymer of the present invention, and preferably further includes an edible carrier.

According to a further aspect of the present invention there is provided an imaging probe for detecting a pathogenic microorganism as described herein, which includes a polymer as described herein, and one or more labeling agent, as described herein, attached thereto.

According to further features in the preferred embodiments of the invention described below, the labeling agent(s) is attached to a side chain of an amino acid residue, a C-terminus and/or a N-terminus of the polymer and/or one of the hydrophobic residues of the polymer of the present invention.

The present invention successfully addresses the shortcomings of the presently known configurations by providing a novel class of antimicrobial polymers, which combine the merits of therapeutically active antimicrobial peptides, e.g., high efficacy and specificity, without exhibiting the disadvantages of peptides.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawing(s) will be provided by the Office upon reciuest and payment of the necessary fee. The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 4 presents the circular dichroism spectra of two exemplary polymers according to the present invention, $C_{12}K(NC_8K)_5NH_2$ (SEQ ID NO: 43) and $C_{12}K(NC_8K)_7NH_2$ (SEQ ID NO: 45), taken in the designated media at polymer concentration of 100 µM (liposome concentration of 2 mM), expressed as mean residue molar ellipticity, and compared with a 15-residue control peptide, an acylated dermaseptin S4 derivative (data represent average values from three separate recordings);

DESCRIPTION OF THE PREFERRED EMBODIMENTS

Figure 1:
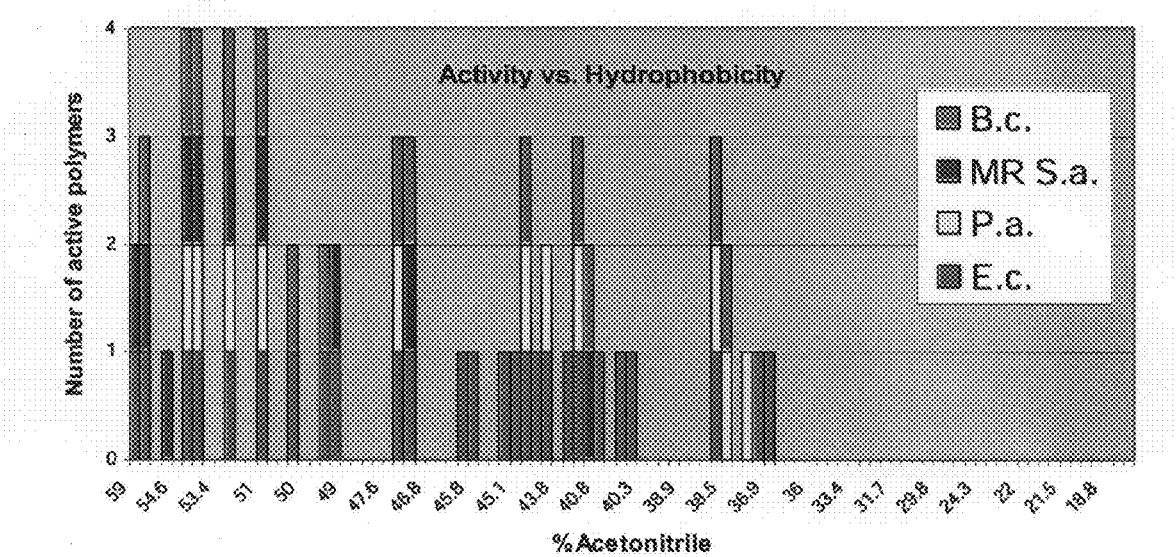
FIG. 1 presents a cumulative bar graph demonstrating the high correlation between the antimicrobial activity and the hydrophobicity of exemplary polymers according to the present invention, by marking the polymers which exhibited a significant microbial activity (MIC value of less than 50 □M) against $E.$ $coli$ (in red bars), $P.$ $aeruginosa$ (in yellow bars), methicilin-resistant $S.$ $aureus$ (in blue bars) and $B.$ $cereus$ (in green bars), on the scale of the acetonitrile percentages in the mobile phase at which the polymers were eluted on a reverse phase HPLC column.

The present invention is of a novel class of polymeric antimicrobial agents which are designed to exert antimicrobial activity while being stable, non-toxic and avoiding development of resistance thereto, and can therefore be beneficially utilized in the treatment of various medical conditions associated with pathogenic microorganisms. The present invention is further of pharmaceutical compositions, medical devices and food preservatives containing same. The antimicrobial polymers of the present invention preferably include one or more positively charged amino acid residues and one or hydrophobic moiety residues attached one to another.

The principles and operation of the present invention may be better understood with reference to the figures and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

As discussed above, the use of classical modern antibiotic agents such as tetracycline, gentamicin, ciprofloxacin and methicillin has become during the years severely limited by the development of resistance thereto. Extensive studies have therefore been conducted in a search for novel antimicrobial agents that would circumvent the resistance induction.

As further discussed above, naturally occurring antimicrobial peptides (AMPs) are exceptionally potent antimicrobial agents, but as pharmaceuticals they suffer from the limitations associated with peptide production, maintenance and modes of clinical administration for therapeutic use.

Based on the knowledge which accumulated over the years on the nature of antimicrobial peptides and the limitations associated with their use, the present inventors hypothesized that in order to achieve a novel class of antimicrobial agents devoid of the resistance-inducing drawbacks of classical antibiotic agents, and those of AMPs, three key attributes of AMPs needs to be maintained: a flexible structure, an amphiphatic character and a net positive charge.

While conceiving the present invention, it was envisioned that a flexible polymeric structure will serve the objective of avoiding the development of resistance in the target microorganism. It was further envisioned that use of amino acids, as defined hereinbelow, can serve as a basis for both a polymer as well as a source for net positive charge.

While further conceiving the present invention, it was hypothesized that avoiding a pure amino acid polypeptide structure will not only resolve the production and maintenance issues limiting the use of polypeptides as drugs, but also alleviate the sever limitations restricting the administration of polypeptides as drugs. Thus, it was envisioned that the desired amphiphatic trait of the envisioned polymer may arise from non-amino acid hydrophobic moieties, such as, but not limited to fatty acids and the likes.

While reducing the present invention to practice, as is demonstrated in the Examples section that follows, the present inventors have developed and successfully produced a novel class of polymers which were shown to exhibit high antimicrobial activity, low resistance induction, non-hemolyticity, resistibility to plasma proteases and high affinity to microbial membranes.

While further conceiving the present invention, it was envisioned that conjugating an active agent to the polymeric structure, such as a labeling agent and/or a therapeutically active agent, will combine the affinity of the polymers of the present invention to microbial cells, and the utility of the additional active agent. In cases where the active agent is a labeling agent, the combination will assist in locating and diagnosing concentration of microbial growth in a host, and in cases where the active agent is a therapeutically active agent, synergistic therapeutic effects could be achieved, resulting from the dual therapeutic effect of the therapeutically active agent and the antimicrobial polymeric structure. In addition, targeted delivery of the therapeutic agent could be achieved.

Thus, according to one aspect of the present invention, there is provided a polymer, having an antimicrobial activity, which comprises a plurality (e.g., two or more) amino acid residues and one or more hydrophobic moiety residues, wherein at least one of the hydrophobic moiety residues is covalently linked to at least two amino acid residues via the N-alpha of one amino acid residue and/or the C-alpha of the other amino acid residue. Therefore, the polymer is a chain made of a sequence of amino acid residues, interrupted by one or more hydrophobic moiety residues.

As used herein throughout the term "amino acid" or "amino acids" is understood to include the 20 genetically coded amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids and other non-naturally occurring amino acids.

Tables 1 and 2 below list the genetically encoded amino acids (Table 1) and non-limiting examples of non-conventional/modified amino acids (Table 2) which can be used with the present invention.

TABLE 1

| Amino acid | Three-Letter Abbreviation | One-letter Symbol |
| --- | --- | --- |
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Iie | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

TABLE 2

| Non-conventional amino acid | Code | Non-conventional amino acid | Code |
| --- | --- | --- | --- |
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
| aminoisobutyric acid | Aib | L-N-methylaspartic acid | Nmasp |
| aminonorbornyl-carboxylate | Norb | L-N-methylcysteine | Nmcys |
| Cyclohexylalanine | Chexa | L-N-methylglutamine | Nmgln |
| Cyclopentylalanine | Cpen | L-N-methylglutamic acid | Nmglu |
| D-alanine | Dal | L-N-methylhistidine | Nmhis |
| D-arginine | Darg | L-N-methylisolleucine | Nmile |
| D-aspartic acid | Dasp | L-N-methylleucine | Nmleu |
| D-cysteine | Dcys | L-N-methyllysine | Nmlys |
| D-glutamine | Dgln | L-N-methylmethionine | Nmmet |

TABLE 2-continued

| Non-conventional amino acid | Code | Non-conventional amino acid | Code |
|---|---|---|---|
| D-glutamic acid | Dglu | L-N-methylnorleucine | Nmnle |
| D-histidine | Dhis | L-N-methylnorvaline | Nmnva |
| D-isoleucine | Dile | L-N-methylornithine | Nmorn |
| D-leucine | Dleu | L-N-methylphenylalanine | Nmphe |
| D-lysine | Dlys | L-N-methylproline | Nmpro |
| D-methionine | Dmet | L-N-methylserine | Nmser |
| D/L-ornithine | D/Lorn | L-N-methylthreonine | Nmthr |
| D-phenylalanine | Dphe | L-N-methyltryptophan | Nmtrp |
| D-proline | Dpro | L-N-methyltyrosine | Nmtyr |
| D-serine | Dser | L-N-methylvaline | Nmval |
| D-threonine | Dthr | L-N-methylethylglycine | Nmetg |
| D-tryptophan | Dtrp | L-N-methyl-t-butylglycine | Nmtbug |
| D-tyrosine | Dtyr | L-norleucine | Nle |
| D-valine | Dval | L-norvaline | Nva |
| D-α-methylalanine | Dmala | α-methyl-aminoisobutyrate | Maib |
| D-α-methylarginine | Dmarg | α-methyl-γ-aminobutyrate | Mgabu |
| D-α-methylasparagine | Dmasn | α-methylcyclohexylalanine | Mchexa |
| D-α-methylaspartate | Dmasp | α-methylcyclopentylalanine | Mcpen |
| D-α-methylcysteine | Dmcys | α-methyl-α-napthylalanine | Manap |
| D-α-methylglutamine | Dmgln | α-methylpenicillamine | Mpen |
| D-α-methylhistidine | Dmhis | N-(4-aminobutyl)glycine | Nglu |
| D-α-methylisoleucine | Dmile | N-(2-aminoethyl)glycine | Naeg |
| D-α-methylleucine | Dmleu | N-(3-aminopropyl)glycine | Norn |
| D-α-methyllysine | Dmlys | N-amino-a-methylbutyrate | Nmaabu |
| D-α-methylmethionine | Dmmet | α-napthylalanine | Anap |
| D-α-methylornithine | Dmorn | N-benzylglycine | Nphe |
| D-α-methylphenylalanine | Dmphe | N-(2-carbamylethyl)glycine | Ngln |
| D-α-methylproline | Dmpro | N-(carbamylmethyl)glycine | Nasn |
| D-α-methylserine | Dmser | N-(2-carboxyethyl)glycine | Nglu |
| D-α-methylthreonine | Dmthr | N-(carboxymethyl)glycine | Nasp |
| D-α-methyltryptophan | Dmtrp | N-cyclobutylglycine | Ncbut |
| D-α-methyltyrosine | Dmty | N-cycloheptylglycine | Nchep |
| D-α-methylvaline | Dmval | N-cyclohexylglycine | Nchex |
| D-α-methylalnine | Dnmala | N-cyclodecylglycine | Ncdec |
| D-α-methylarginine | Dnmarg | N-cyclododeclglycine | Ncdod |
| D-α-methylasparagine | Dnmasn | N-cyclooctylglycine | Ncoct |
| D-α-methylasparatate | Dnmasp | N-cyclopropylglycine | Ncpro |
| D-α-methylcysteine | Dnmcys | N-cycloundecylglycine | Ncund |
| D-N-methylleucine | Dnmleu | N-(2,2-diphenylethyl)glycine | Nbhm |
| D-N-methyllysine | Dnmlys | N-(3,3-diphenylpropyl)glycine | Nbhe |
| N-methylcyclohexylalanine | Nmchexa | N-(3-indolylethyl) glycine | Nhtrp |
| D-N-methylornithine | Dnmorn | N-methyl-γ-aminobutyrate | Nmgabu |
| N-methylglycine | Nala | D-N-methylmethionine | Dnmmet |
| N-methylaminoisobutyrate | Nmaib | N-methylcyclopentylalanine | Nmcpen |
| N-(1-methylpropyl)glycine | Nile | D-N-methylphenylalanine | Dnmphe |
| N-(2-methylpropyl)glycine | Nile | D-N-methylproline | Dnmpro |
| N-(2-methylpropyl)glycine | Nleu | D-N-methylserine | Dnmser |
| D-N-methyltryptophan | Dnmtrp | D-N-methylserine | Dnmser |
| D-N-methyltyrosine | Dnmtyr | D-N-methylthreonine | Dnmthr |
| D-N-methylvaline | Dnmval | N-(1-methylethyl)glycine | Nva |
| γ-aminobutyric acid | Gabu | N-methyla-napthylalanine | Nmanap |
| L-t-butylglycine | Tbug | N-methylpenicillamine | Nmpen |
| L-ethylglycine | Etg | N-(p-hydroxyphenyl)glycine | Nhtyr |
| L-homophenylalanine | Hphe | N-(thiomethyl)glycine | Ncys |
| L-α-methylarginine | Marg | penicillamine | Pen |
| L-α-methylaspartate | Masp | L-α-methylalanine | Mala |
| L-α-methylcysteine | Mcys | L-α-methylasparagine | Masn |
| L-α-methylglutamine | Mgln | L-α-methyl-t-butylglycine | Mtbug |
| L-α-methylhistidine | Mhis | L-methylethylglycine | Metg |
| L-α-methylisoleucine | Mile | L-α-methylglutamate | Mglu |
| D-N-methylglutamine | Dnmgln | L-α-methylhomo phenylalanine | Mhphe |
| D-N-methylglutamate | Dnmglu | N-(2-methylthioethyl)glycine | Nmet |
| D-N-methylhistidine | Dnmhis | N-(3-guanidinopropyl)glycine | Narg |
| D-N-methylisoleucine | Dnmile | N-(1-hydroxyethyl)glycine | Nthr |
| D-N-methylleucine | Dnmleu | N-(hydroxyethyl)glycine | Nser |
| D-N-methyllysine | Dnmlys | N-(imidazolylethyl)glycine | Nhis |
| N-methylcyclohexylalanine | Nmchexa | N-(3-indolylethyl)glycine | Nhtrp |
| D-N-methylornithine | Dnmorn | N-methyl-γ-aminobutyrate | Nmgabu |
| N-methylglycine | Nala | D-N-methylmethionine | Dnmmet |
| N-methylaminoisobutyrate | Nmaib | N-methylcyclopentylalanine | Nmcpen |
| N-(1-methylpropyl)glycine | Nile | D-N-methylphenylalanine | Dnmphe |
| N-(2-methylpropyl)glycine | Nleu | D-N-methylproline | Dnmpro |
| D-N-methyltryptophan | Dnmtrp | D-N-methylserine | Dnmser |
| D-N-methyltyrosine | Dnmtyr | D-N-methylthreonine | Dnmthr |
| D-N-methylvaline | Dnmval | N-(1-methylethyl)glycine | Nval |
| γ-aminobutyric acid | Gabu | N-methyla-napthylalanine | Nmanap |
| L-t-butylglycine | Tbug | N-methylpenicillamine | Nmpen |

TABLE 2-continued

| Non-conventional amino acid | Code | Non-conventional amino acid | Code |
|---|---|---|---|
| L-ethylglycine | Etg | N-(p-hydroxyphenyl)glycine | Nhtyr |
| L-homophenylalanine | Hphe | N-(thiomethyl)glycine | Ncys |
| L-α-methylarginine | Marg | penicillamine | Pen |
| L-α-methylaspartate | Masp | L-α-methylalanine | Mala |
| L-α-methylcysteine | Mcys | L-α-methylasparagine | Masn |
| L-α-methylglutamine | Mgln | L-α-methyl-t-butylglycine | Mtbug |
| L-α-methylhistidine | Mhis | L-methylethylglycine | Metg |
| L-α-methylisoleucine | Mile | L-α-methylglutamate | Mglu |
| L-α-methylleucine | Mleu | L-α-methylhomophenylalanine | Mhphe |
| L-α-methylmethionine | Mmet | N-(2-methylthioethyl)glycine | Nmet |
| L-α-methylnorvaline | Mnva | L-α-methyllysine | Mlys |
| L-α-methylphenylalanine | Mphe | L-α-methylnorleucine | Mnle |
| L-α-methylserine | mser | L-α-methylornithine | Morn |
| L-α-methylvaline | Mtrp | L-α-methylproline | Mpro |
| L-α-methylleucine | Mval Nnbhm | L-α-methylthreonine | Mthr |
| N-(N-(2,2-diphenylethyl)carbamylmethyl-glycine | Nnbhm | L-α-methyltyrosine | Mtyr |
| 1-carboxy-1-(2,2-diphenyl ethylamino)cyclopropane | Nmbc | L-N-methylhomophenylalanine | Nmhphe |
| N-(N-(3,3-diphenylpropyl)carbamylmethyl(1)glycine | Nnbhe | D/L-citrulline | D/Lctr |

As used herein, the phrase "hydrophobic moiety" describes a chemical moiety that has a minor or no affinity to water, that is, which has a low or no dissolvability in water and often in other polar solvents. Exemplary suitable hydrophobic moieties for use in the context of the present invention, include, without limitation, hydrophobic moieties that consist predominantly of one or more hydrocarbon chains and/or aromatic rings, and one or more functional groups which may be non-hydrophobic, but do not alter the overall hydrophobicity of the hydrophobic moiety. Representative examples include, without limitation, fatty acids, hydrophobic amino acids (amino acids with hydrophobic side-chains), alkanes, alkenes, aryls and the likes, as these terms are defined herein, and any combination thereof.

As used herein, the phrase "chemical moiety" describes a residue of a chemical compound, which typically has certain functionality. As is well accepted in the art, the term "residue" refers herein to a major portion of a molecule which is covalently linked to another molecule.

As used herein, the phrase "functional group" describes a chemical group that is capable of undergoing a chemical reaction that typically leads to a bond formation. The bond, according to the present invention, is preferably a covalent bond. Chemical reactions that lead to a bond formation include, for example, nucleophilic and electrophilic substitutions, nucleophilic and electrophilic addition reactions, addition-elimination reactions, cycloaddition reactions, rearrangement reactions and any other known organic reactions that involve a functional group.

A polymer, according to the present invention, may have one or more hydrophobic moiety residues, whereby at least one is linked to one amino acid at one end and to another amino acid residue at another end, and another may elongate the polymeric chain by being linked to either one of the termini, i.e., the N-alpha of a terminal amino acid residue and/or the C-alpha of a terminal amino acid residue. Optionally, a second hydrophobic moiety may be linked to the side-chain of an amino acid residue in the polymer.

The polymer, according to the present invention, preferably includes from 2 to 50 amino acid residues. More preferably, the polymer includes from 2 to 12 amino acid residues and more preferably from 2 to 8 amino acid residues.

The net positive charge of the polymer is maintained by having one or more positively charged amino acid residues in the polymer, optionally in addition to the positively charged N-terminus amine, when present in its free form.

In one preferred embodiment of the present invention, all the amino acid residues in the polymer are positively charged amino acid residues. An exemplary polymer according to this embodiment includes a plurality of lysine residues.

As used herein the phrase "positively charged amino acid" describes a hydrophilic amino acid with a side chain pKa value of greater than 7, namely a basic amino acid. Basic amino acids typically have positively charged side chains at physiological pH due to association with a hydronium ion. Naturally occurring (genetically encoded) basic amino acids include lysine (Lys, K), arginine (Arg, R) and histidine (His, H), while non-natural (non-genetically encoded, or non-standard) basic amino acids include, for example, ornithine, 2,3,-diaminopropionic acid, 2,4-diaminobutyric acid, 2,5,6-tri-aminohexanoic acid, 2-amino-4-guanidinobutanoic acid, and homoarginine.

In one embodiment of the present invention, each of the components in the polymer according to the present embodiments is preferably linked to the other by a peptide bond.

The term "peptide bond" as used herein refers to an amide group, namely, a —(C=O)NH— group, which is typically formed by a condensation reaction between a carboxylic group and an amine group, as these terms are defined herein.

However, the polymers of the present embodiments may have other bonds linking the various components in the polymeric structure. Such non-peptidic bonds may render the polymer more stable while in a body or more capable of penetrating into cells. Thus, peptide bonds (—(C=O)NH—) within the polymer may be replaced, for example, by N-methylated amide bonds (—(C=O)NCH$_3$—), ester bonds (—C(R)H—C(=O)—O—C(R)—N—), ketomethylen bonds (—C(=O)CH$_2$—), aza bonds (—NH—N(R)—C(=O)—), wherein R is any alkyl, e.g., methyl, carba bonds (—CH$_2$—NH—), hydroxyethylene bonds (—CH(OH)—CH$_2$—), thioamide bonds (—CS—NH—), olefinic double bonds (—CH=CH—), retro amide bonds (—NH—C(=O)—), peptide derivatives (—N(R)—CH$_2$—C(=O)—), wherein R is the "normal" side chain, naturally presented on the carbon atom. These modifications can occur at any of the bonds along the polymer chain and even several (2-3) at the same time.

In a preferred embodiment, all of the bonds in the polymer, linking the amino acid residues and hydrophobic moiety residues to each other, are peptide bonds. For example, in one embodiment, the polymer is made of an amino acid residue linked by a peptide bond to a hydrophobic moiety residue which in turn is linked to a second amino acid residue by another peptide bond. In another example, the polymer of the previous example is elongated by a second hydrophobic moiety residue which is linked to any one of the N- or C-termini by a peptide bond, etcetera.

The polymer, according to the present invention, preferably comprises from 1 to 50 hydrophobic moiety residues. More preferably, the polymer comprises from 1 to 12 hydrophobic moiety residues and more preferably from 1 to 8 hydrophobic moiety residues.

The hydrophobic moieties that are used in the context of this and other aspects of the present invention preferably have one or more hydrocarbon chains, and are capable of linking to one or two other components in the polymer (e.g., one or two of an amino acid residue and another hydrophobic moiety) via two peptide bonds. These moieties therefore preferably have a carboxylic group at one end of the hydrocarbon chain (for linking a free amine group) and an amine group at the other (for linking a carboxylic acid group).

The hydrocarbon chain connecting the carboxylic and amine groups in such a hydrophobic moiety preferably has from 4 to 30 carbon atoms.

In a preferred embodiment of the present invention, the hydrophobic moiety residue is a fatty acid residue wherein the hydrocarbon chain can be unbranched and saturated, branched and saturated, unbranched and unsaturated or branched and unsaturated. More preferably the hydrocarbon chain of the fatty acid residue is an unbranched and saturated chain having from 4 to 30 carbon atoms. Non-limiting example of such fatty acid residues are butyric acid residue, caprylic acid residue and lauric acid residue.

In a more preferred embodiment, the fatty acid residue has an amine on the last carbon of the hydrocarbon chain (with respect to the carboxylic acid group). Such a fatty acid residue is referred to herein as an ω-amino fatty acid residue. Again here the hydrocarbon chain of the ω-amino fatty acid residue may have from 4 to 30 carbon atoms.

Non-limiting example of such ω-amino fatty acids are 4-amino-butyric acid, 6-amino-caproic acid, 8-amino-caprylic acid, 10-amino-capric acid, 12-amino-lauric acid, 14-amino-myristic acid, 16-amino-palmitic acid, 18-amino-stearic acid, 18-amino-oleic acid, 16-amino-palmitoleic acid, 18-amino-linoleic acid, 18-amino-linolenic acid and 20-amino-arachidonic acid.

According to a preferred embodiment of the present invention, the hydrophobic moiety is selected from the group consisting of 4-amino-butyric acid, 8-amino-caprylic acid and 12-amino-lauric acid.

The polymers described herein can be collectively represented by the following general formula I:

$$X-W_0-[A_1-Z_1-D_1]-W_1-[A_2-Z_2-D_2]-W_2-\ldots[A_n-Z_n-D_n]-W_n-Y \quad \text{Formula I}$$

wherein:

n is an integer from 2 to 50, preferably from 2 to 12 and more preferably from 2 to 8;

$A_1, A_2, \ldots, A_n$ are each independently an amino acid residue, preferably a positively charged amino acid residue, more preferably all of $A_1, A_2, \ldots, A_n$ are positively charged amino acid residues as discussed hereinabove, such as histidine residues, lysine residues, ornithine residues and arginine residues, and most preferably all the positively charged amino acid residues are lysine residues;

$D_1, D_2, \ldots, D_n$ are each independently a hydrophobic moiety residue, as difined and discussed hereinabove, or absent, provided that at least one such hydrophobic moiety residue exists in the polymer, preferably at least one of the hydrophobic moiety residues is a ω-amino-fatty acid residue;

Connecting each monomer of the residue are linking moieties, denoted $Z_1, Z_2, \ldots Z_n$ and $W_0, W_1, W_2, \ldots, W_n$, each of which independently linking an amino acid residue and a hydrophobic moiety residue or absent, preferably at least one of the linking moieties is a peptide bond and most preferable all the linking moieties are peptide bonds;

The fringes of the polymer, denoted X and Y, may each independently be hydrogen, an amino acid residue, a hydrophobic moiety residue or is another polymer having the general Formula I.

As discussed above, one or more of the hydrophobic moiety residues may be attached to a side chain of one or more of the amino acid residues of the polymer, i.e., act as a branch of the main polymer.

The polymers according to the present embodiments can be readily synthesized. For example, polymers in which the linking moieties are peptide bonds, and hence resemble natural and synthetic peptides in this respect, can be prepared by classical methods known in the art for peptide syntheses. Such methods include, for example, standard solid phase techniques. The standard methods include exclusive solid phase synthesis, partial solid phase synthesis methods, fragment condensation, classical solution synthesis, and even by recombinant DNA technology. See, e.g., Merrifield, J. Am. Chem. Soc., 85:2149 (1963), incorporated herein by reference. Solid phase peptide synthesis procedures are well known in the art and further described by John Morrow Stewart and Janis Dillaha Young, Solid Phase Peptide Syntheses (2nd Ed., Pierce Chemical Company, 1984).

The polymers of the present invention can be purified, for example, by preparative high performance liquid chromatography [Creighton T. (1983) Proteins, structures and molecular principles. WH Freeman and Co. N.Y.].

Apart from having beneficial antimicrobial activity per se, as detailed herein, the polymers of the present invention may include an additional active agent such as a labeling agent and/or a therapeutically active agent attached thereto. The conjugation of the active agent to a polymer of the present invention can provide a dual utility for the polymer. When the additional active agent is a labeling agent, the conjugation thereof to an antimicrobial polymer of the present invention, having a high affinity to microbial cells, can assist in the location, diagnosis and targeting of microbial growth loci in a host. When the additional active agent is a therapeutically active agent, the conjugation thereof to an antimicrobial polymer of the present invention will exert a dual and possibly synergistic antimicrobial activity.

According to preferred embodiments of the present invention, the one or more active agents may be attached to the polymer at any substitutable position. Examples of such substitutable positions include, without limitation, a side chain of any one or more of the amino acid residues in the polymer, any one of the linking moieties of the polymer, any one of the N- and C-termini of the polymer and any one or more of the hydrophobic moiety residues in the polymer.

Hence, as used herein, the phrase "a therapeutically active agent" describes a chemical substance, which exhibit a therapeutic activity when administered to a subject As used herein, the phrase "labeling agent" refers to a detectable moiety or a probe and includes, for example, chromophores, fluorescent compounds, phosphorescent compounds, heavy metal clusters, and radioactive labeling compounds, as well as any other known detectable moieties.

Labeling of microbial growth loci in a host is critical for the diagnosis and efficient targeting of the photogenic microorganism and treatment thereof.

Adding a therapeutically active agent to the polymer can provide a solution for many deficiencies of presently known therapeutically active agent against photogenic microorganisms, such as resistance of the photogenic microorganism to the therapeutically active agent, specificity of the therapeutically active agent to photogenic microorganism and general efficacy weakness. The polymers of the present invention can exhibit not only antimicrobial activity per se by virtue of their structure and chemical properties, but can also provide targeting capacity as a delivery vehicle to a presently know therapeutically active agents and further provide membrane permeability to presently know therapeutically active agents due to their capability to exert disturbance in the membrane structure of photogenic microorganisms.

Non-limiting examples of therapeutically active agents that can be beneficially used in this and other contexts of the present invention include, without limitation, one or more of an agonist residue, an amino acid residue, an analgesic residue, an antagonist residue, an antibiotic agent residue, an antibody residue, an antidepressant agent, an antigen residue, an anti-histamine residue, an anti-hypertensive agent, an anti-inflammatory drug residue, an anti-metabolic agent residue, an antimicrobial agent residue, an antioxidant residue, an anti-proliferative drug residue, an antisense residue, a chemotherapeutic drug residue, a co-factor residue, a cytokine residue, a drug residue, an enzyme residue, a growth factor residue, a heparin residue, a hormone residue, an immunoglobulin residue, an inhibitor residue, a ligand residue, a nucleic acid residue, an oligonucleotide residue, a peptide residue, a phospholipid residue, a prostaglandin residue, a protein residue, a toxin residue, a vitamin residue and any combination thereof The combined therapeutic effect is particularly advantageous when the therapeutically active agent is an antimicrobial or an antibiotic agent. The combined activity of the polymers of the present invention and that of an additional antimicrobial/antibiotic agent may provide the antimicrobial/antibiotic agent the capacity to overcome the known limitations of these drugs such as targeting, specificity, efficacy, drug-resistance etcetera. Synergism may also be achieved.

Non-limiting examples of antimicrobial and antibiotic agents that are suitable for use in this context of the present invention include, without limitation, mandelic acid, 2,4-dichlorobenzenemethanol, 4-[bis(ethylthio)methyl]-2-methoxyphenol, 4-epi-tetracycline, 4-hexylresorcinol, 5,12-dihydro-5,7,12,14-tetrazapentacen, 5-chlorocarvacrol, 8-hydroxyquinoline, acetarsol, acetylkitasamycin, acriflavin, alatrofloxacin, ambazon, amfomycin, amikacin, amikacin sulfate, aminoacridine, aminosalicylate calcium, aminosalicylate sodium, aminosalicylic acid, ammoniumsulfobituminat, amorolfin, amoxicillin, amoxicillin sodium, amoxicillin trihydrate, amoxicillin-potassium clavulanate combination, amphotericin B, ampicillin, ampicillin sodium, ampicillin trihydrate, ampicillin-sulbactam, apalcillin, arbekacin, aspoxicillin, astromicin, astromicin sulfate, azanidazole, azidamfenicol, azidocillin, azithromycin, azlocillin, aztreonam, bacampicillin, bacitracin, bacitracin zinc, bekanamycin, benzalkonium, benzethonium chloride, benzoxonium chloride, berberine hydrochloride, biapenem, bibrocathol, biclotymol, bifonazole, bismuth subsalicylate, bleomycin antibiotic complex, bleomycin hydrochloride, bleomycin sulfate, brodimoprim, bromochlorosalicylanilide, bronopol, broxyquinolin, butenafine, butenafine hydrochloride, butoconazol, calcium undecylenate, candicidin antibiotic complex, capreomycin, carbenicillin, carbenicillin disodium, carfecillin, carindacillin, carumonam, carzinophilin, caspofungin acetate, cefacetril, cefaclor, cefadroxil, cefalexin, cefalexin hydrochloride, cefalexin sodium, cefaloglycin, cefaloridine, cefalotin, cefalotin sodium, cefamandole, cefamandole nafate, cefamandole sodium, cefapirin, cefapirin sodium, cefatrizine, cefatrizine propylene glycol, cefazedone, cefazedone sodium salt, cefazolin, cefazolin sodium, cefbuperazone, cefbuperazone sodium, cefcapene, cefcapene pivoxil hydrochloride, cefdinir, cefditoren, cefditoren pivoxil, cefepime, cefepime hydrochloride, cefetamet, cefetamet pivoxil, cefixime, cefinenoxime, cefinetazole, cefinetazole sodium, cefininox, cefininox sodium, cefmolexin, cefodizime, cefodizime sodium, cefonicid, cefonicid sodium, cefoperazone, cefoperazone sodium, ceforanide, cefoselis sulfate, cefotaxime, cefotaxime sodium, cefotetan, cefotetan disodium, cefotiam, cefotiam hexetil hydrochloride, cefotiam hydrochloride, cefoxitin, cefoxitin sodium, cefozopran hydrochloride, cefpiramide, cefpiramide sodium, cefpirome, cefpirome sulfate, cefpodoxime, cefpodoxime proxetil, cefprozil, cefquinome, cefradine, cefroxadine, cefsulodin, ceftazidime, cefteram, cefteram pivoxil, ceftezole, ceftibuten, ceftizoxime, ceftizoxime sodium, ceftriaxone, ceftriaxone sodium, cefuroxime, cefuroxime axetil, cefuroxime sodium, cetalkonium chloride, cetrimide, cetrimonium, cetylpyridinium, chloramine T, chloramphenicol, chloramphenicol palmitate, chloramphenicol succinate sodium, chlorhexidine, chlormidazole, chlormidazole hydrochloride, chloroxylenol, chlorphenesin, chlorquinaldol, chlortetracycline, chlortetracycline hydrochloride, ciclacillin, ciclopirox, cinoxacin, ciprofloxacin, ciprofloxacin hydrochloride, citric acid, clarithromycin, clavulanate potassium, clavulanate sodium, clavulanic acid, clindamycin, clindamycin hydrochloride, clindamycin palmitate hydrochloride, clindamycin phosphate, clioquinol, cloconazole, cloconazole monohydrochloride, clofazimine, clofoctol, clometocillin, clomocycline, clotrimazol, cloxacillin, cloxacillin sodium, colistin, colistin sodium methanesulfonate, colistin sulfate, cycloserine, dactinomycin, danofloxacin, dapsone, daptomycin, daunorubicin, DDT, demeclocycline, demeclocycline hydrochloride, dequalinium, dibekacin, dibekacin sulfate, dibrompropamidine, dichlorophene, dicloxacillin, dicloxacillin sodium, didecyldimethylammonium chloride, dihydrostreptomycin, dihydrostreptomycin sulfate, diiodohydroxyquinolin, dimetridazole, dipyrithione, dirithromycin, DL-menthol, D-menthol, dodecyltriphenylphosphonium bromide, doxorubicin, doxorubicin hydrochloride, doxycycline, doxycycline hydrochloride, econazole, econazole nitrate, enilconazole, enoxacin, enrofloxacin, eosine, epicillin, ertapenem sodium, erythromycin, erythromycin estolate, erythromycin ethyl succinate, erythromycin lactobionate, erythromycin stearate, ethacridine, ethacridine lactate, ethambutol, ethanoic acid, ethionamide, ethyl alcohol, eugenol, exalamide, faropenem, fenticonazole, fenticonazole nitrate, fezatione, fleroxacin, flomoxef, flomoxef sodium, florfenicol, flucloxacillin, flucloxacillin magnesium, flucloxacillin sodium, fluconazole, flucytosine, flumequine, flurithromycin, flutrimazole, fosfomycin, fosfomycin calcium, fosfomycin sodium, framycetin, framycetin sulphate, furagin, furazolidone, fusafungin, fusidic acid, fusidic acid sodium salt, gatifloxacin, gemifloxacin, gentamicin antibiotic complex, gentamicin cla, gentamycin sulfate, glutaraldehyde, gramicidin, grepafloxacin, griseofulvin, halazon, haloprogine, hetacillin, hetacillin potassium, hexachlorophene, hexamidine, hexetidine, hydrargaphene, hydroquinone, hygromycin, imipenem, isepamicin, isepamicin sulfate, isoconazole, isoconazole nitrate, isoniazid, isopropanol, itraconazole, josamycin, josamycin propionate, kanamycin, kanamycin sulphate, ketoconazole, kitasamycin, lactic acid, lanoconazole, lenampicillin, leucomycin A1, leucomycin A13, leucomycin A4, leucomycin A5, leucomycin A6, leucomycin A7, leucomycin A8, leucomycin A9, levofloxacin, lincomycin, lincomycin hydrochloride, linezolid, liranaftate, 1-menthol, lomefloxacin, lomefloxacin hydrochloride, loracarbef, lymecyclin, lysozyme, mafenide acetate, magnesium monoperoxophthalate hexahydrate, mecetronium ethylsulfate, mecillinam, meclocycline, meclocycline sulfosalicylate, mepartricin, merbromin, meropenem, metalkonium chloride, metampicillin, methacycline, methenamin, methyl salicylate, methylbenzethonium chloride, methylrosanilinium chloride, meticillin, meticillin sodium, metronidazole, metronidazole benzoate, mezlocillin, mezlocillin sodium, miconazole, miconazole nitrate, micronomicin, micronomicin sulfate, midecamycin, minocycline, minocycline hydrochloride, miocamycin, miristalkonium chloride, mitomycin c, monensin, monensin sodium, morinamide, moxalactam, moxalactam disodium, moxifloxacin, mupirocin, mupirocin calcium, nadifloxacin, nafcillin, nafcillin sodium, naftifine, nalidixic acid, natamycin, neomycin a, neomycin antibiotic complex, neomycin C, neomycin sulfate, neticonazole, netilmicin, netilmicin sulfate, nifuratel, nifuroxazide, nifurtoinol, nifurzide, nimorazole, niridazole, nitrofurantoin, nitrofurazone, nitroxolin, norfloxacin, novobiocin, nystatin antibiotic complex, octenidine, ofloxacin, oleandomycin, omoconazol, orbifloxacin, ornidazole, ortho-phenylphenol, oxacillin, oxacillin sodium, oxiconazole, oxiconazole nitrate, oxoferin, oxolinic acid, oxychlorosene, oxytetracycline, oxytetracycline calcium, oxytetracycline hydrochloride, panipenem, paromomycin, paromomycin sulfate, pazufloxacine, pefloxacin, pefloxacin mesylate, penamecillin, penicillin G, penicillin G potassium, penicillin G sodium, penicillin V, penicillin V calcium, penicillin V potassium, pentamidine, pentamidine diisetionate, pentamidine mesilas, pentamycin, phenethicillin, phenol, phenoxyethanol, phenylmercuriborat, PHMB, phthalylsulfathiazole, picloxydin, pipemidic acid, piperacillin, piperacillin sodium, pipercillin sodium-tazobactam sodium, piromidic acid, pivampicillin, pivcefalexin, pivmecillinam, pivmecillinam hydrochloride, policresulen, polymyxin antibiotic complex, polymyxin B, polymyxin B sulfate, polymyxin B 1, polynoxylin, povidone-iodine, propamidin, propenidazole, propicillin, propicillin potassium, propionic acid, prothionamide, protiofate, pyrazinamide, pyrimethamine, pyrithion, pyrroInitrin, quinoline, quinupristin-dalfopristin, resorcinol, ribostamycin, ribostamycin sulfate, rifabutin, rifampicin, rifamycin, rifapentine, rifaximin, ritiometan, rokitamycin, rolitetracycline, rosoxacin, roxithromycin, rufloxacin, salicylic acid, secnidazol, selenium disulphide, sertaconazole, sertaconazole nitrate, siccanin, sisomicin, sisomicin sulfate, sodium thiosulfate, sparfloxacin, spectinomycin, spectinomycin hydrochloride, spiramycin antibiotic complex, spiramycin b, streptomycin, streptomycin sulphate, succinylsulfathiazole, sulbactam, sulbactam sodium, sulbenicillin disodium, sulbentin, sulconazole, sulconazole nitrate, sulfabenzamide, sulfacarbamide, sulfacetamide, sulfacetamide sodium, sulfachlorpyridazine, sulfadiazine, sulfadiazine silver, sulfadiazine sodium, sulfadicramide, sulfadimethoxine, sulfadoxine, sulfaguanidine, sulfalene, sulfamazone, sulfamerazine, sulfamethazine, sulfamethazine sodium, sulfamethizole, sulfamethoxazole, sulfamethoxazol-trimethoprim, sulfamethoxypyridazine, sulfamonomethoxine, sulfamoxol, sulfanilamide, sulfaperine, sulfaphenazol, sulfapyridine, sulfaquinoxaline, sulfasuccinamide, sulfathiazole, sulfathiourea, sulfatolamide, sulfatriazin, sulfisomidine, sulfisoxazole, sulfisoxazole acetyl, sulfonamides, sultamicillin, sultamicillin tosilate, tacrolimus, talampicillin hydrochloride, teicoplanin A2 complex, teicoplanin A2-1, teicoplanin A2-2, teicoplanin A2-3, teicoplanin A2-4, teicoplanin A2-5, teicoplanin A3, teicoplanin antibiotic complex, telithromycin, temafloxacin, temocillin, tenoic acid, terbinafine, terconazole, terizidone, tetracycline, tetracycline hydrochloride, tetracycline metaphosphate, tetramethylthiuram monosulfide, tetroxoprim, thiabendazole, thiamphenicol, thiaphenicol glycinate hydrochloride, thiomersal, thiram, thymol, tibezonium iodide, ticarcillin, ticarcillin-clavulanic acid mixture, ticarcillin disodium, ticarcillin monosodium, tilbroquinol, tilmicosin, timidazole, tioconazole, tobramycin, tobramycin sulfate, tolciclate, tolindate, tolnaftate, toloconium metilsulfat, toltrazuril, tosufloxacin, triclocarban, triclosan, trimethoprim, trimethoprim sulfate, triphenylstibinsulfide, troleandomycin, trovafloxacin, tylosin, tyrothricin, undecoylium chloride, undecylenic acid, vancomycin, vancomycin hydrochloride, viomycin, virginiamycin antibiotic complex, voriconazol, xantocillin, xibomol and zinc undecylenate.

Major parts of the polymers of the present embodiments are based on a repetitive element consisting of a conjugate between an amino acid and a bi-functional hydrophobic moiety. The conjugate may repeat several times in the sequence of the polymer and/or be interrupted and/or flanked by a difference types of conjugates or by single or repeats of amino acid residues and single or repeats of hydrophobic moiety residues.

Hence, according to another aspect of the present invention, there is provided a conjugate which includes an amino acid residue and a hydrophobic moiety residue, as defined and described hereinabove, attached to the N-alpha or the C-alpha of the amino acid residue. The hydrophobic moiety residue in the conjugate of the present invention is designed such that is it capable of forming a bond with an N-alpha or a C-alpha of an additional amino acid residue. Preferably, the hydrophobic moiety residue is conjugated to the amino acid residue via a peptide bond.

The hydrophobic moiety of the conjugate of the present invention is having a bi-functional design which allows the conjugate to serve as a polymerizable conjugate that can form a part of the polymers described and presented herein. Preferably, the hydrophobic moiety which forms a part of the conjugate is having a bi-functionality in the form of a carboxylic group at one end thereof and an amine group at the other end thereof.

Hence, according to another aspect of the present invention, there is provided a process of preparing the conjugate described hereinabove, the general process is based on providing an amino acid, preferably the amino acid is a positively charged amino acid, such as histidine, lysine, ornithine and arginine; providing a hydrophobic moiety as defined and discussed hereinabove having a first functional group that is capable of reacting with an N-alpha of an amino acid residue and a second functional group capable of reacting with a C-alpha of an amino acid; linking the first functional group in the hydrophobic moiety to the amino acid via the N-alpha of the amino acid; or linking the second functional group in the hydrophobic moiety to the amino acid via the C-alpha of the amino acid.

Preferably, the link between the N-alpha or the C-alpha of the amino acid and the hydrophobic moiety is via a peptide bond.

In order to form a peptide bond linking the amino acid to the hydrophobic moiety, the hydrophobic moiety preferably has a carboxylic group at one end thereof and an amine group at the other end thereof.

The antimicrobial polymers as described herein can be beneficially utilized in the treatment of pathogenic microorganism infections, as these are defined hereinbelow. As demonstrated in the Example section that follows, such polymers are by themselves capable of exerting antimicrobial activity. The option to include an additional therapeutically active agent may thus act synergistically as toxic agents against various bacteria, fungi and other microorganisms.

Herein throughout, the phrase "pathogenic microorganism" is used to describe any microorganism which can cause a disease or disorder in a higher organism, such as mammals in general and a human in particular. The pathogenic microorganism may belong to any family of organisms such as, but not limited to prokaryotic organisms, eubacterium, archaebacterium, eukaryotic organisms, yeast, fungi, algae, protozoan, and other parasites. Non-limiting examples of pathogenic microorganism are *Plasmodium falciparum* and related malaria-causing protozoan parasites, Acanthamoeba and other free-living amoebae, *Aeromonas hydrophila*, Anisakis and related worms, *Ascaris lumbricoides, Bacillus cereus, Campylobacter jejuni, Clostridium botulinum, Clostridium perfringens, Cryptosporidium parvum, Cyclospora cayetanensis, Diphyllobothrium, Entamoeba histolytica, Eustrongylides, Giardia lamblia, Listeria monocytogenes, Nanophyetus, Plesiomonas shigelloides, Salmonella, Shigella, Staphylococcus aureus, Streptococcus, Trichuris trichiura, Vibrio cholerae, Vibrio parahaemolyticus, Vibrio vulnificus* and other vibrios, *Yersinia enterocolitica* and *Yersinia pseudotuberculosis*.

Hence, according to another aspect of the present invention, there is provided a method of treating a medical condition associated with a pathogenic microorganism, the method includes administering to a subject in need thereof a therapeutically effective amount of one or more of the polymers, as described hereinabove As used herein, the terms "treating" and "treatment" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein, the phrase "therapeutically effective amount" describes an amount of the composite being administered which will relieve to some extent one or more of the symptoms of the condition being treated.

The method of treatment, according to an embodiment of the present invention, may include the administration of an additional therapeutically active agent, as this is defined and discussed hereinabove.

As mentioned above and demonstrated in the Example section that follows, the antimicrobial polymers of the present invention, alone or in combination with any other therapeutically active agents, can be designed and utilized to destroy pathological microorganisms. The destruction of a pathogenic microorganism is effected by selectively destructing a portion of the cells of a pathogenic microorganism. While most known antibiotics act by interfering selectively with the biosynthesis of one or more of the molecular constituents of the cell-membrane, proteins or nucleic acids, the polymers of the present invention also act by binding and disrupting the outer membrane of the pathogenic microorganism cells. Disrupting the outer membrane of a cell causes its death due to membrane depolarization, leakage of metabolites and/or total loss of cell integrity; therefore the polymers of the present invention also act directly as effective antimicrobial agents by disrupting the metabolism and/or the multiplication processes of the pathogenic microorganism.

As demonstrated in the Examples section that follows, the polymers of the present invention can act synergistically with another antibiotic or other therapeutically active agent by permeabilizing the cells of the pathogenic microorganism; hence exhibit additionally an indirect antimicrobial activity. The results presented hereinbelow permit the conclusion that the polymers of the present invention are potent outer-membrane disintegrating agents. The permeabilizing action of the polymers can increase the uptake of other therapeutically active agents and therefore should be able to potentiate the apparent antimicrobial activity of other drugs and antibiotics.

Medical conditions associated with a pathogenic microorganism include infections, infestation, contaminations and transmissions by or of pathogenic microorganism. In general, a disease causing infection is the invasion into the tissues of a plant or an animal by pathogenic microorganisms. The invasion of body tissues by parasitic worms and other higher pathogenic organisms is commonly referred to as infestation.

Invading organisms such as bacteria produce toxins that damage host tissues and interfere with normal metabolism; some toxins are actually enzymes that break down host tissues. Other bacterial substances may inflict their damage by destroying the host's phagocytes, rendering the body more susceptible to infections by other pathogenic microorganisms. Substances produced by many invading organisms cause allergic sensitivity in the host. Infections may be spread via respiratory droplets, direct contact, contaminated food, or vectors, such as insects. They can also be transmitted sexually and from mother to fetus.

Diseases caused by bacterial infections typically include, for example, actinomycosis, anthrax, aspergillosis, bacteremia, bacterial skin diseases, *bartonella* infections, botulism, brucellosis, *burkholderia* infections, *campylobacter* infections, candidiasis, cat-scratch disease, chlamydia infections, cholera, *clostridium* infections, coccidioidomycosis, cryptococcosis, dermatomycoses, diphtheria, ehrlichiosis, epidemic louse borne typhus, *Escherichia coli* infections, *fusobacterium* infections, gangrene, general infections, general mycoses, gonorrhea, gram-negative bacterial infections, gram-positive bacterial infections, histoplasmosis, impetigo, *klebsiella* infections, legionellosis, leprosy, leptospirosis, *listeria* infections, lyme disease, malaria, *maduromycosis*, melioidosis, mycobacterium infections, mycoplasma infections, necrotizing fasciitis, *nocardia* infections, onychomycosis, ornithosis, pneumococcal infections, pneumonia, pseudomonas infections, Q fever, rat-bite fever, relapsing fever, rheumatic fever, *rickettsia* infections, Rocky-mountain spotted fever, *salmonella* infections, scarlet fever, scrub typhus, sepsis, sexually transmitted bacterial diseases, staphylococcal infections, streptococcal infections, surgical site infection, tetanus, tick-borne diseases, tuberculosis, tularemia, typhoid fever, urinary tract infection, *vibrio* infections, yaws, *yersinia* infections, *Yersinia pestis* plague, zoonoses and zygomycosis.

The polymers of the present embodiments can therefore be used to treat medical conditions caused by pathogenic microorganisms by virtue of their anti-microbial effects inflicted upon the pathogenic microorganisms by one of the above-mentioned mechanism which mostly stem from their specific and selective affinity to the membrane of the pathogenic microorganism, and relative undamaging effect they have on mammalian cell, as demonstrated for red blood cells and presented in the Examples section that follows. This affinity can be used to weaken, disrupt, puncture, melt, fuse and/or mark the membrane of a pathogenic microorganism.

The pathogenic microorganism may be destroyed directly by the disruption of its membrane as demonstrated and presented for a series of bacterial strains in the Examples section that follows, or be weakened so as to allow the innate immune system to destroy it or slow down its metabolism and therefore its reproduction so as to allow the innate immune system to overcome the infection.

The pathogenic microorganism may be destroyed by the disruption of its membrane so as to allow a therapeutically active agent, such as an antibiotic agent, to more easily penetrate the cell of the microorganism and afflict its activity thereon.

The latter capacity of the antimicrobial polymer of the present invention to assist the penetration of another therapeutically active agent into the cells of the pathogenic microorganism can be utilized to treat many infectious diseases, such as, for example, malaria.

Malaria, also called jungle fever, paludism and swamp fever, is an infectious disease characterized by cycles of chills, fever, and sweating, caused by the parasitic infection of red blood cells by the protozoan parasite, *Plasmodium* (one of the *Apicomplexa*), which is transmitted by the bite of an infected vector for human malarial parasite, a female *Anopheles* mosquito. Of the four types of malaria, the most life-threatening type is *falciparum* malaria. The other three types of malaria, vivax, malariae, and ovale, are generally less serious and are not life-threatening. Malaria, the deadliest infectious disease yet to be beaten, causes about half a billion infections and between one and two millions deaths annually, mainly in the tropics and sub-Saharan Africa. The *Plasmodium falciparum* variety of the parasite accounts for 80% of cases and 90% of deaths. The stickiness of the red blood cells is particularly pronounced in *P. falciparum* malaria and this is the main factor giving rise to hemorrhagic complications of malaria.

To date there is no absolute cure for malaria. If diagnosed early, malaria can be alleviated, but prevention still more effective than treatment, thus substances that inhibit the parasite are widely used by visitors to the tropics. Since the $17^{th}$ century quinine has been the prophylactic of choice for malaria. The development of quinacrine, chloroquine, and primaquine in the $20^{th}$ century reduced the reliance on quinine. These anti-malarial medications can be taken preventively, which is recommended for travelers to affected regions.

Unfortunately as early as the 1960s several strains of the malarial parasite developed resistance to chloroquine. This development of resistance, plus the growing immunity of mosquitoes to insecticides, has caused malaria to become one the of world's leading re-emerging infectious diseases. Mefloquine may be used in areas where the disease has become highly resistant to chloroquine, but some strains are now resistant to it and other drugs. Artemisinin (derived from sweet wormwood) in combination with other drugs is now in many cases the preferred treat for resistant strains. Malarone (atovaquone and proguanil) is also used for resistant strains. Vaccines against malaria are still experimental.

While reducing the present invention to practice, the present inventors have prepared and successfully used these anti-microbial polymers as anti-malarial agents with reduced hemolysis effect as demonstrated in the Examples section that follows. It is shown that the polymers of the present invention were able to kill the parasite in a manner that is clearly dissociated from lysis of the host cell. These polymers were able to enter the infected cell but to selectively permeabilize the parasite cell membrane. These results are best explained by the differential interaction of the peptides-like polymer with the distinct properties of the structure and composition of the membranes of intra-erythrocytic malaria parasite *Plasmodium falciparum* as compared to those of the host and normal red blood cells. These findings also established that the membrane active polymers of the present invention could be engineered to act specifically on the membrane of the intracellular parasite to perturb its functions. The polymers of the present invention can therefore overcome the problem of parasitic resistance to various anti-malarial agents by, for example, weakening the parasite's membrane and enabling the anti-malarial agents to penetrate the parasite's membrane more rapidly.

Therefore, a preferred embodiment of the present invention is the use of the antimicrobial polymers as an anti-malarial agent, either per-se or in combination with a presently used anti-malarial agent or any other anti-parasitic agent, as exemplified in the Examples section that follows.

The antimicrobial polymers of the present invention can be utilized either per se, or as an active ingredient of a pharmaceutical composition, with or without an additional therapeutically active agent, and a pharmaceutically acceptable carrier.

Hence, according to still another aspect of the present invention, there are provided pharmaceutical compositions, which comprise one or more of the polymers of the present invention as described above having an antimicrobial activity and a pharmaceutically acceptable carrier.

As used herein a "pharmaceutical composition" refers to a preparation of the antimicrobial polymer described herein, with other chemical components such as pharmaceutically acceptable and suitable carriers and excipients. The purpose of a pharmaceutical composition is to facilitate administration of a compound to an organism.

Hereinafter, the term "pharmaceutically acceptable carrier" refers to a carrier or a diluent that does not cause significant irritation to an organism and does not abrogate the biological activity and properties of the administered compound. Examples, without limitations, of carriers are: propylene glycol, saline, emulsions and mixtures of organic solvents with water, as well as solid (e.g., powdered) and gaseous carriers.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

Pharmaceutical compositions for use in accordance with the present invention thus may be formulated in conventional manner using one or more pharmaceutically acceptable carriers comprising excipients and auxiliaries, which facilitate processing of the silver-coated enzymes into preparations which, can be used pharmaceutically. Proper formulation is dependent upon the route of administration chosen. Toxicity and therapeutic efficacy of the silver-coated enzymes described herein can be determined by standard pharmaceutical procedures in experimental animals, e.g., by determining the $EC_{50}$, the $IC_{50}$ and the $LD_{50}$ (lethal dose causing death in 50% of the tested animals) for a subject silver-coated enzyme. The data obtained from these activity assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. (See e.g., Fingl et al., 1975, in "The Pharmacological Basis of Therapeutics", Ch. 1 p. 1).

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA (the U.S. Food and Drug Administration) approved kit, which may contain one or more unit dosage forms containing the active ingredient. The pack may, for example, comprise metal or plastic foil, such as, but not limited to a blister pack or a pressurized container (for inhalation). The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions for human or veterinary administration. Such notice, for example, may be of labeling approved by the U.S. Food and Drug Administration for prescription drugs or of an approved product insert. Compositions comprising a silver-coated enzyme of the invention formulated in a compatible pharmaceutical carrier may also be prepared, placed in an appropriate container, and labeled for treatment of an indicated condition or diagnosis, as is detailed hereinabove.

Thus, according to an embodiment of the present invention, depending on the selected polymers and the presence of additional active ingredients, the pharmaceutical compositions of the present invention are packaged in a packaging material and identified in print, in or on the packaging material, for use in the treatment of a medical condition associated with a pathogenic microorganism, as is defined hereinabove and a parasite.

The pharmaceutical composition comprising a polymer of the present invention may further comprise at least one additional therapeutically active agent, as this is defined and presented hereinabove.

The polymers of the present invention can be further beneficially utilized as active substances in various medical devices.

Hence, according to an additional aspect of the present invention there is provided a medical device which includes one or more of the polymers of the present invention, described hereinabove, and a delivery system configured for delivering the polymer(s) to a bodily site of a subject.

The medical devices according to the present invention are therefore used for delivering to or applying on a desired bodily site the polymers of the present invention. The polymers can be incorporated in the medical devices either per se or as a part of a pharmaceutical composition, as described hereinabove.

As used herein, the phrase "bodily site" includes any organ, tissue, membrane, cavity, blood vessel, tract, biological surface or muscle, which delivering thereto or applying thereon the polymers of the present invention is beneficial.

Exemplary bodily sites include, but are not limited to, the skin, a dermal layer, the scalp, an eye, an ear, a mouth, a throat, a stomach, a small intestines tissue, a large intestines tissue, a kidney, a pancreas, a liver, the digestive system, the respiratory tract, a bone marrow tissue, a mucosal membrane, a nasal membrane, the blood system, a blood vessel, a muscle, a pulmonary cavity, an artery, a vein, a capillary, a heart, a heart cavity, a male or female reproductive organ and any visceral organ or cavity.

The medical device acording to this aspect of the present invention can be any medical device known in the art, including those defined and classified, for example, by the Food and Drug Administration (FDA), e.g., Class I, II and III, depending e.g., on the condition and bodily site being treated.

Thus, for example, in one embodiment of this aspect of the present invention, the medical device comprises a delivery system that is configured to deliver the polymer(s) by inhalation. Such inhalation devices are useful for delivering the polymers of the present invention to, e.g., the respiratory tract.

The delivery system in such medical devices may be based on any of various suitable types of respiratory delivery systems which are suitable for administering a therapeutically effective dose of the polymer(s) of the present invention to a subject. The inhalation device may be configured to deliver to the respiratory tract of the subject, preferably via the oral and/or nasal route, the compound in the form of an aerosol/spray, a vapor and/or a dry powder mist. Numerous respiratory systems and methods of incorporating therapeutic agents therein, such as the polymers of the present invention, suitable for assembly of a suitable inhalation device are widely employed by the ordinarily skilled artisan and are extensively described in the literature of the art (see, for example to U.S. Pat. Nos. 6,566,324, 6,571,790, 6,637,430, and 6,652,323; U.S. Food & Drug Administration (USFDA) Center For Drug Evaluation and Research (CDER); "The Mechanics of Inhaled Pharmaceutical Aerosols; An Introduction", by W. H. Finlay, Academic Press, 2001; and "Inhalation Aerosols"edited by A. J. Hickey, Marcel Dekker, New York, 1996).

The respiratory delivery system may thus be, for example, an atomizer or aerosol generator such as a nebulizer inhaler, a dry powder inhaler (DPI) and a metered dose inhaler (MDI), an evaporator such as an electric warmer and a vaporizer, and a respirator such as a breathing machine, a body respirator (e.g., cuirass), a lung ventilator and a resuscitator.

In still another embodiment of this aspect of the present invention, the medical device is such that delivering the polymer(s) is effected transdermally. In this embodiment, the medical device is applied on the skin of a subject, so as to transdermally deliver the polymer(s) to the blood system.

Exemplary medical devices for transdermally delivering a polymer according to the present invention include, without limitation, an adhesive plaster and a skin patch. Medical devices for transdermal or transcutaneous delivery of the polymer(s) typically further include one or more penetration enhancers, for facilitating their penetration through the epidermis and into the system.

According to another embodiment of this aspect of the present invention, the medical device is such that delivering the polymer(s) is effected by topically applying the medical device on a biological surface of a subject. The biological surface can be, for example, a skin, scalp, an eye, an ear and a nail. Such medical devices can be used in the treatment of various skin conditions and injuries, eye and ear infections and the like.

Exemplary medical devices for topical application include, without limitation, an adhesive strip, a bandage, an adhesive plaster, a wound dressing and a skin patch.

In another embodiment of this aspect of the present invention, the medical device is such that delivering the polymer(s) is effected by implanting the medical device in a bodily organ. As used herein, the term "organ" further encompasses a bodily cavity.

The organ can be, for example, a pulmonary cavity, a heart or heart cavity, a bodily cavity, an organ cavity, a blood vessel, an artery, a vein, a muscle, a bone, a kidney, a capillary, the space between dermal layers, an organ of the female or male reproductive system, an organ of the digestive tract and any other visceral organ.

The medical device according to this embodiment of the present invention typically includes a device structure in which a polymer according to the present invention is incorporated. The polymer(s) can thus be, for example, applied on, entrapped in or attached to (chemically, electrostatically or otherwise) the device structure.

The device structure can be, for example, metallic structure and thus may be comprised of a biocompatible metal or mixture of metals (e.g., gold, platinum).

Alternatively, the device structure may be comprised of other biocompatible matrices. These can include, for example, plastics, silicon, polymers, resins, and may include at least one component such as, for example, polyurethane, cellulose ester, polyethylene glycol, polyvinyl acetate, dextran, gelatin, collagen, elastin, laminin, fibronectin, vitronectin, heparin, segmented polyurethane-urea/heparin, poly-L-lactic acid, fibrin, cellulose and amorphous or structured carbon such as in fullerenes, and any combination thereof.

In cases where a biodegradable implantable device is desired, the device structure can be comprised of a biocompatible matrix that is biodegradable. Biodegradable matrices can include, for example, biodegradable polymers such as poly-L-lactic acid.

Optionally, the device structure may be comprised of biocompatible metal(s) coated with other biocompatible matrix.

Further optionally, in cases where a device which releases the polymer(s) of the present invention in a controlled manner is desired, the device structure can be comprised of or coated with a biocompatible matrix that functions as or comprises a slow release carrier. The biocompatible matrix can therefore be a slow release carrier which is dissolved, melted or liquefied upon implantation in the desired site or organ. Alternatively, the biocompatible matrix can be a pre-determined porous material which entraps the polymer(s) in the pores. When implanted in a desired site, the polymer(s) diffuse out of the pores, whereby the diffusion rate is determined by the pores size and chemical nature. Further alternatively, the biocompatible matrix can comprise a biodegradable matrix, which upon degradation releases the polymer(s) of the present invention.

The polymer(s) of the present invention can be incorporated in the device structure by any methodology known in the art, depending on the selected nature of the device structure. For example, the polymer(s) can be entrapped within a porous matrix, swelled or soaked within a matrix, or being adhered to a matrix.

Much like their antimicrobial activity in the body, the antimicrobial activity of the polymers of the present invention may further be harnessed for the preservation of food ingredients and products.

Hence, according to yet another aspect of the present invention there is provided a food preservative comprising an effective amount of the polymer of the present invention as described herein.

The polymer(s) may be incorporated into the food product as one of its ingredients either per se, or with an edible carrier.

The polymers of the present invention have been shown to have high and selecting affinity towards membranes of microorganisms as demonstrated in the Examples section that follows. This attribute is one of the main elements which contributes to the effective and efficacious activity of the polymers when utilized as an antimicrobial agent. When the polymer is coupled with a labeling agent, this membrane binding attribute can be further employed to label colonies and proliferation sites of microorganisms, especially microbial growth loci in a host in vivo.

Hence, according to another aspect of the present invention there is provided an imaging probe for detecting a pathogenic microorganism, the imaging probe comprising a polymer as defined and described hereinabove, whereas the polymer further includes at least one labeling agent, as defined hereinabove, attached thereto. When released to the environment, these polymers, having a labeling agent attached thereto will bind to the membrane of cell of microorganisms and therefore attach the labeling agent to the cells of the microorganism.

As used herein, the term "chromophore" refers to a chemical moiety that, when attached to another molecule, renders the latter colored and thus visible when various spectrophotometric measurements are applied.

The phrase "fluorescent compound" refers to a compound that emits light at a specific wavelength during exposure to radiation from an external source.

The phrase "phosphorescent compound" refers to a compound emitting light without appreciable heat or external excitation as by slow oxidation of phosphorous.

A heavy metal cluster can be for example a cluster of gold atoms used, for example, for labeling in electron microscopy techniques.

According to preferred embodiments of the present invention, one or more labeling agents may be attached to the polymer at any substitutable position, as in the case of an active agent discussed above. Examples of such substitutable positions are, without limitation, a side chain of any one or more of the amino acid residues in the polymer, any one of the linking moieties of the polymer, any one of the N- and C-termini of the polymer and any one or more of the hydrophobic moiety residues in the polymer.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions; illustrate the invention in a non limiting fashion.

Materials and Experimental Methods

Materials:

Lysine having Fmoc ((9H-fluoren-9-yl)methyl carbonate) protection on its main-chain amine group and Boc (tert-butyl carbonate) protection on its side-chain amine group was purchased from Applied Biosystems and from NovaBiochem.

ω-amino fatty acids such as 4-amino-butiric acid, 8-amino-caprylic acid and 12-animo-lauric acid having Fmoc protection of the amine group were purchased from Sigma-Aldrich/NovaBiochem.

All other solvents and reagents used were purchased from Sigma-Aldrich/NovaBiochem/Applied Biosystems/J. T. Baker and were used without further purification.

Preparation of Libraries of Antimicrobial Polymers—General Procedure:

The polymers according to the present invention were prepared by a solid phase method and were purified to chromatographic homogeneity according to methodologies described in the art (Feder, R. et al. (2000) *J. Biol. Chem.* 275, 4230-4238). Briefly, the polymers were synthesized by applying the Fmoc active ester chemistry on a fully automated, programmable peptide synthesizer (Applied Biosystems 433A). After cleavage from the resin, the crude polymers were extracted with 30% acetonitrile in water and purified to obtain a chromatographic homogeneity greater than 95%, as determined by HPLC (Alliance Waters).

HPLC chromatograms were performed on C18 columns (Vydak, 250 mm×4.6 or 10 mm) using a linear gradient of acetonitrile in water (1% per minute), both solvents contained 0.1% trifluoroacetic acid. The purified polymers were subjected to mass spectrometry (ZQ Waters) to confirm their composition and stored as a lyophilized powder at −20° C. Prior to being tested, fresh solutions were prepared in water, mixed by vortex, solubilized by ultrasound, centrifuged and then diluted in the appropriate medium.

In order to estimate the hydrophobicity of each polymer, the polymer was eluted with a linear gradient of acetonitrile (1% per minute) on an HPLC reversed-phase C18 column, and the percent of acetonitrile at which the polymer was eluted was used for hydrophobicity estimation (see, "ACN (%)" in Table 3 below).

Exemplary building units which were utilized in the synthesis described above are presented in Scheme I below and include: lysine and an ω-amino-fatty acid having m carbon atoms (Compound I).

Synthesis of exemplary polymers according to the present invention, which are comprised of lysine and Compound I, was performed by adding an Fmoc/Boc-protected lysine and an Fmoc-protected Compound I separately and sequentially to the resin according to conventional peptide solid phase synthesis protocols.

Scheme 1

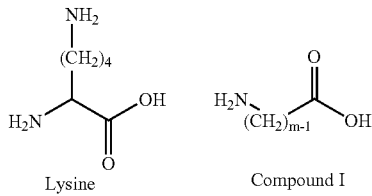

Lysine                Compound I

Bacterial Strains and Sample Preparation:

Antibacterial activity was determined using the following strains, cultured in LB medium (10 grams/liter trypton, 5 grams/liter yeast extract, 5 grams/liter NaCl, pH 7.4): *Escherichia coli* (ATCC 35218); methicilin resistant *Staphylococcus aureus* (CI 15903); *Bacillus cereus* (ATCC 11778); and *Pseudomonas aeruginosa* (ATCC 9027).

Minimal Inhibitory Concentration (MIC) Measurements:

Minimal inhibitory concentrations (MICs) were determined by microdilution susceptibility testing in 96-well plates using inocula of $10^6$ bacteria per ml. Cell populations were evaluated by optical density measurements at 600 nm and were calibrated against a set of standards. Hundred (100) µl of a bacterial suspension were added to 100 µl of culture medium (control) or to 100 µl of culture medium containing various polymer concentrations in 2-fold serial dilutions. Inhibition of proliferation was determined by optical density measurements after an incubation period of 24 hours at 37° C.

The Effect of Physical Parameters (Charge and Hydrophobicity) on Antimicrobial Activity:

A library of polymers was prepared to sample the effect of increased charge and hydrophobicity on the antimicrobial activity. The charge was serially sampled by increasing the number of the ω-amino-fatty acid-lysine conjugates from 1 to 7. The hydrophobicity was serially sampled by increasing the number of the carbon atoms of the ω-amino fatty acid (4, 8 and 12). The polymers in each series were tested for their antimicrobial activity, as described hereinabove.

Development of Antimicrobial-Resistance in Bacteria:

The possible development of resistance to the antimicrobial activity of the polymers of the present invention by bacteria, as compared with known resistance-inducing classical antibiotic agents, gentamicin, tetracycline and ciprofloxacin, which served as controls for the development of antibiotic-resistant bacterial strains, was studied. Bacteria samples at the exponential phase of growth were exposed to an antimicrobial agent for MIC determination as described above. Following incubation overnight, bacteria were harvested from wells that displayed near 50% growth inhibition, washed and diluted in fresh medium, grown overnight, and subjected again to MIC determination for up to 10 iterations. In parallel, MIC evolution in these subcultures was compared concomitantly with each new generation, using bacteria harvested from control wells (wells cultured without a polymer) from the previous generation. The relative MIC was calculated for each experiment from the ratio of MIC obtained for a given subculture to that obtained for first-time exposure.

Kinetic Studies:

The kinetic assays were performed in test tubes, in a final volume of 1 ml, as follows: 100 µl of a suspension containing bacteria at $2\text{-}4\times10^7$ colony forming units (CFUs)/ml in culture medium were added to 0.9 ml of culture medium or culture medium containing various polymer concentrations (0, 3 and 6 multiples of the MIC value). After 0, 30, 60, 90, 120 and 360 minutes of exposure to the polymer at 37° C. while shaking, cultures were subjected to serial 10-fold dilutions (up to $10^{-6}$) by adding 50 µl of sample to 450 µl saline (0.9% NaCl). Colony forming units (CFUs) were determined using the drop plate method (3 drops, 20 µl each, onto LB-agar plates, as described in Yaron, S. et al (2003), *Peptides* 24, 1815-1821). CFUs were counted after plate incubation for 16-24 hours at 37° C. Statistical data for each of these experiments were obtained from at least two independent assays performed in duplicates.

Antimicrobial Activity at Enhanced Outer-Membrane Permeability Conditions:

The outer membrane permeability of gram-negative bacteria, namely *E. coli* or *P. aeruginosa*, was enhanced by treating bacterial cultures with EDTA (ethylenediaminetetraacetic acid) according to the following procedure: 1 M EDTA solution in water (pH=8.3) was diluted in LB medium to obtain a 4 mM concentration and the diluted solution was used for polymer dissolution. Bacteria were grown overnight in LB medium, and 100 µl fractions containing $10^6$ bacteria per ml were added to 100 µl of EDTA culture medium or to EDTA culture medium containing various polymer concentrations (2-fold serial dilutions) in 96-well plates. Growth inhibition was determined against gram-negative bacteria as described above.

Susceptibility to plasma proteases:

The susceptibility of the polymers of the present invention to proteolytic digestion was assessed by determining the antibacterial activity after exposure to human plasma as follows: 250 µl of polymer solutions in saline (0.9 % NaCl) at a concentration of 16 multiples of the MIC value were pre-incubated with 50 % (v/v) human plasma in culture medium at 37 ° C. After incubation periods of 3, 6, and 18 hours, the polymer solutions were subjected to 2-fold serial dilutions in LB medium in 96-well plates. The susceptibility of the polymers of the present invention to enzymatic cleavage was assessed by pre-incubating four exemplary polymers according to the present invention, $C_{12}K(NC_8K)_5NH_2$ (SEQ ID NO: 43), $K(NC_{12}K)_3NH_2$ (SEQ ID NO: 60), $C_{12}KNC_2KNH_2$ (SEQ ID NO: 54), and $C_{12}KKNC_{12}KNH_2$ (SEQ ID NO: 78), and a 16-residues dermaseptin S4 derivative (SEQ ID NO: 98) (S4$_{16}$, an exemplary AMP which served as the control), in human plasma (50 %) for various time periods. The antibacterial activity was thereafter determined against E. coli and S. aureus, as described above. In parallel, antibacterial activity was also determined in culture medium conditions in the absence of plasma (referred to as 0 hours of pre-incubation in the experimental results section below). Statistical data was obtained from at least two independent experiments performed in duplicates.

Hemolysis Assays:

The polymer's membranolytic potential was determined against human red blood cells (RBC) in phosphate buffer solution (PBS). Human blood samples were rinsed three times in PBS by centrifugation for 2 minutes at 200×g, and re-suspended in PBS at 5% hematocrite. A 50 µl-fractions of a suspension containing 2.5×10$^8$ RBC were added to test tubes containing 200 µl of polymer solutions (2-fold serial dilutions in PBS), PBS alone (for base-line values), or distilled water (for 100% hemolysis). After 3 hours incubation at 37° C. under agitation, samples were centrifuged, and hemolytic activity was determined as a function of hemoglobin leakage by measuring absorbance at 405 nm of 200 µl aliquots of the supernatants.

Circular dichroism (CD):

CD spectra in millidegrees were measured with an Aviv model 202 CD spectrometer (Aviv Associates, Lakewood, NJ) using a 0.01 cm rectangular QS Heilma cuvette at 25° C. (controlled by thermoelectric Peltier elements with an accuracy of 0.1° C.). Polymer samples were dissolved in either PBS, 20 % (v/v) trifluoroethanol/water or titrated in PBS containing POPC (2-oleoyl- 1 -palmitoyl-sn- glycero-3-phosphocholine) and POPG (1palmitoyl-2-oleoyl-sn-glycero-3-phospho- rac-(1-glycerol)) in a 3:1 ratio and concentration of up to 2 mM, to thereby obtain liposomes. CD spectra of the polymers were scanned at a concentration of 100 µM as determined by UV using standard curves of known concentrations for each polymer. The CD of the N-terminus acylated S4 dermaseptin derivative NC$_{12}$K$_4$S4(1-14) (SEQ ID NO: 97) (Mor, A. et al. (1994), J. Biol. Chem. 269(50): 31635-41), an exemplary AMP, was measured under the same conditions and was used as a reference compound in the CD studies. The CD data presented herein represent an average of three separate recordings values.

Surface Plasmon Resonance Assay:

Binding to model bilayer membranes was studied by surface plasmon resonance (SPR) using a BIAcore 2000 biosensor system. Liposomes composed of phospholipids mimicking bacterial plasma membrane (POPC:POPG in a 3:1 ratio) were immobilized on the sensor surface and polymer solutions were continuously flowed over the membrane. The curve of resonance signal as a function of time displays the progress of the interaction between the analyzed polymer and the immobilized phospholipid membrane. The affinity of the interaction was calculated from analysis of the resulting curves as detailed in Gaidukov, L. et al. (2003), *Biochemistry* 42, 12866-12874. Briefly, the association and dissociation curves (binding rates) were analyzed at five doses (0.21, 0.42, 0.84, 1.67, 3.35 □g), and the K$_{app}$ (the resulting binding constant) was calculated assuming a 2-step model).

Lipopolysaccharide Binding Assay:

In order to explore the mechanism by which the polymers of the present invention exert the anti-bacterial activity, the targeting of the polymers to the bacterial membrane was tested. More specifically, the binding affinity of the positively charged polymers to the negatively charged lipopolysaccharides (LPS) present on the membrane of gram-negative bacteria was tested.

Thus, binding assays of the polymers of the present invention to LPS were carried out with SPR technology using the optical biosensor system BIAcore 2000 (BIAcore). A mixture of 50 □M of the polymer samples in PBS and 100 □g/ml LPS was incubated for 30 minutes at room temperature. The binding assay was performed by injecting 10 □l of the mixture at a flow rate of 10 □l per minute at 25° C. over a POPC:POPG (3:1) bilayer spread on an L1 sensor chip. 100 µg/ml LPS without a polymer sample were injected as a blank of LPS binding to the membrane and 50 µM of a polymer sample was injected to determine the polymer binding to membrane without LPS.

DNA Binding Assay:

Binding of the polymers of the present invention to nucleic acids was studied by assessing their ability to retard migration of DNA plasmids during gel electrophoresis in a 1% agarose gel. DNA-retardation experiments were performed by mixing 200 nanograms of the plasmid DNA (pUC19, 2683 base pairs) with increasing amounts of various polymers in a final volume of 20 µl doubly distilled water (DDW). The reaction mixtures were incubated at room temperature for 30 minutes. Subsequently, 2 µl of loading dye (20% Ficoll 400, 0.1 M EDTA, 0.25% bromophenol blue and 1% sodium dodecyl sulfate) were added and an aliquot of 20 µl was applied to 1% agarose gel electrophoresis in TAE buffer (0.02 M Tris base, 0.01 M glacial acetic acid, 0.5 mM EDTA, pH=8.5) containing ethidium bromide (0.25 µg/ml). The plasmid used in this experiment was isolated by the Wizard® Plus SV Minipreps DNA Purification System (Promega).

Saliva microbicidal assays:

Antimicrobial activity of polymers of the present invention against the melange of microorganisms in the saliva of healthy human volunteers was studied by mixing fresh human saliva with the polymers or IB-367 (SEQ ID NO: 96) (both dissolved in 10 mM sodium acetate buffer set at pH 5 to a final concentration of 100 µM) at a 1:1 ratio. A solution of the saliva with no anti-bacterial agent served as a control. IB-367 is a positively charged protegrin peptide with known in-vitro and in-vivo activities against the microflora associated with human oral mucositis (Loury, D. et al., 1999, Oral Surg Oral Med Oral Pathol Oral Radiol Endod 87(5): 544-51.). Each of the solutions was spread over a LA plate, and the plated saliva samples were incubated overnight at 37° C. without aeration. The colonies were enumerated and counted to determine the microbicidal effect of the drug. The values of viable colony forming units (CFU) were determined as described above.

Anti-Malarial Assays:

The investigation of the anti-malarial activity of the polymers of the present invention was performed by screening part of the library of the polymers presented hereinbelow in Table 3, for anti-malarial and hemolytic activities as well as for their toxic activities against mammalian cells in culture.

Parasite cultivation: Different strains of *P. falciparum* were cultivated as described by Kutner and co workers [Kutner, S., Breuer, W. V., Ginsburg, H., Aley, S. B., and Cabantchik, Z. I. (1985) *J. Cell. Physiol.* 125, 521-527] using human red blood cells (RBC). The cultures were synchronized by the sorbitol method [Lambros, C. J., and Vanderberg, J. P. (1979) *J. Parasitol.* 65, 418-420] and infected cells were enriched from culture by Percoll-alanine gradient centrifugation [Kutner, S., Breuer, W. V., Ginsburg, H., Aley, S. B., and Cabantchik, Z. I. (1985) *J. Cell. Physiol.* 125, 521-527].

Determination of IC$_{50}$: Synchronized cultures at the ring stage were cultured at 1% hematocrit and 2% parasitemia in the presence of increasing concentrations of the tested polymers. After 18 hours of incubation parasite viability was determined by [$^3$H]hypoxanthine (Hx) uptake (final concentration was 2 μCi/ml) during 6 hours and compared to controls (without the polymers). The 50% inhibitory concentration (IC$_{50}$) was determined by nonlinear regression fitting of the data using the commercially available software suite Sigmaplot™.

Time- and stage-dependence action of the polymers: Antimalarial drugs are known to exert their action differentially on different stages of parasite development. They also need a minimal time of interaction with the parasite in order to inhibit its growth. Therefore, cultures at the ring stage were seeded in 24-well plate at 1% hematocrit, 2% parasitemia in plate medium (growth medium without hypoxanthine, 10 mM NaHCO3 and 7% heat inactivated human plasma). Tested polymers were added at different concentrations immediately and removed after 6, 24 and 48 hours. Cultures without polymers were left to mature to the trophozoite stage and dosed with compounds for 6 and 24 hours. Two μCi of Hx per well were added to all cells after 30 hours from the onset of the experiment and the cells were harvested after 24 hours.

Effect of the polymers on mammalian cells in culture: MDCK (cell line from dog kidney) epithelial cells were grown to confluence (about 3 days in culture). Parallel cultures were grown with different concentrations of the tested polymers. Thereafter 10 μl of Alamar blue was added and fluorescence was measured after 3.5 hours. For a positive control, 10 μM of cycloheximide were added to control samples at the beginning of cultivation.

Experimental Results

Preparation of Libraries of Polymers:

Several representative series of polymers according to the present invention, which are substantially comprised of a plurality of lysine residues and ω-amino-fatty acid residues and fatty acid residues as hydrophobic moieties, were prepared according to the general procedure described above, and are presented in Table 3 below.

These exemplary polymers are referred to in this section according to the following formula:

T[NC$_i$K]$_j$G

In this formula, NC$_i$ denotes an ω-amino-fatty acid residue (an exemplary hydrophobic moiety according to the present invention, represented by D$_1$ ... Dn in the general formula I described herein), whereby i denotes the number of carbon atoms in the fatty acid residue; K denotes a lysine residue (an exemplary amino acid residue according to the present invention, denoted as A$_1$ ... An in the general Formula I described herein, such that [NC$_i$K] denotes a residue of an ω-amino-fatty acid-lysine conjugate (denoted as [A$_1$-Z$_1$-D$_1$] ... [An-Zn-Dn] in the general Formula I described herein); j denotes the number of the repeating units of a specific conjugate in the polymer (corresponding to n in the general Formula I described herein); and T and G each independently denotes either a hydrogen (no denotation), a lysine residue (denoted K), an ω-amino-fatty acid residue (denoted NC$_i$), a fatty acid residue (denoted C$_i$), an ω-amino-fatty acid-lysine-conjugate residue (denoted NC$_i$K), an fluorenylmethyloxycarbonyl residue (denoted Fmoc), a benzyl residue (denoted Bz), a cholate residue (denoted Chl), an amine group (typically forming an amide at the C-terminus and denoted NH$_2$), a free acid residue (for the C-terminus no denotation), an alcohol residue and any combination thereof (all corresponding to X and Y in the general formula I described herein).

Thus, for example, a polymer according to the present invention which is referred to herein as NC$_{12}$K(NC$_8$K)$_7$NH$_2$ (SEQ ID NO: 52), corresponds to a polymer having the general formula I described hereinabove, wherein: X is a residue of a conjugate of an ω-amino-fatty acid having 12 carbon atoms (12-amino-lauric acid) and lysine; n is 6; A$_1$...A$_6$ are each a lysine residue; D$_1$...D$_7$ are all residues of an ω-amino-fatty acid having 8 carbon atoms (8-amino-caprylic acid); Z$_1$...Z$_7$ and W$_0$-W$_7$ are all peptide bonds; and Y is an amine. For clarity, the chemical structure of NC$_{12}$K(NC$_8$K)$_7$NH$_2$ (SEQ ID NO: 52) is presented in Scheme 2 below:

Scheme 2

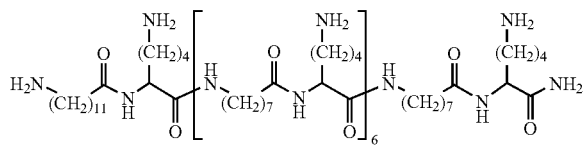

Minimal Inhibitory Concentration Measurements:

The polymers in each series were tested for various antimicrobial activities, as described hereinabove. The obtained results are presented in Table 3 below, wherein:

"Q" represents the overall molecular charge at physiological pH (column 3 in Table 3);

"ACN (%)" represents the percent of acetonitrile in the HPLC-RP gradient mobile phase at which the polymer was eluted and which corresponds to the estimated hydrophobicity of the polymer (column 4 in Table 3);

"LC50" represents the lytic concentration of each tested polymer in □M obtained by the membranolytic potential determination experiment of hemolysis of human red blood cells measured as described hereinabove (column 5 in Table 3);

"MIC E.c." represents the minimal inhibitory concentration of each tested polymer in □M for *E. coli*, measured as described hereinabove in the antibacterial activity assay (column 6 in Table 3);

"MIC EDTA E.c." represents the minimal inhibitory concentration of each tested polymer in □M for *E. coli* culture in the presence of 2 mM EDTA, measured as described hereinabove for the enhanced outer-membrane permeability assay (column 7 in Table 3);

"MIC P.a." represents the minimal inhibitory concentration of each tested polymer in □M for *P. aeruginosa*, measured as described hereinabove for the antibacterial activity assay (column 8 in Table 3);

"MIC MR S.a." represents the minimal inhibitory concentration of each tested polymer in □M for methicilin-resistant *S. aureus*, measured as described hereinabove for the antibacterial activity assay of antibiotic-resistant bacteria (column 9 in Table 3);

"MIC B.c." represents the minimal inhibitory concentration of each tested polymer in □M for *Bacillus cereus*, measured as described hereinabove for the antibacterial activity assay (column 10 in Table 3); and ND denotes "not determined".

Some values are presented with ±standard deviations from the mean.

"Orn" and "Arg" in entries 84 and 85 denote ornithine and arginine amino acid residues respectively.

TABLE 3

| SEQ ID NO: | Polymer | Q | ACN (%) | LC50 | MIC E.c. | MIC EDTA E.c. | MIC P.a. | MIC MR S.a. | MIC B.c. |
|---|---|---|---|---|---|---|---|---|---|
| 1 | $C_4KNC_4KNH_2$ | 2 | 19.6 | ND | >50 | ND | >50 | >50 | >50 |
| 2 | $C_4K(NC_4K)_2NH_2$ | 3 | 21.8 | ND | >50 | ND | >50 | >50 | >50 |
| 3 | $C_4K(NC_4K)_3NH_2$ | 4 | 21.5 | ND | >50 | ND | >50 | >50 | >50 |
| 4 | $C_4K(NC_4K)_4NH_2$ | 5 | 22 | ND | >50 | ND | >50 | >50 | >50 |
| 5 | $C_4K(NC_4K)_5NH_2$ | 6 | 22.9 | ND | >50 | ND | >50 | >50 | >50 |
| 6 | $C_4K(NC_4K)_6NH_2$ | 7 | 23.5 | ND | >50 | ND | >50 | >50 | >50 |
| 7 | $C_4K(NC_4K)_7NH_2$ | 8 | 24.3 | ND | >50 | ND | >50 | >50 | >50 |
| 8 | $KNC_4KNH_2$ | 3 | 0 | ND | >50 | ND | >50 | >50 | >50 |
| 9 | $K(NC_4K)_2NH_2$ | 4 | 9 | ND | >50 | ND | >50 | >50 | >50 |
| 10 | $K(NC_4K)_3NH_2$ | 5 | 18.8 | ND | >50 | ND | >50 | >50 | >50 |
| 11 | $K(NC_4K)_4NH_2$ | 6 | 20.1 | ND | >50 | ND | >50 | >50 | >50 |
| 12 | $K(NC_4K)_5NH_2$ | 7 | 20.8 | ND | >50 | ND | >50 | >50 | >50 |
| 13 | $K(NC_4K)_6NH_2$ | 8 | 21.7 | ND | >50 | ND | >50 | >50 | >50 |
| 14 | $K(NC_4K)_7NH_2$ | 9 | 22.2 | ND | >50 | ND | >50 | >50 | >50 |
| 15 | $C_{12}K(NC_4K)_1NH_2$ | 2 | 50.2 | ND | >50 | ND | >50 | >50 | >50 |
| 16 | $C_{12}K(NC_4K)_2NH_2$ | 3 | 47.6 | ND | >50 | ND | >50 | >50 | >50 |
| 17 | $C_{12}K(NC_4K)_3NH_2$ | 4 | 46.4 | ND | >50 | ND | >50 | >50 | >50 |
| 18 | $C_{12}K(NC_4K)_4NH_2$ | 5 | 45.4 | ND | 50 | ND | >50 | >50 | >50 |
| 19 | $C_{12}K(NC_4K)_5NH_2$ | 6 | 45.8 | ND | 12.5 | 6.3 | >50 | >50 | >50 |
| 20 | $C_{12}K(NC_4K)_6NH_2$ | 7 | 45.1 | ND | 9.4 ± 3.1 | 4.7 ± 2.2 | >50 | >50 | >50 |
| 21 | $C_{12}K(NC_4K)_7NH_2$ | 8 | 45.2 | ND | 9.4 ± 3.1 | 3.1 | >50 | >50 | >50 |
| 22 | $NC_{12}K(NC_4K)_5NH_2$ | 7 | 29.3 | ND | >50 | ND | >50 | >50 | >50 |
| 23 | $NC_{12}K(NC_4K)_6NH_2$ | 8 | 29.8 | ND | >50 | ND | >50 | >50 | >50 |
| 24 | $NC_{12}K(NC_4K)_7NH_2$ | 9 | 30.2 | ND | >50 | ND | >50 | >50 | >50 |
| 25 | $C_8KNC_8KNH_2$ | 2 | 38.9 | ND | >50 | ND | >50 | >50 | >50 |
| 26 | $C_8K(NC_8K)_2NH_2$ | 3 | 36 | ND | >50 | ND | >50 | >50 | >50 |
| 27 | $C_8K(NC_8K)_3NH_2$ | 4 | 39.5 | ND | >50 | ND | >50 | >50 | >50 |
| 28 | $C_8K(NC_8K)_4NH_2$ | 5 | 40.5 | ND | >50 | ND | >50 | >50 | >50 |
| 29 | $C_8K(NC_8K)_5NH_2$ | 6 | 40.8 | ND | 25 | 3.1 | >50 | >50 | >50 |
| 30 | $C_8K(NC_8K)_6NH_2$ | 7 | 40.3 | ND | 25 | ND | >50 | >50 | >50 |
| 31 | $C_8K(NC_8K)_7NH_2$ | 8 | 40.3 | ND | 12.5 | ND | >50 | >50 | >50 |
| 32 | $KNC_8KNH_2$ | 3 | 21.6 | ND | >50 | ND | >50 | >50 | >50 |
| 33 | $K(NC_8K)_2NH_2$ | 4 | 27.3 | ND | >50 | ND | >50 | >50 | >50 |
| 34 | $K(NC_8K)_3NH_2$ | 5 | 30 | ND | >50 | ND | >50 | >50 | >50 |
| 35 | $K(NC_8K)_4NH_2$ | 6 | 31.7 | ND | >50 | ND | >50 | >50 | >50 |
| 36 | $K(NC_8K)_5NH_2$ | 7 | 33.1 | ND | >50 | >50 | >50 | >50 | >50 |
| 37 | $K(NC_8K)_6NH_2$ | 8 | 33.4 | ND | >50 | >50 | >50 | >50 | >50 |
| 38 | $K(NC_8K)_7NH_2$ | 9 | 34.2 | ND | >50 | 37.5 | >50 | >50 | >50 |
| 39 | $C_{12}KNC_8KNH_2$ | 2 | 50.9 | ND | >50 | ND | >50 | >50 | >50 |
| 40 | $C_{12}K(NC_8K)_2NH_2$ | 3 | 48 | ND | >50 | ND | >50 | >50 | >50 |
| 41 | $C_{12}K(NC_8K)_3NH_2$ | 4 | 46 | ND | >50 | ND | >50 | >50 | >50 |
| 42 | $C_{12}K(NC_8K)_4NH_2$ | 5 | 49 | ND | 25 | 4.7 ± 2.2 | >50 | 37.5 ± 18 | 50 |
| 43 | $C_{12}K(NC_8K)_5NH_2$ | 6 | 49.7 | >100 | 3.1 | 0.4 | 50 | 50 | 12.5 |
| 44 | $C_{12}K(NC_8K)_6NH_2$ | 7 | 50 | >100 | 3.1 | 0.8 | 50 | 50 | 12.5 |
| 45 | $C_{12}K(NC_8K)_7NH_2$ | 8 | 47.5 | >100 | 3.1 | ND | 6.3 | 50 | 12.5 |
| 46 | $NC_{12}KNC_8KNH_2$ | 3 | 29.6 | ND | >50 | ND | >50 | >50 | >50 |
| 47 | $NC_{12}K(NC_8K)_2NH_2$ | 4 | 35 | ND | >50 | ND | >50 | >50 | >50 |
| 48 | $NC_{12}K(NC_8K)_3NH_2$ | 5 | 33.7 | ND | >50 | ND | >50 | >50 | >50 |
| 49 | $NC_{12}K(NC_8K)_4NH_2$ | 6 | 36.2 | ND | >50 | 12.5 | >50 | >50 | >50 |
| 50 | $NC_{12}K(NC_8K)_5NH_2$ | 7 | 36.6 | ND | 50 | 6.3 | >50 | >50 | >50 |
| 51 | $NC_{12}K(NC_8K)_6NH_2$ | 8 | 37 | ND | 25 | 6.3 | >50 | >50 | >50 |
| 52 | $NC_{12}K(NC_8K)_7NH_2$ | 9 | 36.9 | ND | 12.5 | ND | 50 | >50 | >50 |
| 53 | $C_{12}KK(NC_8K)_4NH_2$ | 6 | 47 | >100 | 6.3 | ND | 50 | 37.5 ± 18 | 25 |
| 54 | $C_{12}KNC_{12}KNH_2$ | 2 | 59 | 45 ± 12 | 20.8 ± 7.2 | ND | >50 | 18.8 ± 7.2 | >50 |
| 55 | $C_{12}K(NC_{12}K)_2NH_2$ | 3 | 52.9 | ND | >50 | 37.5 ± 18 | >50 | >50 | >50 |
| 56 | $C_{12}K(NC_{12}K)_3NH_2$ | 4 | 53.5 | ND | >50 | >50 | >50 | >50 | >50 |
| 57 | $C_{12}K(NC_{12}K)_4NH_2$ | 5 | 53.4 | ND | >50 | >50 | >50 | >50 | >50 |
| 58 | $KNC_{12}KNH_2$ | 3 | 32 | >100 | >50 | >50 | >50 | >50 | >50 |
| 59 | $K(NC_{12}K)_2NH_2$ | 4 | 40 | >100 | >50 | >50 | >50 | >50 | >50 |
| 60 | $K(NC_{12}K)_3NH_2$ | 5 | 44 | >100 | 12.5 | 3.1 | 25 | >50 | >50 |
| 61 | $K(NC_{12}K)_4NH_2$ | 6 | 46 | 6.5 ± 3.5 | 25 | 2.3 ± 1.1 | >50 | >50 | >50 |
| 62 | $K(NC_{12}K)_5NH_2$ | 7 | 47 | ND | >50 | 3.1 | ND | >50 | ND |
| 63 | $K(NC_{12}K)_6NH_2$ | 8 | 48 | ND | >50 | 3.1 | ND | ND | ND |
| 64 | $K(NC_{12}K)_7NH_2$ | 9 | 50 | ND | >50 | 6.3 | ND | >50 | ND |
| 65 | $(NC_{12}K)_2NH_2$ | 3 | 38.8 | >100 | >50 | >50 | >50 | >50 | >50 |
| 66 | $(NC_{12}K)_3NH_2$ | 4 | 44.3 | >100 | 25 | 6.3 | 50 | >50 | >50 |
| 67 | $(NC_{12}K)_4NH_2$ | 5 | 46.8 | 4 ± 1.4 | >50 | >50 | >50 | >50 | >50 |
| 68 | $(NC_{12}K)_5NH_2$ | 6 | 47.8 | ND | >50 | 12.5 | >50 | >50 | >50 |
| 69 | $(NC_{12}K)_6NH_2$ | 7 | 49 | ND | >50 | 3.1 | ND | >50 | ND |
| 70 | $(NC_{12}K)_7NH_2$ | 8 | 50 | ND | >50 | 12.5 | ND | ND | ND |
| 71 | $(NC_{12}K)_8NH_2$ | 9 | 51 | ND | >50 | 1.6 | ND | ND | ND |
| 72 | $KKNC_{12}KNH_2$ | 4 | 30.9 | >100 | >50 | ND | >50 | >50 | >50 |
| 73 | $(KNC_{12}K)_2NH_2$ | 5 | 38.1 | >100 | >50 | ND | 50 | >50 | >50 |
| 74 | $K(KNC_{12}K)_2NH_2$ | 6 | 37.3 | >100 | >50 | ND | 25 | >50 | >50 |
| 75 | $C_8KKNC_{12}KNH_2$ | 3 | 40.3 | >100 | >50 | ND | >50 | >50 | >50 |

TABLE 3-continued

| SEQ ID NO: | Polymer | Q | ACN (%) | LC50 | MIC E.c. | MIC EDTA E.c. | MIC P.a. | MIC MR S.a. | MIC B.c. |
|---|---|---|---|---|---|---|---|---|---|
| 76 | $C_8(KNC_{12}K)_2NH_2$ | 4 | 45 | >100 | 25 | ND | 12.5 | >50 | 3.1 |
| 77 | $C_8K(KNC_{12}K)_2NH_2$ | 5 | 42.6 | >100 | 37.5 ± 18 | ND | 12.5 | >50 | 6.3 |
| 78 | $C_{12}KKNC_{12}KNH_2$ | 3 | 54 | 28.5 ± 9.2 | 18.8 ± 8.8 | 9.4 ± 4.4 | 25 | 3.1 | 3.1 |
| 79 | $C_{12}(KNC_{12}K)_2NH_2$ | 4 | 53.3 | 16.5 ± 6.4 | 3.1 | ND | 3.1 | 1.6 | 3.1 |
| 80 | $C_{12}K(KNC_{12}K)_2NH_2$ | 5 | 51 | 88 ± 3 | 3.1 | ND | 3.1 | 12.5 | 3.1 |
| 81 | $NC_{12}KKNC_{12}KNH_2$ | 4 | 38.9 | >100 | >50 | ND | >50 | >50 | >50 |
| 82 | $NC_{12}(KNC_{12}K)_2NH_2$ | 5 | 38.5 | >100 | 50 | ND | 12.5 | >50 | 3.1 |
| 83 | $NC_{12}K(KNC_{12}K)_2NH_2$ | 6 | 38.6 | >100 | 25 | ND | 25 | >50 | 6.3 |
| 84 | $C_{12}OrnNC_{12}OrnNH_2$ | 2 | 53.8 | 24 ± 6 | 10.4 ± 3.6 | ND | 25 | 12.5 | 16.7 ± 7.2 |
| 85 | $C_{12}ArgNC_{12}ArgNH_2$ | 2 | 57.1 | 9.5 ± 1 | 42 ± 14.4 | ND | >50 | 12.5 | 42 ± 14.4 |
| 86 | $C_{12}KNC_{12}K$ | 1 | 56.9 | >100 | >50 | ND | >50 | >50 | >50 |
| 87 | $C_{12}K(NC_{12}K)_2$ | 2 | 56.4 | ND | >50 | ND | >50 | 31.3 ± 26.5 | 50 |
| 88 | $C_{12}K(NC_{12}K)_3$ | 3 | 54.6 | ND | >50 | ND | >50 | >50 | >50 |
| 89 | $KNC_{12}K$ | 2 | 33.2 | >100 | >50 | ND | >50 | >50 | >50 |
| 90 | $K(NC_{12}K)_2$ | 3 | 36.4 | >100 | >50 | ND | >50 | >50 | >50 |
| 91 | $K(NC_{12}K)_3$ | 4 | 42.8 | >100 | 25 | ND | 50 | >50 | >50 |
| 92 | $(NC_{12}K)_2$ | 2 | 38.7 | >100 | >50 | ND | >50 | >50 | >50 |
| 93 | $(NC_{12}K)_3$ | 3 | 43.8 | >100 | 50 | ND | >50 | 50 | >50 |
| 94 | $(NC_{12}K)_4$ | 4 | 45.8 | ND | 50 | ND | >50 | >50 | >50 |
| 95 | $FmocK(NC_{12}K)_2$ | 2 | 41 | ND | >50 | ND | >50 | 6.3 | 12.5 |

The Effect of Physical Parameters (Charge and Hydrophobicity) on Antimicrobial Activity:

Charge and hydrophobicity may be viewed as two conflicting physical characteristics of a molecule: charge facilitates dissolution of a compound in aqueous media by interacting with the polar water molecules, while hydrophobicity, which typically corresponds to the number and length of non-polar hydrocarbon moieties, hinders dissolution. Optimization of these physical characteristics is crucial in the development of drugs in general and antimicrobial agents in particular, as these characteristics affect pharmaceutically important traits such as membrane permeability and transport in and across biological systems.

Therefore, the library of polymers prepared to study the effect of serial increases in charge and hydrophobicity properties was measured for its antimicrobial activity against two gram-negative bacteria: *E. coli* (results are presented in column 6 of Table 3 hereinabove) and *P. aeruginosa* (results are presented in column 8 of Table 3), and two gram-positive bacteria: methicilin-resistant *S. aureus* (results are presented in column 9 of Table 3) and *Bacillus cereus* (results are presented in column 10 of Table 3).

A serial increase in positive charge was achieved by preparing polymers with serial elongation of the chain with respect to the number of lysine residues. Serial increases in hydrophobicity was achieved by preparing polymers with serial rising of the number of fatty acid residues (as a representative hydrophobic moiety) and/or with serial rising of the number of carbon atoms in each fatty acid residue. Serial increases in both positive charge and hydrophobicity were achieved by preparing polymers with serial rising of the number of lysine-amino fatty acid conjugates.

As can be seen in Table b 3, increasing the hydrophobicity of the polymers by increasing the number of the carbon atoms in the fatty acid residue from 4 to 12, via 8 carbon atoms, was found to affect the antimicrobial activity of the polymers. Series of polymers in which the repeating hydrophobic moiety was a 4-amino-butiric acid (see, entries 1-24 in Table 3) was compared to a series in which the repeating hydrophobic moiety was an 8-amino-caprylic acid (see, entries 25-53 in Table 3) and to a series in which the repeating hydrophobic moiety was a 12-amino-lauric acid (see, entries 54-95 in Table 3). The results, presented in Table 3, indicated that polymers in which the repeating hydrophobic moiety was a 4-amino-butiric acid (see, entries 1-14 in Table 3) and a 8-amino-caprylic acid (see, entries 25-38 in Table 3), generally did not show significant antimicrobial activity up to the highest tested concentration of 50 μM. The only polymers which had no 12-animo-lauric acid residue in their sequence and which showed significant antimicrobial activity at lower concentrations were $C_8K(NC_8K)_5NH_2$ (SEQ ID NO: 29), $C_8K(NC_8K)_6NH_2$ (SEQ ID NO: 30) and $C_8K(NC_8K)_7NH_2$ (see Table 3), whereas polymers containing one or more of the more hydrophobic 12-amino-lauric acid residue, (see, entries 58-83 in Table 3), showed significant activity at concentrations as low as 1.6 μM.

Evaluation of the effect of the hydrophobicity of the polymers in terms of the acetonitrile percentages of the HPLC mobile phase in which the polymers were eluted further demonstrates the correlation between this property and the antimicrobial activity of the polymer. As can be seen in the data presented in column 4 of Table 3, all the polymers which displayed a significant level of antimicrobial activity against any one of the tested bacteria were eluted in acetonitrile concentrations higher than 36%, whereby none of the polymers that were eluted in acetonitrile concentrations lower than 36% exhibited such an activity.

FIG. 1 presents the distribution of polymers which exhibited a significant microbial activity (MIC value of less than 50 ☐M) in any one of the four assays conducted. As is clearly seen in FIG. 1, antimicrobial activity against one or more of the tested bacteria was exhibited only by polymers which were eluted at acetonitrile concentrations of 36% and up and, furthermore, polymers which were found active against all the tested bacteria were eluted at acetonitrile concentrations of 51% and up.

As can further be seen in Table 3, increasing the positive charge of the polymers by increasing the number of the lysine residues in the polymer was found to affect the antimicrobial activity of the polymers only marginally. Thus, polymers having net charges raging from +1 to +9 in each series were tested for antimicrobial activity. The results, presented in Table 3, indicated, for example, that most of the polymers with the highest net positive charge of +9, namely $K(NC_4K)_7$ NH$_2$ (SEQ ID NO: 14), NC$_{12}$K(NC$_4$K)$_7$NH$_2$ (SEQ ID NO: 24), K(NC$_8$K)$_7$NH$_2$ (SEQ ID NO: 38), NC$_{12}$K(NC$_8$K)$_7$NH$_2$ (SEQ ID NO: 52), K(NC$_{12}$K)$_7$NH$_2$ (SEQ ID NO: 64), (NC$_{12}$K)$_8$NH$_2$ (SEQ ID NO: 71), (see, Table 3), did not exhibit significant activity, with only NC$_{12}$K(NC$_8$K)$_7$NH$_2$ (SEQ ID NO: 52) (see, Table 3) exhibiting significant activity.

Table 4 below presents a summary of the results obtained in these experiments, in terms of the effect of the net positive charge of the polymers and the antimicrobial activity thereof. Row 2 of Table 4 presents the number of polymers in 9 bins, wherein each bin represents a net positive charge, starting from +9 to +1. Row 3 of Table 4 presents the total number of activity assays which were measured in the charge bin, namely, the number of polymers in the bin multiplied by the four bacterial assays described above. Row 4 of Table 4 presents the number of polymers in each of the bins that were found active against any one of the four bacteria. Row 5 of Table 4 presents the percentage of the active polymers from the total number of assays measured in the charge bin. As can be seen in Table 4, (row 4, for example), only a little if any correlation between the net positive charge of the polymers and their antimicrobial activity was found. It appears from these results that the only feature that seems to affect the antimicrobial activity of the tested polymers is a net positive charge that is greater than +1.

Figure 5A:
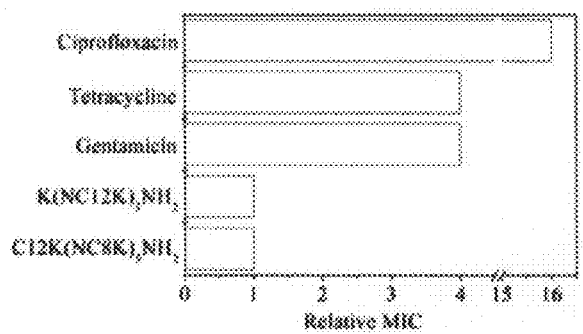
FIGS. 5 $a$-$b$ presents a bar graph demonstrating the non-resistance inducing effect of exemplary polymers according to the present invention, by measuring MICs level evolution on, E. coli after 10 iterations of successive exposures of bacteria to sub-lytic concentrations of $K(NC_{12}K)_3NH_2$ (SEQ ID NO: 60) and $C_{12}K(NC_8K)_5NH_2$ (SEQ ID NO: 43), as compared to exposures to three classical antibiotic agents, tetracycline, gentamicin and ciprofloxacin (FIG. 5$a$), and on methicilin-resistant S. aureus after 15 iterations of successive exposures of bacteria to sub-lytic concentrations of $C_{12}KKNC_{12}KNH_2$ (SEQ ID NO: 78), as compared to exposures to two antibiotic agents, rifampicin and tetracycline (FIG. 5$b$) (the relative MIC is the normalized ratio of the MIC obtained for a given subculture to the concomitantly determined MIC obtained on bacteria harvested from control wells (wells cultured without antimicrobial agent) from the previous generation.

As is clearly seen in FIG. 5a, the relative MIC value of K(NC$_{12}$K)$_3$NH$_2$ (SEQ ID NO: 60) and C$_{12}$K(NC$_8$K)$_5$NH$_2$ (SEQ ID NO: 43)against E. coli remained stable for 10 successive subculture generations following the initial exposure. In sharp contrast, during the same period of time, the MIC values tested with the reference antibiotic agents substantially increased, reflecting the emergence of antibiotic-resistant bacteria. Thus, at the tenth generation, the MIC values increased by 4-fold for tetracycline and gentamicin, and by more than 16-fold for ciprofloxacin. These results demonstrate that exposing bacteria to the antimicrobial polymers of the present invention do not result in development of resistance.

Figure 5B:
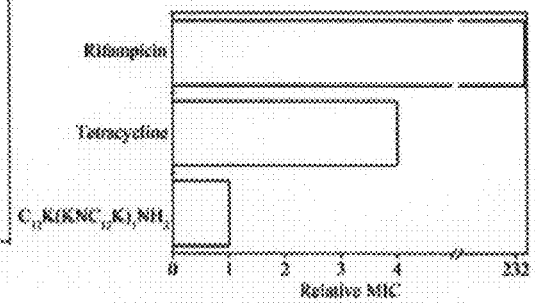

As is clearly seen in FIG. 5b, the relative MIC value of C$_{12}$KKNC$_{12}$KNH$_2$ against methicilin-resistant S. aureus remained stable for 15 successive subculture generations following the initial exposure. In sharp contrast, during the same period of time, the MIC values tested with the reference antibiotic agents substantially increased, reflecting the emergence of antibiotic-resistant bacteria. Thus, at the tenth generation, the MIC values increased by more than 230-fold for rifampicin, and by 4-fold for tetracycline. These results demonstrate that exposing bacteria to the antimicrobial polymers of the present invention do not result in development of resistance.

TABLE 4

| | Charge | | | | | | | | |
|---|---|---|---|---|---|---|---|---|---|
| | +9 | +8 | +7 | +6 | +5 | +4 | +3 | +2 | +1 |
| Number of polymers | 6 | 10 | 10 | 12 | 14 | 16 | 15 | 11 | 1 |
| Number of assays | 24 | 40 | 40 | 48 | 56 | 64 | 60 | 44 | 4 |
| Number of actives | 1 | 6 | 4 | 12 | 13 | 9 | 4 | 12 | 0 |
| Percent actives | 4.2% | 15.0% | 10.0% | 25.0% | 23.2% | 14.1% | 6.7% | 27.3% | 0.0% |

Figure 2:
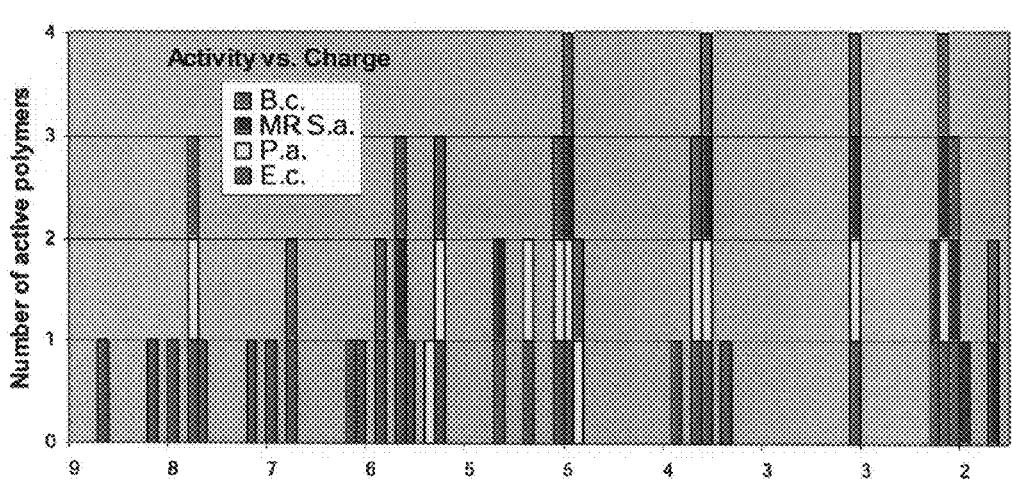
FIG. 2 presents a cumulative bar graph demonstrating the lack of correlation between the antimicrobial activity and the net positive charge of exemplary polymers according to the present invention, by marking the polymers which exhibited a significant microbial activity (MIC value of less than 50 □M) against $E.$ $coli$ (in red bars), $P.$ $aeruginosa$ (in yellow bars), methicilin-resistant $S.$ $aureus$ (in blue bars) and $B.$ $cereus$ (in green bars), over bins representing the net positive charge from +9 to +1.

FIG. 2 presents the distribution of polymers according to the present invention which exhibited a significant microbial activity (MIC value of less than 50 □M) in any one of the four assays mentioned above. As can be clearly seen in FIG. 2, polymers which showed antimicrobial activity against any one of the four bacteria are scattered across the entire range of charge values, excluding the +1 charge, and thus demonstrating the lack of correlation between the net positive charge of the polymers and the antimicrobial activity thereof.

Development of antimicrobial-resistance in bacteria:

The possible development of resistance to the polymers of the present invention was tested by measuring the MIC levels following multiple exposures of the bacteria to exemplary polymers according to the present invention, as described hereinabove in the Experimental Methods section. The tested polymers in these experiments were K(NC12K)3NH2 (SEQ ID NO: 60), C12K(NC8K)5NH2- (SEQ ID NO: 43) and C12KKNC12KNH2 (SEQ ID NO: 78), whereby the development of resistance of E. coli to K(NC12K)3NH2 (SEQ ID NO: 60) and C12K(NC8K)5NH2 (SEQ ID NO: 43) was compared with that of three classical antibiotics: gentamicin, tetracycline and ciprofloxacin, and the development of resistance of methicilin-resistant S. aureus to C12KKNC12KNH2 (SEQ ID NO: 78) was compared with that of two classical antibiotics: rifampicin and tetracycline.

The data obtained in these experiments is presented in FIGS. 5a and 5b. FIG. 5a presents the data obtained for K(NC$_{12}$K)$_3$NH$_2$ -(SEQ ID NO: 60) and C$_{12}$K(NC$_8$K)$_5$NH$_2$ (SEQ ID NO: 43). FIG. 5b presents the data obtained for C$_{12}$KKNC$_{12}$KNH$_2$ (SEQ ID NO: 78).

The development of antimicrobial resistance following exposure to the polymers of the present invention was further evaluated in a cross resistance experiment, in which a methicilin-resistant strain of S. aureus was exposed to exemplary polymers of the present invention. The results obtained in this experiment are presented in Table 3 hereinabove, under column "MIC MR S. a."and clearly demonstrate the persisting antimicrobial activity of the polymers of the present invention against an antibiotic-resistant bacteria, especially in the case of C$_{12}$(KNC$_{12}$K)$_2$NH$_2$, C$_{12}$KKNC$_{12}$KNH$_2$, FmocK(NC$_{12}$K)$_2$, C$_{12}$K(KNC$_{12}$K)$_2$NH$_2$, C$_{12}$OrnNC$_{12}$OrnNH$_2$, C$_{12}$ArgNC$_{12}$ArgNH$_2$, C$_{12}$KNC$_{12}$KNH$_2$, C$_{12}$K(NC$_{12}$K)$_2$, C$_{12}$K(NC$_8$K)$_4$NH$_2$ and C$_{12}$KK(NC$_8$K)$_4$NH$_2$ (SEQ ID NOS: 79, 78, 95, 80, 84, 85, 54, 87, 42 and 53, respectively- in Table 3).

Figure 3:
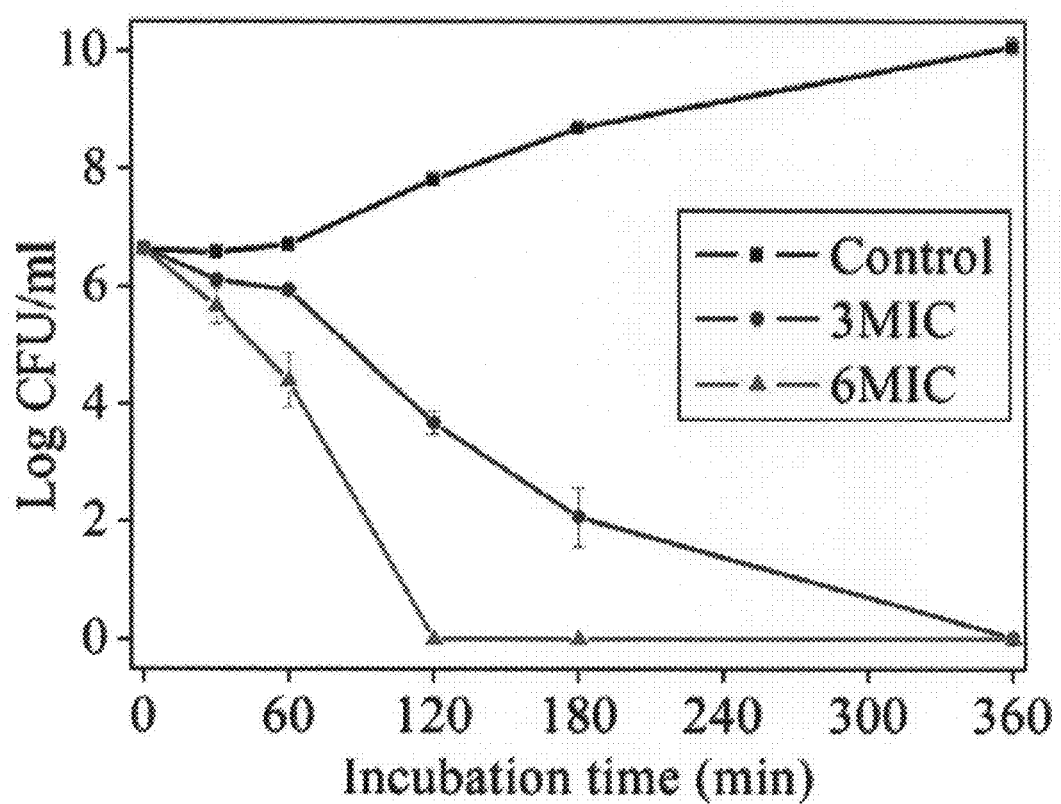
FIG. 3 presents comparative plots demonstrating the kinetic bactericidal effect of $C_{12}K(NC_8K)_5NH_2$, (SEQ ID NO: 43) an exemplary polymer according to the present invention, on E. coli. incubated in the presence of the polymer, with colony forming units (CFU) counts performed after the specified incubation periods and compared in a dose-dependent experiment at zero (control), 3 and 6 multiples of the minimal inhibitory concentration (MIC) value (3.1µM) in LB medium at 37° C.

Kinetic studies of antimicrobial activity at time intervals:

The kinetic rates of bactericidal activity of a representative polymer of the present invention, C$_{12}$K(NC$_8$K)$_5$NH$_2$ (SEQ ID NO: 43), was tested as described in the methods section above at concentrations corresponding to 3 and 6 times the MIC value. The results, presented in FIG. 3, clearly reflect the antibacterial activity of the polymer. As is shown in FIG. 3, the viable bacterial population was reduced by nearly seven log units within 6 hours upon being exposed to the polymer at a concentration of 3 multiples of the MIC, and within 2 hours upon being exposed to the polymer at a concentration of 6 multiples of the MIC. These remarkable results further demonstrate the efficacy of the antimicrobial polymers of the present invention, in terms of an efficient pharmacokinetic profile.

Antimicrobial activity at enhanced outer-membrane permeability conditions:

The results obtained following addition of the cation-chelator EDTA to the assay buffer, which was aimed at enhancing the outer-membrane permeability of gram-negative bacteria such as E. ccli, are presented in Table 3 above under the column headed "MIC EDTA E. c.". These results clearly show that the activity profile of the polymers in the presence of EDTA is different than that obtained without EDTA (presented in Table 3 above, column headed "MIC E.c."). Thus, polymers such as $K(NC_8K)_7NH_2$, $NC_{12}K(NC_8K)_4NH_2$, $NC_{12}K(NC_8K)_5NH_2$, $C_{12}K(NC_{12}K)_2NH_{12}$, $K(NC_{12}K)_5NH_2$, $K(NC_{12}K)_6NH_2$, $K(NC_{12}K)_7NH_2$, $(NC_{12}K)_4NH_2$, $(NC_{12}K)_5NH_2$, $(NC_{12}K)_6NH_2$, $(NC_{12}K)_7NH_2$ and $(NC_{12}K)_8NH_2$, which exhibited minor or no antimicrobial activity in the absence of EDTA, became up to more than 50 folds more active in its presence (SEQ ID NOS: 38, 49, 50, 55, 62, 63, 64, 67, 68, 69, 70 and 71 respectively, in Table 3). Other polymers, such as $K(NC_{12}K)_4NH_2$, $C_8K(NC_8K)_5NH_2$, $C_{12}K(NC_8K)_4NH_2$, $NC_{12}K(NC_8K)_6NH_2$ and $(NC_{12}K)_3NH_2$, which exhibited only marginal antimicrobial activity in the absence of EDTA, became between 11-folds and 4-fold more active in its presence, respectively (see, respective SEQ ID NOS:61, 29, 42, 51 and 66 in Table 3).

These results illuminate the tight correlation between membrane permeability of antimicrobial agents and their efficacy and further demonstrate the complex relationship and delicate balance between the positive charge and the hydrophobic characteristics of the polymers of the present invention on the antimicrobial activity thereof.

Susceptibility to plasma proteases assays results:

The susceptibility of the polymers of the present invention to enzymatic cleavage was assessed by pre-incubating exemplary polymers according to the present invention, $C_{12}K(NC_8K)_5NH_2$ (SEQ ID NO: 43), $K(NC_{12}K)_3NH_2$ (SEQ ID NO: 60), $C_{12}KNC_2KNH_2$, and $C_{12}KKNC_{12}KNH_2$ (SEQ ID NO: 78), and an exemplary reference AMP, a 16-residues dermaseptin S4 derivative ($S4_{16}$), in human plasma (50%) for various time periods and thereafter determining the antibacterial activity thereof against E. ccli and S. aureus. Statistical data were obtained from at least two independent experiments performed in duplicates.

The results are presented in Table 5 hereinbelow, wherein "MIC (E.c.) $C_{12}K(NC_8K)_5NH_2$ (μM)" is the minimal inhibitory concentration in μM of $C_{12}K(NC_8K)_5NH_2$, as measured for E. coli; "MIC (E.c.) $K(NC_{12}K)_3NH_2$ (μM)" is the minimal inhibitory concentration in μM of $K(NC_{12}K)_3NH_2$, as measured for E. coli; "MIC (E.c.) $S4_{16}$ (μM)" is the minimal inhibitory concentration in μM of $S4_{16}$, an exemplary dermaseptin serving as a reference AMP, as measured for E. coli; "MIC S.a. $C_{12}KNC_{12}KNH_2$ (μM)" is the minimal inhibitory concentration in μM of $C_{12}KNC_{12}KNH_2$, as measured for S. aureus; and "MIC (S.a.) $C_{12}KKNC_{12}KNH_2$ (μM)" is the minimal inhibitory concentration in μM of $C_{12}KKNC_{12}KNH_2$, as measured for S. aureus.

As is shown in Table 5, while the reference AMP, $S4_{16}$, was completely inactivated upon exposure to human plasma, the polymers of the present invention maintained their activity, and thus, the superior stability of the polymers according to the present invention as compared with that of the highly active yet unstable AMPs was clearly demonstrated. More specifically, as is shown in Table 5, the dermaseptin $S4_{16}$ did not display a measurable MIC after 3 hours exposure to serum enzymes, even at a concentration of more than 16-folds higher (greater than 50 μM) than the MIC value, indicating that the peptide was inactivated probably due to enzymatic proteolysis. In sharp contrast, the polymers of the present invention exhibited prolonged resistance to enzymatic degradation. As is further shown in Table 5, the activity of short polymers such as $C_{12}KNC_{12}KNH_2$ and $C_{12}KKNC_{12}KNH_2$ (SEQ ID NOs: 54 and 78 respectively) was reduced only by 2-folds after 6 hours exposure to plasma enzymes while longer polymers such as $K(NC_{12}K)_3NH_2$-(SEQ ID NO: 60) and $C_{12}K(NC_8K)_5NH_2$ (SEQ ID NO: 43) did not display any degree of inactivation even after 18 hours incubation.

Hemolysis Assays:

The toxic effect of the polymers of the present invention on human erythrocytes (red blood cells, RBC) was assayed as described hereinabove. The results are presented in Table 3, under the column headed "$LC_{50}$", in terms of the lytic concentrations that induced 50% ($LC_{50}$) lysis of red blood cells in phosphate buffer (PBS).

As shown in Table 3, polymers such as $C_{12}K(NC_8K)_7NH_2$, $C_8(KNC_{12}K)_2NH_2$, $C_8K(KNC_{12}K)_2NH_2$, $NC_{12}K(KNC_{12}K)_2NH_2$, $C_{12}K(NC_8K)_5NH_2$, $C_{12}K(NC_8K)_6NH_2$, $NC_{12}(KNC_{12}K)_2NH_2$, $C_{12}KK(NC_8K)_4NH_2$ and $K(NC_{12}K)_3NH_2$- (see, respective SEQ ID NOS: 5, 76, 77, 83, 43, 44, 82, 53 and 60 in Table 3) which exhibited high antimicrobial activity, displayed low hemolytic activity. As is further shown in Table 3, polymers including various fatty acid moieties conjugated to the N-terminus thereof and/or a relatively large number of lysine residues, were particularly found to exhibit potent antibacterial activity along with low hemolytic activity. These results clearly demonstrate the low toxicity of the polymers of the present invention against human red blood cells.

Circular dichroism (CD):

The secondary structure of selected polymers according to the present inventions was studied by circular dichroism (CD) measurements in various media, as described hereinabove in the Experimental Methods section. The CD profiles of $C_{12}K(NC_8K)_5NH_2$ (SEQ ID NO: 43) and $C_{12}K(NC_8K)_7NH_2$ (SEQ ID NO: 45), exemplary antimicrobial polymers according to the present invention, and $NC_{12}K_4S4_(1-14)$ (SEQ ID NO: 97), an exemplary dermaseptin derivative, are presented in FIG. 4. The CD data presented represent an average of three separate recordings values.

As is shown in FIG. 4, the CD spectra of the polymers of the present invention displayed a minimum near 200 nm, indicating a random structure. The same CD spectra were observed in assays conducted in the presence and absence of liposomes. The CD spectra of the control dermaseptin $NC_{12}K_4S4_(1-14)$ (SEQ ID NO: 97) showed a typical spec-

TABLE 5

| Incubation time (hours) | MIC (E.c.) $C_{12}K(NC_8K)_5NH_2$ (μM) | MIC (E.c.) $K(NC_{12}K)_3NH_2$ (μM) | MIC (E.c.) $S4_{16}$ (μM) | MIC (S.a.) $C_{12}KNC_{12}KNH_2$ (μM) | MIC (S.a.) $C_{12}KKNC_{12}KNH_2$ (μM) |
|---|---|---|---|---|---|
| 0 | 3.1 | 12.5 | 3.1 | 12.5 | 3.1 |
| 3 | 3.1 | 12.5 | >50 | 12.5 | 3.1 |
| 6 | 3.1 | 12.5 | >50 | 25 | 6.3 |
| 18 | 3.1 | 12.5 | >50 | 25 | 6.3 | trum characteristic of an alpha-helical secondary structure. Similar results were observed in 20 % trifluoroethanol/water (data not shown).

Surface plasmon resonance assay:

The binding properties of exemplary polymers according to the present invention to membranes were studied using surface plasmon resonance (SPR) measurements, as described hereinabove in the Methods section.

Figure 6:
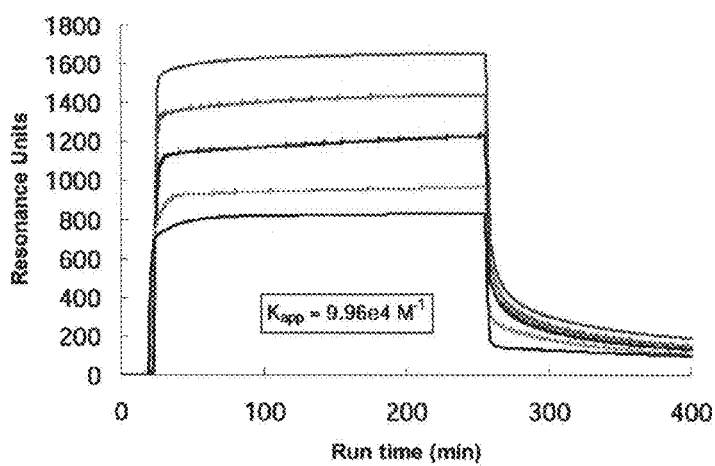
FIG. 6 presents association and dissociation curves (binding rates) obtained by surface plasmon resonance (SPR) measurements, demonstrating the membrane binding properties of various doses (0.21, 0.42, 0.84, 1.67, 3.35 µg) of $C_{12}K(NC_8K)_5NH_2$ (SEQ ID NO: 43), an exemplary polymer according to the present invention, to a model membrane ($K_{app}$ is the resulting binding constants calculated assuming a 2-step model)

The obtained data indicated that the polymers according to the present invention display high affinity binding to a model membrane mimicking the bacterial plasma membrane, with $K_{app}$ ranging from $10^4$ to $10^7$ M$^{-1}$). FIG. 6, for example, presents the data obtained with $C_{12}K(NC_8K)_5NH_2$ (SEQ ID NO: 43), and demonstrates the high affinity binding of this exemplary polymer according to the present invention ($K_{app}$ of $9.96 \times 10^4$ M$^{-1}$ to a model membrane..

An additional exemplary antimicrobial polymer according to the present invention, $K(NC_{12}K)_3NH_2$ (SEQ ID NO: 60), displayed an even higher affinity binding ($K_{app}$ of $6.3 \times 10^5$ M$^{-1}$, data not shown).

These results substantiate the affinity of the polymers of the present invention towards the membranes of a pathogenic microorganism.

Lipopolysaceharide binding assay:

The binding affinity of the positively charged polymers according to the present invention to the negatively charged lipopolysaccharides (LPS) present on the membrane of gram-negative bacteria was measured as described in the Methods section hereinabove. The maximal binding levels of seven exemplary polymers according to the present invention, $KNC_8KNH_2$ (SEQ ID NO: 32), $K(NC_8K)_2NH_2$ (SEQ ID NO: 33), $K(NC_8K)_3NH_2$ (SEQ ID NO: 34), $K(NC_8K)_6NH_2$ (SEQ ID NO: 37), $KNC_{12}KNH_2$ (SEQ ID NO: 58), $K(NC_{12}K)_2NH_2$ (SEQ ID NO: 59) and $K(NC_{12}K)_3NH_2$ (SEQ ID NO: 60), to liposomal membranes before and after incubation with LPS, as measured in these assays, are presented in FIG. 8.

Figure 8:
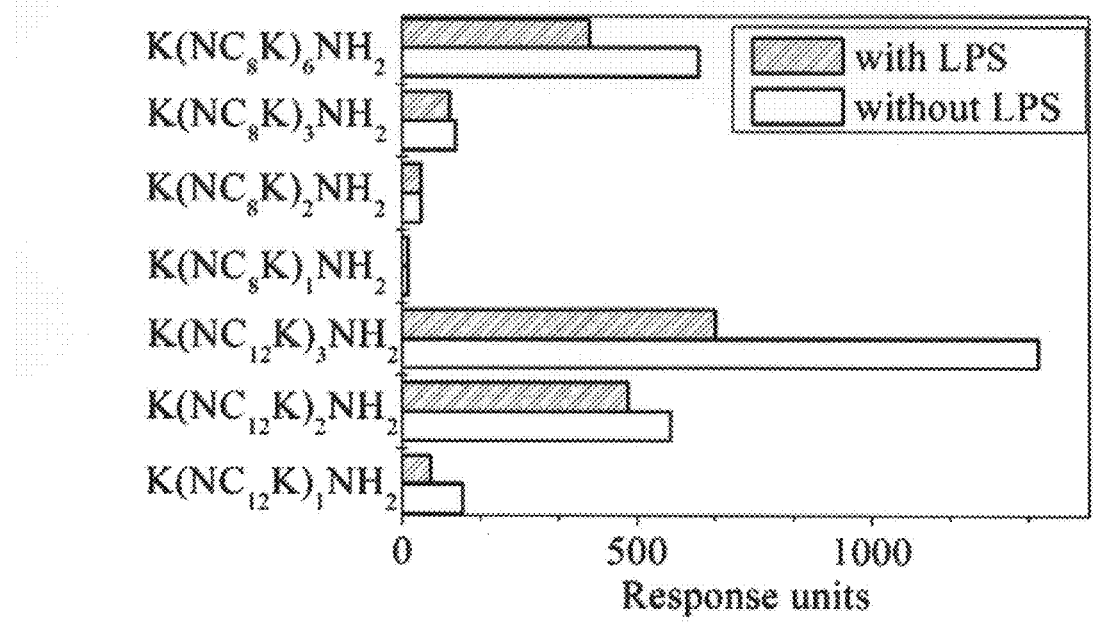
FIG. 8 presents a bar graph demonstrating the binding of the exemplary polymers according to the present invention, denoted as $KNC_8KNH_2$ (SEQ ID NO: 32), $K(NC_8K)_2NH_2$ (SEQ ID NO: 33), $K(NC_8K)_3NH_2$ (SEQ ID NO: 34), $K(NC_8K)_6NH_2$ (SEQ ID NO: 37), $KNC_{12}KNH_2$ (SEQ ID NO: 58), $K(NC_{12}K)_2NH_2$ (SEQ ID NO: 59) and $K(NC_{12}K)_3NH_2$ (SEQ ID NO: 60), to lipopolysaccharide, as measured by SPR, wherein the weaker binding of the polymers to liposomes after incubation with LPS substantiates that the polymers are bound to the LPS.

As can be seen in FIG. 8, the binding affinity of a polymer to the membrane is affected by the length of the polymer. Thus, for example, the binding affinity of $K(NC_8K)_6NH_2$ (SEQ ID NO: 37) is higher than that of $KNC_8KNH_2$ (SEQ ID NO: 32) and the binding affinity of $K(NC_{12}K)_3NH_2$ (SEQ ID NO: 60) was found higher than that of $KNC_{12}KNH_2$ (SEQ ID NO: 58).

As can be further seen in FIG. 8, the same correlation between the polymer length and its binding affinity to LPS was observed. Thus, for example, the polymers $K(NC_8K)_6NH_2$ (SEQ ID NO: 37) and $K(NC_{12}K)_3NH_2$ (SEQ ID NO: 60) -each exhibits close to 2-fold reduction of affinity to liposomal membrane following incubation with LPS, indicating binding of the polymers to LPS during the incubation period, which interferes with their binding to the membranal liposomes.

These results provide further support to a mechanism of action of the polymers that involves strong interaction with LPS, which promotes a destructive action against the bacterial membrane and by which the risk of development of endotoxemia is reduced.

Figure 7:
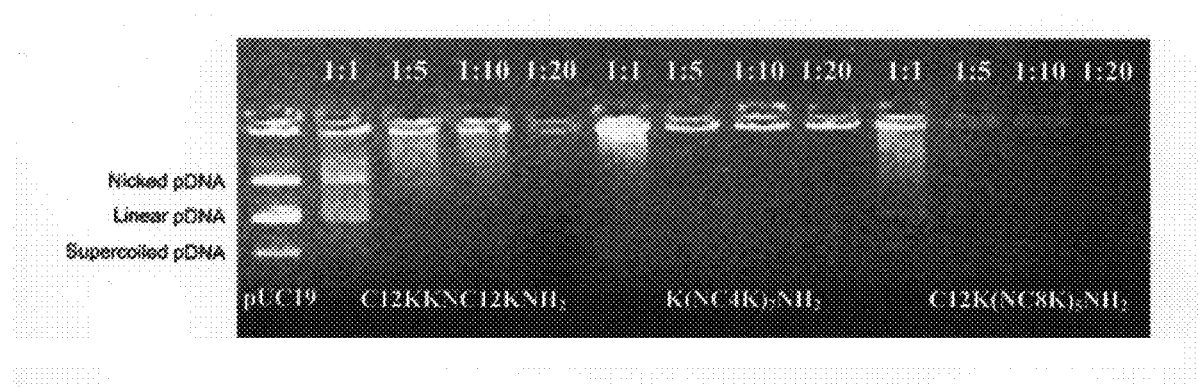
FIG. 7 presents a photograph of a UV illuminated 1 % agarose gel electrophoresis, demonstrating the DNA binding characteristics of $C_{12}KKNC_{12}KNH_2$ (SEQ ID NO: 78), $K(NC_4K)_7NH_2$ (SEQ ID NO: 14) and $C_{12}K(NC_8K)_5NH_2$ (SEQ ID NO: 43), exemplary polymers according to the present invention, as measured by DNA retardation assay after the polymers were incubated for 30 minutes at room temperature at the specified DNA/polymer ratios (w:w) using 200 nanograms of plasmid (normal migration in absence of the polymer of the plasmid pUC 19 is shown in leftmost lane)

DNA binding assay:

The binding properties of exemplary polymers according to the present invention to nucleic acids were studied by determining their ability to retard migration of DNA plasmids during gel electrophoresis in a 1 % agarose gel. The obtained results show that the polymers according to the present invention retard the migration of various plasmids (e.g., pUC19, pGL3 Luciferase Reporter Vector (Promega)) in a dose dependent manner. Representative results, obtained with the plasmid pUC19 in the absence and presence of three exemplary polymers of the present invention, $C_{12}KKNC_{12}KNH_2$ (SEQ ID NO: 78), $K(NC_4K)_7NH_2$ (SEQ ID NO: 14) and $C_{12}K(NC_8K)_5NH_{12}$, (SEQ ID NO: 43) are presented in FIG. 7 (Note: isolation of the plasmid from a bacterial culture results in three maj or bands and several minor bands, as seen in the leftmost slot of the gel's UV image). An apparent dose-dependent behavior was evident in the presence of the shortest tested polymer $C_{12}KKNC_{12}KNH_2$ (SEQ ID NO: 78). The dose-dependent behavior was further accentuated with the longer tested polymers $K(NC_4K)_7NH_2$ (SEQ ID NO: 14) and $C_{12}K(NC_8K)_5NH_2$ (SEQ ID NO: 43). Thus, at the lowest dose of $C_{12}KKNC_{12}KNH_2$ (SEQ ID NO: 78) (polymer to DNA ratio of 1:1), the supercoiled plasmid DNA band disappeared whereas the other bands displayed a smeared pattern. These results suggest that the inhibitory effect of the polymers of the present invention is higher with supercoiled DNA. Increasing the polymer doses resulted in accentuated effect, such that the retardation effect extended to all DNA species.

Furthermore, it was found that various polymer-DNA complexes remained intact after exposure to either DNAse digestive enzymes or peptidase digestive enzymes. These findings reveal a tight binding between the polymers of the present invention and the DNA molecule, exhibited by the mutual shielding exerted by the polymers to the DNA molecules and vice versa.

Figure 9:
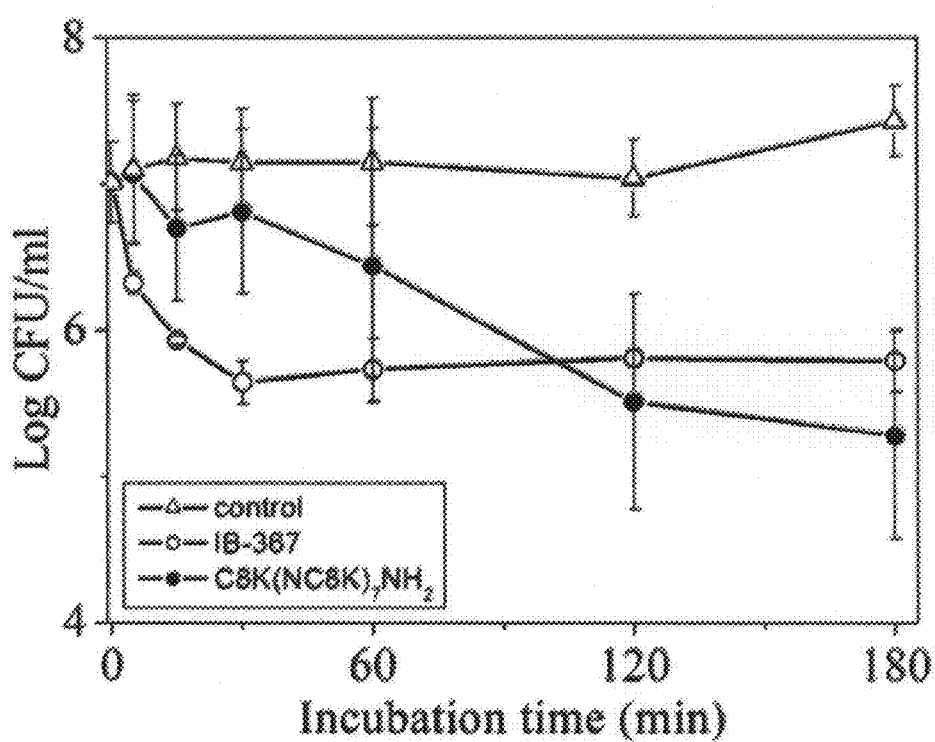
FIG. 9 presents comparative plots demonstrating the antimicrobial activity of $C_8K(NC_8K)_7NH_2$ (SEQ ID NO: 31), an exemplary polymer according to the present invention (in black circles), against the micro-flora found in human saliva, as compared to IB-367 (SEQ ID NO: 96), a peptide with known antimicrobial activity (in white circles) and the vehicle buffer as control (white triangle) in logarithmic units of CFU per ml versus incubation time.

Saliva microbicidal assays:

The antimicrobial activity of an exemplary polymer of the present invention, $C_8K_8$ (SEQ ID NO: 99), against microorganisms in human saliva was studied as described above. FIG. 9 presents the results obtained in this study in terms of the logarithmic units of CFU per ml as a function of the incubation time of the samples with the vehicle buffer (control), IB-367 (SEQ ID NO: 96) (antimicrobial agent with known activity control) and $C_8K_8$ (SEQ ID NO: 99). The results show that while in the control, untreated group the saliva microorganisms are persistent and proliferate without any treatment, the growth of saliva microorganisms treated is inhibited but proliferation is resumed after 30 minutes; whereby the growth of the saliva microorganisms treated with the polymer according to the present invention is inhibited without recovery.

Anti-Malarial Assays:

A of a group of polymers, according to the present invention, were tested for their anti-malarial effect on parasite growth and on mammalian cells. The obtained results are presented in Table 6 below, wherein:

"IC50 parasite (µM)" represents the concentration of the tested polymer in □M that is required for 50% inhibition of the growth of the malaria causing parasites, measured as described hereinabove (column 3 in Table 6);

"IC50 MDCK (µM)" represents the concentration of the tested polymer in □M that is required for 50% inhibition of growth of MDCK cells, measured as described hereinabove (column 3 in Table 6); and "IC50 Ratio" represents the ratio of IC50 MDCK over IC50 parasite, indicating the specificity of the polymer to parasitic membranes over that of mammalian cells.

TABLE 6

| Entry (SEQ ID NO:) | Polymer | IC$_{50}$ parasite (µM) | IC$_{50}$ MDCK (µM) | IC$_{50}$ Ratio |
|---|---|---|---|---|
| A (54) | $C_{12}KNC_{12}KNH_2$ | 3.54 | 156.8 | 44.29 |
| B (65) | $(NC_{12}K)_2NH_2$ | 4.63 | 609.2 | 131.58 |
| C (55) | $C_{12}K(NC_{12}K)_2NH_2$ | 0.85 | 92.1 | 108.35 |
| D (66) | $(NC_{12}K)_3NH_2$ | 0.14 | 48.3 | 352.55 |
| E (56) | $C_{12}K(NC_{12}K)_3NH_2$ | 0.08 | 37.3 | 449.40 |
| F (67) | $(NC_{12}K)_4NH_2$ | 1.59 | 57.0 | 35.85 |
| G (58) | $KNC_{12}KNH_2$ | 68.20 | 693.8 | 10.17 |
| H (59) | $K(NC_{12}K)_2NH_2$ | 7.85 | 157.4 | 20.05 |
| I (60) | $K(NC_{12}K)_3NH_2$ | 1.72 | 347.0 | 201.74 |

As shown in Table 6, some of the polymers have shown very high activity against malarial parasites having an $IC_{50}$ in the sub-micromolar range, as presented in the column denoted $IC_{50}$ parasite (µM) (see entries D and E in Table 6 above). The structure-activity relationship conclusion that emerges from this series is that lengthening of the chain increases the anti-malarial activity (reduces the $IC_{50}$). The presence of the alkyl moiety at the N-terminus of the lysine, invariably increases the anti-malarial activity (see, entries G and A, entries H and C and entries I and E in Table 6 above). For some polymers, the amino alkyl adds further activity (see, entries C and D in Table 6 above) but this performance is not always consistent (see, entries A and B and entries E and F in Table 6 above).

There are similar consistencies for the effect of the polymers of the present invention on the MDCK cells. Addition of an alkyl at the N-terminus of the lysine results in a decrease in activity (see, entries G and A, entries H and C, and entries I and E in Table 6 above). The amino alkyl moiety usually results in decreased activity (see, entries A and B, and entries C and D in Table 6 above), but the opposite effect was observed for the longest polymers (see, entries E and F in Table 6 above).

The ratio of $IC_{50}$ is essentially equivalent to the therapeutic ratio. Thus, entries D and E in Table 6 above show the most therapeutically efficient polymers, according to the present invention.

Similar results were obtained with the primary cultures of cardio-fibroblasts (CF) and HepG2 transformed cells (results not shown).

Another series of polymers was tested for anti-malarial activity in order to further investigate the structure-activity relationship with respect to polymer length and hydrophobic moiety residue length.

The results, presented in Table 7 below, wherein "IC50 (µM)" represents the concentration of the tested polymer in µM that is required for 50% inhibition of the growth of the malaria causing parasites, measured as described hereinabove (column 3 in Table 7), indicate that the addition of caprylic acid ($C_8$) to the N-terminus of the lysine residue increases the anti-malarial potency considerably (up to 67 fold), but this amplification diminishes as the chain length increases. Substitution of $C_8$ with lauric acid ($C_{12}$) results in a further increase the anti-malarial potency (up to 20-fold), whereas further substitution at this terminus with ω-aminolauric acid ($NC_{12}$) reverts the potency considerably.

Among the most active polymers in the $C_{12}K(NC_8K)_nNH_2$ group, the anti-malarial potency diminishes with increase polymer length (see, entries 15-21 in Table 7 below). The opposite trend was observed for the non-acylated (at the N-terminus) group $K(NC_8K)_nNH_2$ (see, entries 1-7 in Table 7 below) although they exhibit an overall lower activity. No such consistent trends could be observed for the other groups.

None of the polymers of this series caused lysis of infected RBC at concentrations that are at least 2-fold higher than their respective $IC_{50}$ (data not shown).

TABLE 7

| Entry (SEQ ID NO:) | Polymer | $IC_{50}$ (µM) |
|---|---|---|
| 1 (32) | $KNC_8KNH_2$ | 260 |
| 2 (33) | $K(NC_8K)_2NH_2$ | 180 |
| 3 (34) | $K(NC_8K)_3NH_2$ | 130 |
| 4 (35) | $K(NC_8K)_4NH_2$ | 90 |
| 5 (36) | $K(NC_8K)_5NH_2$ | 84 |
| 6 (37) | $K(NC_8K)_6NH_2$ | 71 |
| 7 (38) | $K(NC_8K)_7NH_2$ | 47 |
| 8 (25) | $C_8KNC_8KNH_2$ | 16 |
| 9 (26) | $C_8K(NC_8K)_2NH_2$ | 2.7 |

TABLE 7-continued

| Entry (SEQ ID NO:) | Polymer | $IC_{50}$ (µM) |
|---|---|---|
| 10 (27) | $C_8K(NC_8K)_3NH_2$ | 14.8 |
| 11 (28) | $C_8K(NC_8K)_4NH_2$ | 48.9 |
| 12 (29) | $C_8K(NC_8K)_5NH_2$ | 44.1 |
| 13 (30) | $C_8K(NC_8K)_6NH_2$ | 30.5 |
| 14 (31) | $C_8K(NC_8K)_7NH_2$ | 37.2 |
| 15 (39) | $C_{12}KNC_8KNH_2$ | 0.38 |
| 16 (40) | $C_{12}K(NC_8K)_2NH_2$ | 0.2 |
| 17 (41) | $C_{12}K(NC_8K)_3NH_2$ | 1.16 |
| 18 (42) | $C_{12}K(NC_8K)_4NH_2$ | 2.43 |
| 19 (43) | $C_{12}K(NC_8K)_5NH_2$ | 5.57 |
| 20 (44) | $C_{12}K(NC_8K)_6NH_2$ | 9.9 |
| 21 (45) | $C_{12}K(NC_8K)_7NH_2$ | 15.8 |
| 22 (46) | $NC_{12}KNC_8KNH_2$ | 120.1 |
| 23 (47) | $NC_{12}K(NC_8K)_2NH_2$ | 99.5 |
| 24 (48) | $NC_{12}K(NC_8K)_3NH_2$ | 93.7 |
| 25 (49) | $NC_{12}K(NC_8K)_4NH_2$ | 72.9 |
| 26 (50) | $NC_{12}K(NC_8K)_5NH_2$ | 70.6 |
| 27 (51) | $NC_{12}K(NC_8K)_6NH_2$ | 66.5 |
| 28 (52) | $NC_{12}K(NC_8K)_7NH_2$ | 89.8 |

The anti-malarial effect of the polymer $C_{12}K(NC_{12}K)_3NH_2$ (see, entry E in Table 6 above) has been tested by exposing parasite cultures at the ring and the trophozoite stages for various lengths of time and different polymer concentrations, the polymer has then been removed and after 48 hours all cultures that were subjected for the different treatments were tested for parasite viability using the hypoxanthine incorporation test.

Figure 10:
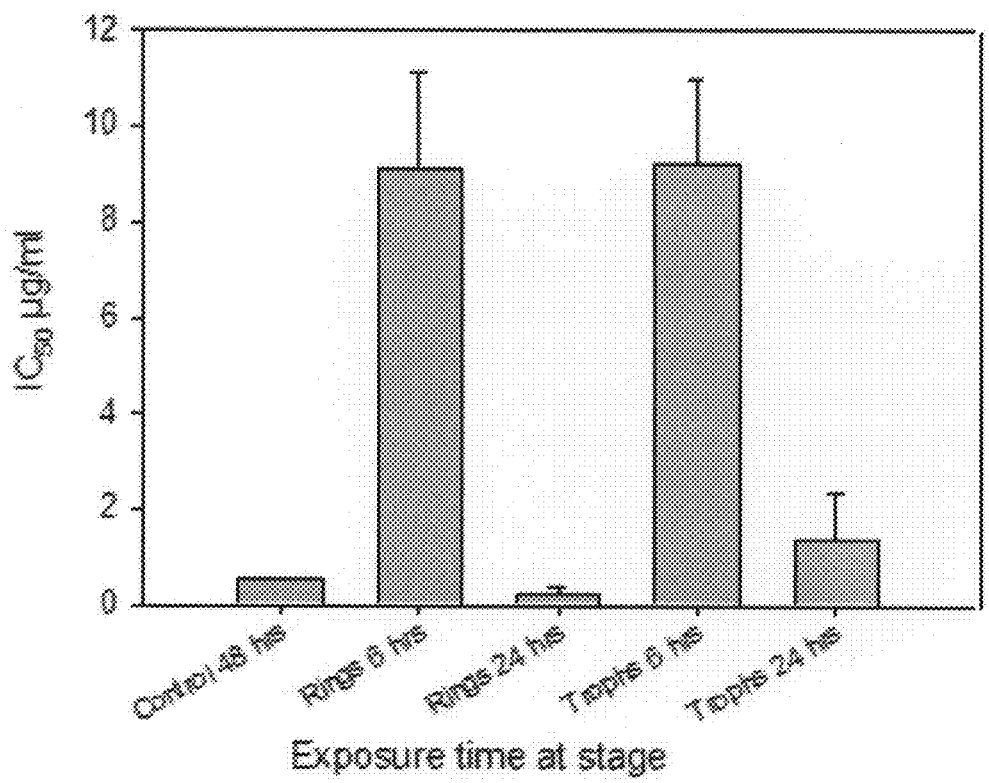
FIG. 10 presents a comparative plot demonstrating the anti-malarial activity of $C_{12}K(NC_{12}K)_3NH_2$ (SEQ ID NO: 56), an exemplary polymer according to the present invention, by showing the effect of time of exposure of the malaria causing parasites to the polymer on the stage-dependent effect on Plasmodium falciparum parasite viability (chloroquine-resistant FCR3 strain versus chloroquine-sensitive NF54 strain)

The $IC_{50}$ for each treatment has been calculated for the chloroquine-resistant FCR3 strain versus chloroquine-sensitive NF54 strain, and the results are presented in FIG. 10. As seen in FIG. 10 the ring stage is more sensitive to the polymer than the trophozoite stage where it also takes a longer time to exert the inhibitory action. It also seems that the effect is cumulative in that the $IC_{50}$ values at 48 hours are lower than those observed with shorter exposure times.

Figure 11:
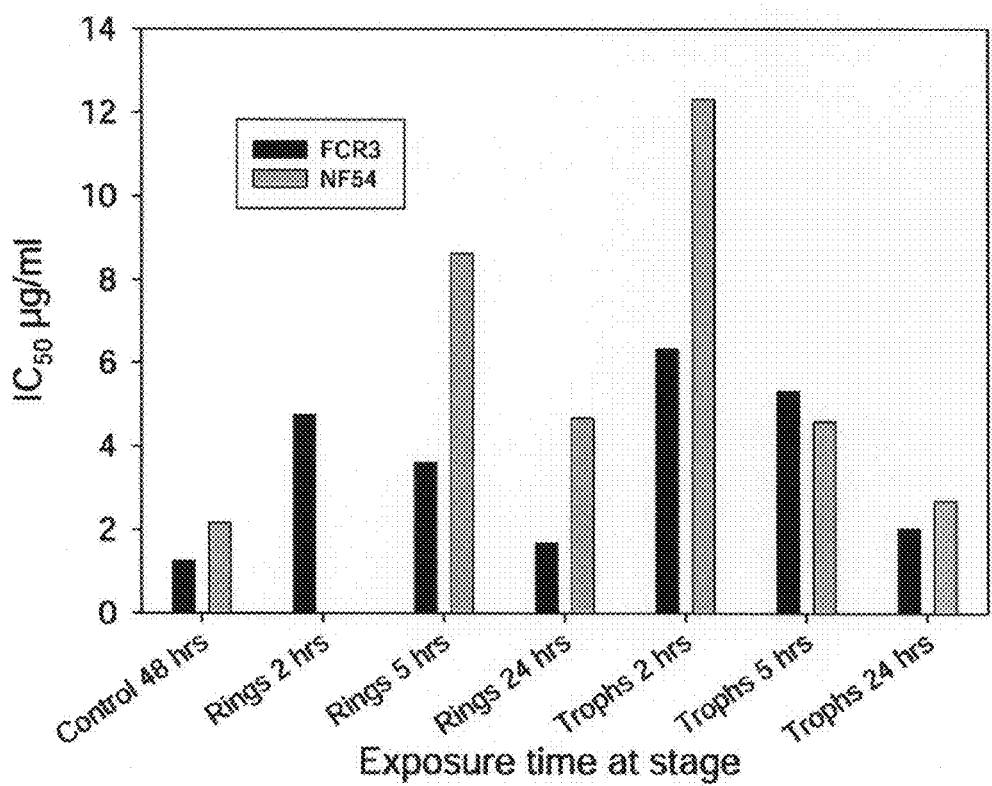
FIG. 11 presents a comparative plot demonstrating the anti-malarial activity of $C_{12}KNC_8KNH_2$ (SEQ ID NO: 39), an exemplary polymer according to the present invention, by showing the effect of time of treatment at different parasite developmental stages with the polymer, on parasite viability.

The effect of time of exposure of parasite cultures to $C_{12}KNC_8KNH_2$ (see, entry 15 in Table 7 above) at different stages on parasite viability is shown in FIG. 11. As can be seen in FIG. 11, the results indicate that ring and trophozoite stages are almost equally sensitive to $C_{12}KNC_8KNH_2$, yet a period of 24 hours is required in order to exert the full inhibitory activity on the rings and more so for the trophozoites stage.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A polymer having an antimicrobial activity and comprising a plurality of positively charged amino acid residues and at least one ω-amino-fatty acid residue, wherein said ω-amino-fatty acid residue is covalently linked to at least two amino acid residues in said plurality of positively charged amino acid residues via the N-alpha of one amino acid residue and via the C-alpha of the other amino acid residue in said at least two amino acid residues, said at least one ω-amino-fatty acid residue being linked to each of said amino acid residues via a peptide bond, the polymer being selected from the group consisting of $C_{12}K(NC_8K)_5NH_2$ (SEQ ID NO:43), $C_{12}K(NC_8K)_7NH_2$ (SEQ ID NO:45) and $C_{12}K(KNC_{12}K)_2NH_2$ (SEQ ID NO:80).

2. A pharmaceutical composition comprising, as an active ingredient, the polymer of claim 1 and a pharmaceutically acceptable carrier.

3. The pharmaceutical composition of claim 2, being packaged in a packaging material and identified in print, in or on said packaging material, for use in the treatment of a medical condition associated with a pathogenic microorganism.

4. The pharmaceutical composition of claim 3, wherein said pathogenic microorganism is selected from the group consisting of a prokaryotic organism, an eubacterium, an archaebacterium, a eukaryotic organism, a yeast, a fungus, an alga, a protozon and a parasite.

5. A method of treating a medical condition associated with a pathogenic microorganism, the method comprising administering to a subject in need thereof a therapeutically effective amount of the polymer of claim 1.

6. The method of claim 5, wherein said pathogenic microorganism is selected from the group consisting of a prokaryotic organism, an eubacterium, an archaebacterium, a eukaryotic organism, a yeast, a fungus, an alga, a protozon and a parasite.

* * * * *

SEQUENCE LISTING

<160> NUMBER OF SEQ ID NOS: 99

<210> SEQ ID NO 1
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: N' 4-carbon fatty acid residue conjugated
      lysine
<220> FEATURE:
<221> NAME/KEY: misc_feature
<222> LOCATION: (2)..(2)
<223> OTHER INFORMATION: Omega-amino-4 carbon fatty acid

<400> SEQUENCE: 1

Lys Xaa Lys
1

<210> SEQ ID NO 2
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: N' 4-carbon fatty acid residue conjugated
      lysine
<220> FEATURE:
<221> NAME/KEY: misc_feature
<222> LOCATION: (2)..(2)
<223> OTHER INFORMATION: Omega-amino-4 carbon fatty acid
<220> FEATURE:
<221> NAME/KEY: misc_feature
<222> LOCATION: (4)..(4)
<223> OTHER INFORMATION: Omega-amino-4 carbon fatty acid

<400> SEQUENCE: 2

Lys Xaa Lys Xaa Lys
1               5

<210> SEQ ID NO 3
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: N' 4-carbon fatty acid residue conjugated
      lysine
<220> FEATURE:
<221> NAME/KEY: misc_feature
<222> LOCATION: (2)..(2)
<223> OTHER INFORMATION: Omega-amino-4 carbon fatty acid
<220> FEATURE:
<221> NAME/KEY: misc_feature

```
<222> LOCATION: (4)..(4)
<223> OTHER INFORMATION: Omega-amino-4 carbon fatty acid
<220> FEATURE:
<221> NAME/KEY: misc_feature
<222> LOCATION: (6)..(6)
<223> OTHER INFORMATION: Omega-amino-4 carbon fatty acid

<400> SEQUENCE: 3

Lys Xaa Lys Xaa Lys Xaa Lys
1               5

<210> SEQ ID NO 4
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: N' 4-carbon fatty acid residue conjugated
      lysine
<220> FEATURE:
<221> NAME/KEY: misc_feature
<222> LOCATION: (2)..(2)
<223> OTHER INFORMATION: Omega-amino-4 carbon fatty acid
<220> FEATURE:
<221> NAME/KEY: misc_feature
<222> LOCATION: (4)..(4)
<223> OTHER INFORMATION: Omega-amino-4 carbon fatty acid
<220> FEATURE:
<221> NAME/KEY: misc_feature
<222> LOCATION: (6)..(6)
<223> OTHER INFORMATION: Omega-amino-4 carbon fatty acid
<220> FEATURE:
<221> NAME/KEY: misc_feature
<222> LOCATION: (8)..(8)
<223> OTHER INFORMATION: Omega-amino-4 carbon fatty acid

<400> SEQUENCE: 4

Lys Xaa Lys Xaa Lys Xaa Lys Xaa Lys
1               5

<210> SEQ ID NO 5
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: N' 4-carbon fatty acid residue conjugated
      lysine
<220> FEATURE:
<221> NAME/KEY: misc_feature
<222> LOCATION: (2)..(2)
<223> OTHER INFORMATION: Omega-amino-4 carbon fatty acid
<220> FEATURE:
<221> NAME/KEY: misc_feature
<222> LOCATION: (4)..(4)
<223> OTHER INFORMATION: Omega-amino-4 carbon fatty acid
<220> FEATURE:
<221> NAME/KEY: misc_feature
<222> LOCATION: (6)..(6)
<223> OTHER INFORMATION: Omega-amino-4 carbon fatty acid
<220> FEATURE:
<221> NAME/KEY: misc_feature
<222> LOCATION: (8)..(8)
```

-continued

```
<223> OTHER INFORMATION: Omega-amino-4 carbon fatty acid
<220> FEATURE:
<221> NAME/KEY: misc_feature
<222> LOCATION: (10)..(10)
<223> OTHER INFORMATION: Omega-amino-4 carbon fatty acid

<400> SEQUENCE: 5

Lys Xaa Lys Xaa Lys Xaa Lys Xaa Lys Xaa Lys
1               5                   10

<210> SEQ ID NO 6
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: N' 4-carbon fatty acid residue conjugated
      lysine
<220> FEATURE:
<221> NAME/KEY: misc_feature
<222> LOCATION: (2)..(2)
<223> OTHER INFORMATION: Omega-amino-4 carbon fatty acid
<220> FEATURE:
<221> NAME/KEY: misc_feature
<222> LOCATION: (4)..(4)
<223> OTHER INFORMATION: Omega-amino-4 carbon fatty acid
<220> FEATURE:
<221> NAME/KEY: misc_feature
<222> LOCATION: (6)..(6)
<223> OTHER INFORMATION: Omega-amino-4 carbon fatty acid
<220> FEATURE:
<221> NAME/KEY: misc_feature
<222> LOCATION: (8)..(8)
<223> OTHER INFORMATION: Omega-amino-4 carbon fatty acid
<220> FEATURE:
<221> NAME/KEY: misc_feature
<222> LOCATION: (10)..(10)
<223> OTHER INFORMATION: Omega-amino-4 carbon fatty acid
<220> FEATURE:
<221> NAME/KEY: misc_feature
<222> LOCATION: (12)..(12)
<223> OTHER INFORMATION: Omega-amino-4 carbon fatty acid

<400> SEQUENCE: 6

Lys Xaa Lys Xaa Lys Xaa Lys Xaa Lys Xaa Lys Xaa Lys
1               5                   10

<210> SEQ ID NO 7
<211> LENGTH: 15
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: N' 4-carbon fatty acid residue conjugated
      lysine
<220> FEATURE:
<221> NAME/KEY: misc_feature
<222> LOCATION: (2)..(2)
<223> OTHER INFORMATION: Omega-amino-4 carbon fatty acid
<220> FEATURE:
<221> NAME/KEY: misc_feature
<222> LOCATION: (4)..(4)
<223> OTHER INFORMATION: Omega-amino-4 carbon fatty acid
```

```
<220> FEATURE:
<221> NAME/KEY: misc_feature
<222> LOCATION: (6)..(6)
<223> OTHER INFORMATION: Omega-amino-4 carbon fatty acid
<220> FEATURE:
<221> NAME/KEY: misc_feature
<222> LOCATION: (8)..(8)
<223> OTHER INFORMATION: Omega-amino-4 carbon fatty acid
<220> FEATURE:
<221> NAME/KEY: misc_feature
<222> LOCATION: (10)..(10)
<223> OTHER INFORMATION: Omega-amino-4 carbon fatty acid
<220> FEATURE:
<221> NAME/KEY: misc_feature
<222> LOCATION: (12)..(12)
<223> OTHER INFORMATION: Omega-amino-4 carbon fatty acid
<220> FEATURE:
<221> NAME/KEY: misc_feature
<222> LOCATION: (14)..(14)
<223> OTHER INFORMATION: Omega-amino-4 carbon fatty acid

<400> SEQUENCE: 7

Lys Xaa Lys Xaa Lys Xaa Lys Xaa Lys Xaa Lys Xaa Lys Xaa Lys
1               5                   10                  15

<210> SEQ ID NO 8
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (2)..(2)
<223> OTHER INFORMATION: Omega-amino-4 carbon fatty acid

<400> SEQUENCE: 8

Lys Xaa Lys
1

<210> SEQ ID NO 9
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (2)..(2)
<223> OTHER INFORMATION: Omega-amino-4 carbon fatty acid
<220> FEATURE:
<221> NAME/KEY: misc_feature
<222> LOCATION: (4)..(4)
<223> OTHER INFORMATION: Omega-amino-4 carbon fatty acid

<400> SEQUENCE: 9

Lys Xaa Lys Xaa Lys
1               5

<210> SEQ ID NO 10
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
```

```
<223> OTHER INFORMATION: C' amidated peptide
<220> FEATURE:
<221> NAME/KEY: misc_feature
<222> LOCATION: (2)..(2)
<223> OTHER INFORMATION: Omega-amino-4 carbon fatty acid
<220> FEATURE:
<221> NAME/KEY: misc_feature
<222> LOCATION: (4)..(4)
<223> OTHER INFORMATION: Omega-amino-4 carbon fatty acid
<220> FEATURE:
<221> NAME/KEY: misc_feature
<222> LOCATION: (6)..(6)
<223> OTHER INFORMATION: Omega-amino-4 carbon fatty acid

<400> SEQUENCE: 10

Lys Xaa Lys Xaa Lys Xaa Lys
1               5

<210> SEQ ID NO 11
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (2)..(2)
<223> OTHER INFORMATION: Omega-amino-4 carbon fatty acid
<220> FEATURE:
<221> NAME/KEY: misc_feature
<222> LOCATION: (4)..(4)
<223> OTHER INFORMATION: Omega-amino-4 carbon fatty acid
<220> FEATURE:
<221> NAME/KEY: misc_feature
<222> LOCATION: (6)..(6)
<223> OTHER INFORMATION: Omega-amino-4 carbon fatty acid
<220> FEATURE:
<221> NAME/KEY: misc_feature
<222> LOCATION: (8)..(8)
<223> OTHER INFORMATION: Omega-amino-4 carbon fatty acid

<400> SEQUENCE: 11

Lys Xaa Lys Xaa Lys Xaa Lys Xaa Lys
1               5

<210> SEQ ID NO 12
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (2)..(2)
<223> OTHER INFORMATION: Omega-amino-4 carbon fatty acid
<220> FEATURE:
<221> NAME/KEY: misc_feature
<222> LOCATION: (4)..(4)
<223> OTHER INFORMATION: Omega-amino-4 carbon fatty acid
<220> FEATURE:
<221> NAME/KEY: misc_feature
<222> LOCATION: (6)..(6)
<223> OTHER INFORMATION: Omega-amino-4 carbon fatty acid
<220> FEATURE:
<221> NAME/KEY: misc_feature
<222> LOCATION: (8)..(8)
<223> OTHER INFORMATION: Omega-amino-4 carbon fatty acid
<220> FEATURE:
<221> NAME/KEY: misc_feature
```

```
<222> LOCATION: (10)..(10)
<223> OTHER INFORMATION: Omega-amino-4 carbon fatty acid

<400> SEQUENCE: 12

Lys Xaa Lys Xaa Lys Xaa Lys Xaa Lys Xaa Lys
1               5                   10

<210> SEQ ID NO 13
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (2)..(2)
<223> OTHER INFORMATION: Omega-amino-4 carbon fatty acid
<220> FEATURE:
<221> NAME/KEY: misc_feature
<222> LOCATION: (4)..(4)
<223> OTHER INFORMATION: Omega-amino-4 carbon fatty acid
<220> FEATURE:
<221> NAME/KEY: misc_feature
<222> LOCATION: (6)..(6)
<223> OTHER INFORMATION: Omega-amino-4 carbon fatty acid
<220> FEATURE:
<221> NAME/KEY: misc_feature
<222> LOCATION: (8)..(8)
<223> OTHER INFORMATION: Omega-amino-4 carbon fatty acid
<220> FEATURE:
<221> NAME/KEY: misc_feature
<222> LOCATION: (10)..(10)
<223> OTHER INFORMATION: Omega-amino-4 carbon fatty acid
<220> FEATURE:
<221> NAME/KEY: misc_feature
<222> LOCATION: (12)..(12)
<223> OTHER INFORMATION: Omega-amino-4 carbon fatty acid

<400> SEQUENCE: 13

Lys Xaa Lys Xaa Lys Xaa Lys Xaa Lys Xaa Lys Xaa Lys
1               5                   10

<210> SEQ ID NO 14
<211> LENGTH: 15
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (2)..(2)
<223> OTHER INFORMATION: Omega-amino-4 carbon fatty acid
<220> FEATURE:
<221> NAME/KEY: misc_feature
<222> LOCATION: (4)..(4)
<223> OTHER INFORMATION: Omega-amino-4 carbon fatty acid
<220> FEATURE:
<221> NAME/KEY: misc_feature
<222> LOCATION: (6)..(6)
<223> OTHER INFORMATION: Omega-amino-4 carbon fatty acid
<220> FEATURE:
<221> NAME/KEY: misc_feature
<222> LOCATION: (8)..(8)
<223> OTHER INFORMATION: Omega-amino-4 carbon fatty acid
<220> FEATURE:
<221> NAME/KEY: misc_feature
<222> LOCATION: (10)..(10)
<223> OTHER INFORMATION: Omega-amino-4 carbon fatty acid
<220> FEATURE:
```

```
<221> NAME/KEY: misc_feature
<222> LOCATION: (12)..(12)
<223> OTHER INFORMATION: Omega-amino-4 carbon fatty acid
<220> FEATURE:
<221> NAME/KEY: misc_feature
<222> LOCATION: (14)..(14)
<223> OTHER INFORMATION: Omega-amino-4 carbon fatty acid

<400> SEQUENCE: 14

Lys Xaa Lys Xaa Lys Xaa Lys Xaa Lys Xaa Lys Xaa Lys Xaa Lys
1               5                   10                  15

<210> SEQ ID NO 15
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: N' 12-carbon fatty acid residue conjugated
      lysine
<220> FEATURE:
<221> NAME/KEY: misc_feature
<222> LOCATION: (2)..(2)
<223> OTHER INFORMATION: Omega-amino-4 carbon fatty acid

<400> SEQUENCE: 15

Lys Xaa Lys
1

<210> SEQ ID NO 16
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amine
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: N' 12-carbon fatty acid residue conjugated
      lysine
<220> FEATURE:
<221> NAME/KEY: misc_feature
<222> LOCATION: (2)..(2)
<223> OTHER INFORMATION: Omega-amino-4 carbon fatty acid
<220> FEATURE:
<221> NAME/KEY: misc_feature
<222> LOCATION: (4)..(4)
<223> OTHER INFORMATION: Omega-amino-4 carbon fatty acid

<400> SEQUENCE: 16

Lys Xaa Lys Xaa Lys
1               5

<210> SEQ ID NO 17
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
```

```
<222> LOCATION: (1)..(1)
<223> OTHER INFORMATION: N' 12-carbon fatty acid residue conjugated
      lysine
<220> FEATURE:
<221> NAME/KEY: misc_feature
<222> LOCATION: (2)..(2)
<223> OTHER INFORMATION: Omega-amino-4 carbon fatty acid
<220> FEATURE:
<221> NAME/KEY: misc_feature
<222> LOCATION: (4)..(4)
<223> OTHER INFORMATION: Omega-amino-4 carbon fatty acid
<220> FEATURE:
<221> NAME/KEY: misc_feature
<222> LOCATION: (6)..(6)
<223> OTHER INFORMATION: Omega-amino-4 carbon fatty acid

<400> SEQUENCE: 17

Lys Xaa Lys Xaa Lys Xaa Lys
1               5

<210> SEQ ID NO 18
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: N' 12-carbon fatty acid residue conjugated
      lysine
<220> FEATURE:
<221> NAME/KEY: misc_feature
<222> LOCATION: (2)..(2)
<223> OTHER INFORMATION: Omega-amino-4 carbon fatty acid
<220> FEATURE:
<221> NAME/KEY: misc_feature
<222> LOCATION: (4)..(4)
<223> OTHER INFORMATION: Omega-amino-4 carbon fatty acid
<220> FEATURE:
<221> NAME/KEY: misc_feature
<222> LOCATION: (6)..(6)
<223> OTHER INFORMATION: Omega-amino-4 carbon fatty acid
<220> FEATURE:
<221> NAME/KEY: misc_feature
<222> LOCATION: (8)..(8)
<223> OTHER INFORMATION: Omega-amino-4 carbon fatty acid

<400> SEQUENCE: 18

Lys Xaa Lys Xaa Lys Xaa Lys Xaa Lys
1               5

<210> SEQ ID NO 19
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: N' 12-carbon fatty acid residue conjugated
      lysine
<220> FEATURE:
<221> NAME/KEY: misc_feature
<222> LOCATION: (2)..(2)
<223> OTHER INFORMATION: Omega-amino-4 carbon fatty acid
<220> FEATURE:
<221> NAME/KEY: misc_feature
```

```
<222> LOCATION: (4)..(4)
<223> OTHER INFORMATION: Omega-amino-4 carbon fatty acid
<220> FEATURE:
<221> NAME/KEY: misc_feature
<222> LOCATION: (6)..(6)
<223> OTHER INFORMATION: Omega-amino-4 carbon fatty acid
<220> FEATURE:
<221> NAME/KEY: misc_feature
<222> LOCATION: (8)..(8)
<223> OTHER INFORMATION: Omega-amino-4 carbon fatty acid
<220> FEATURE:
<221> NAME/KEY: misc_feature
<222> LOCATION: (10)..(10)
<223> OTHER INFORMATION: Omega-amino-4 carbon fatty acid

<400> SEQUENCE: 19

Lys Xaa Lys Xaa Lys Xaa Lys Xaa Lys Xaa Lys
1               5                   10

<210> SEQ ID NO 20
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: N' 12-carbon fatty acid residue conjugated
      lysine
<220> FEATURE:
<221> NAME/KEY: misc_feature
<222> LOCATION: (2)..(2)
<223> OTHER INFORMATION: Omega-amino-4 carbon fatty acid
<220> FEATURE:
<221> NAME/KEY: misc_feature
<222> LOCATION: (4)..(4)
<223> OTHER INFORMATION: Omega-amino-4 carbon fatty acid
<220> FEATURE:
<221> NAME/KEY: misc_feature
<222> LOCATION: (6)..(6)
<223> OTHER INFORMATION: Omega-amino-4 carbon fatty acid
<220> FEATURE:
<221> NAME/KEY: misc_feature
<222> LOCATION: (8)..(8)
<223> OTHER INFORMATION: Omega-amino-4 carbon fatty acid
<220> FEATURE:
<221> NAME/KEY: misc_feature
<222> LOCATION: (10)..(10)
<223> OTHER INFORMATION: Omega-amino-4 carbon fatty acid
<220> FEATURE:
<221> NAME/KEY: misc_feature
<222> LOCATION: (12)..(12)
<223> OTHER INFORMATION: Omega-amino-4 carbon fatty acid

<400> SEQUENCE: 20

Lys Xaa Lys Xaa Lys Xaa Lys Xaa Lys Xaa Lys Xaa Lys
1               5                   10

<210> SEQ ID NO 21
<211> LENGTH: 15
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: N' 12-carbon fatty acid residue conjugated
```

```
                lysine
<220> FEATURE:
<221> NAME/KEY: misc_feature
<222> LOCATION: (2)..(2)
<223> OTHER INFORMATION: Omega-amino-4 carbon fatty acid
<220> FEATURE:
<221> NAME/KEY: misc_feature
<222> LOCATION: (4)..(4)
<223> OTHER INFORMATION: Omega-amino-4 carbon fatty acid
<220> FEATURE:
<221> NAME/KEY: misc_feature
<222> LOCATION: (6)..(6)
<223> OTHER INFORMATION: Omega-amino-4 carbon fatty acid
<220> FEATURE:
<221> NAME/KEY: misc_feature
<222> LOCATION: (8)..(8)
<223> OTHER INFORMATION: Omega-amino-4 carbon fatty acid
<220> FEATURE:
<221> NAME/KEY: misc_feature
<222> LOCATION: (10)..(10)
<223> OTHER INFORMATION: Omega-amino-4 carbon fatty acid
<220> FEATURE:
<221> NAME/KEY: misc_feature
<222> LOCATION: (12)..(12)
<223> OTHER INFORMATION: Omega-amino-4 carbon fatty acid
<220> FEATURE:
<221> NAME/KEY: misc_feature
<222> LOCATION: (14)..(14)
<223> OTHER INFORMATION: Omega-amino-4 carbon fatty acid

<400> SEQUENCE: 21

Lys Xaa Lys Xaa Lys Xaa Lys Xaa Lys Xaa Lys Xaa Lys Xaa Lys
1               5                   10                  15

<210> SEQ ID NO 22
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: Omega-amino-12 carbon fatty acid
<220> FEATURE:
<221> NAME/KEY: misc_feature
<222> LOCATION: (3)..(3)
<223> OTHER INFORMATION: Omega-amino-4 carbon fatty acid
<220> FEATURE:
<221> NAME/KEY: misc_feature
<222> LOCATION: (5)..(5)
<223> OTHER INFORMATION: Omega-amino-4 carbon fatty acid
<220> FEATURE:
<221> NAME/KEY: misc_feature
<222> LOCATION: (7)..(7)
<223> OTHER INFORMATION: Omega-amino-4 carbon fatty acid
<220> FEATURE:
<221> NAME/KEY: misc_feature
<222> LOCATION: (9)..(9)
<223> OTHER INFORMATION: Omega-amino-4 carbon fatty acid
<220> FEATURE:
<221> NAME/KEY: misc_feature
<222> LOCATION: (11)..(11)
<223> OTHER INFORMATION: Omega-amino-4 carbon fatty acid

<400> SEQUENCE: 22

Xaa Lys Xaa Lys Xaa Lys Xaa Lys Xaa Lys Xaa Lys
1               5                   10

<210> SEQ ID NO 23
<211> LENGTH: 14
<212> TYPE: PRT
```

<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: Omega-amino-12 carbon fatty acid
<220> FEATURE:
<221> NAME/KEY: misc_feature
<222> LOCATION: (3)..(3)
<223> OTHER INFORMATION: Omega-amino-4 carbon fatty acid
<220> FEATURE:
<221> NAME/KEY: misc_feature
<222> LOCATION: (5)..(5)
<223> OTHER INFORMATION: Omega-amino-4 carbon fatty acid
<220> FEATURE:
<221> NAME/KEY: misc_feature
<222> LOCATION: (7)..(7)
<223> OTHER INFORMATION: Omega-amino-4 carbon fatty acid
<220> FEATURE:
<221> NAME/KEY: misc_feature
<222> LOCATION: (9)..(9)
<223> OTHER INFORMATION: Omega-amino-4 carbon fatty acid
<220> FEATURE:
<221> NAME/KEY: misc_feature
<222> LOCATION: (11)..(11)
<223> OTHER INFORMATION: Omega-amino-4 carbon fatty acid
<220> FEATURE:
<221> NAME/KEY: misc_feature
<222> LOCATION: (13)..(13)
<223> OTHER INFORMATION: Omega-amino-4 carbon fatty acid

<400> SEQUENCE: 23

Xaa Lys Xaa Lys Xaa Lys Xaa Lys Xaa Lys Xaa Lys Xaa Lys
1               5                   10

<210> SEQ ID NO 24
<211> LENGTH: 16
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: Omega-amino-12 carbon fatty acid
<220> FEATURE:
<221> NAME/KEY: misc_feature
<222> LOCATION: (3)..(3)
<223> OTHER INFORMATION: Omega-amino-4 carbon fatty acid
<220> FEATURE:
<221> NAME/KEY: misc_feature
<222> LOCATION: (5)..(5)
<223> OTHER INFORMATION: Omega-amino-4 carbon fatty acid
<220> FEATURE:
<221> NAME/KEY: misc_feature
<222> LOCATION: (7)..(7)
<223> OTHER INFORMATION: Omega-amino-4 carbon fatty acid
<220> FEATURE:
<221> NAME/KEY: misc_feature
<222> LOCATION: (9)..(9)
<223> OTHER INFORMATION: Omega-amino-4 carbon fatty acid
<220> FEATURE:
<221> NAME/KEY: misc_feature
<222> LOCATION: (11)..(11)
<223> OTHER INFORMATION: Omega-amino-4 carbon fatty acid
<220> FEATURE:
<221> NAME/KEY: misc_feature
<222> LOCATION: (13)..(13)
<223> OTHER INFORMATION: Omega-amino-4 carbon fatty acid
<220> FEATURE:

```
<221> NAME/KEY: misc_feature
<222> LOCATION: (15)..(15)
<223> OTHER INFORMATION: Omega-amino-4 carbon fatty acid

<400> SEQUENCE: 24

Xaa Lys Xaa Lys Xaa Lys Xaa Lys Xaa Lys Xaa Lys Xaa Lys Xaa Lys
1               5                   10                  15

<210> SEQ ID NO 25
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: N' 8-carbon fatty acid residue conjugated
      lysine
<220> FEATURE:
<221> NAME/KEY: misc_feature
<222> LOCATION: (2)..(2)
<223> OTHER INFORMATION: Omega-amino-8 carbon fatty acid

<400> SEQUENCE: 25

Lys Xaa Lys
1

<210> SEQ ID NO 26
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: N' 8-carbon fatty acid residue conjugated
      lysine
<220> FEATURE:
<221> NAME/KEY: misc_feature
<222> LOCATION: (2)..(2)
<223> OTHER INFORMATION: Omega-amino-8 carbon fatty acid
<220> FEATURE:
<221> NAME/KEY: misc_feature
<222> LOCATION: (4)..(4)
<223> OTHER INFORMATION: Omega-amino-8 carbon fatty acid

<400> SEQUENCE: 26

Lys Xaa Lys Xaa Lys
1               5

<210> SEQ ID NO 27
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: N' 8-carbon fatty acid residue conjugated
      lysine
<220> FEATURE:
```

```
<221> NAME/KEY: misc_feature
<222> LOCATION: (2)..(2)
<223> OTHER INFORMATION: Omega-amino-8 carbon fatty acid
<220> FEATURE:
<221> NAME/KEY: misc_feature
<222> LOCATION: (4)..(4)
<223> OTHER INFORMATION: Omega-amino-8 carbon fatty acid
<220> FEATURE:
<221> NAME/KEY: misc_feature
<222> LOCATION: (6)..(6)
<223> OTHER INFORMATION: Omega-amino-8 carbon fatty acid

<400> SEQUENCE: 27

Lys Xaa Lys Xaa Lys Xaa Lys
1               5

<210> SEQ ID NO 28
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: N' 8-carbon fatty acid residue conjugated
      lysine
<220> FEATURE:
<221> NAME/KEY: misc_feature
<222> LOCATION: (2)..(2)
<223> OTHER INFORMATION: Omega-amino-8 carbon fatty acid
<220> FEATURE:
<221> NAME/KEY: misc_feature
<222> LOCATION: (4)..(4)
<223> OTHER INFORMATION: Omega-amino-8 carbon fatty acid
<220> FEATURE:
<221> NAME/KEY: misc_feature
<222> LOCATION: (6)..(6)
<223> OTHER INFORMATION: Omega-amino-8 carbon fatty acid
<220> FEATURE:
<221> NAME/KEY: misc_feature
<222> LOCATION: (8)..(8)
<223> OTHER INFORMATION: Omega-amino-8 carbon fatty acid

<400> SEQUENCE: 28

Lys Xaa Lys Xaa Lys Xaa Lys Xaa Lys
1               5

<210> SEQ ID NO 29
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: N' 8-carbon fatty acid residue conjugated
      lysine
<220> FEATURE:
<221> NAME/KEY: misc_feature
<222> LOCATION: (2)..(2)
<223> OTHER INFORMATION: Omega-amino-8 carbon fatty acid
<220> FEATURE:
<221> NAME/KEY: misc_feature
<222> LOCATION: (4)..(4)
<223> OTHER INFORMATION: Omega-amino-8 carbon fatty acid
<220> FEATURE:
<221> NAME/KEY: misc_feature
```

```
<222> LOCATION: (6)..(6)
<223> OTHER INFORMATION: Omega-amino-8 carbon fatty acid
<220> FEATURE:
<221> NAME/KEY: misc_feature
<222> LOCATION: (8)..(8)
<223> OTHER INFORMATION: Omega-amino-8 carbon fatty acid
<220> FEATURE:
<221> NAME/KEY: misc_feature
<222> LOCATION: (10)..(10)
<223> OTHER INFORMATION: Omega-amino-8 carbon fatty acid

<400> SEQUENCE: 29

Lys Xaa Lys Xaa Lys Xaa Lys Xaa Lys Xaa Lys
1               5                   10

<210> SEQ ID NO 30
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: N' 8-carbon fatty acid residue conjugated
      lysine
<220> FEATURE:
<221> NAME/KEY: misc_feature
<222> LOCATION: (2)..(2)
<223> OTHER INFORMATION: Omega-amino-8 carbon fatty acid
<220> FEATURE:
<221> NAME/KEY: misc_feature
<222> LOCATION: (4)..(4)
<223> OTHER INFORMATION: Omega-amino-8 carbon fatty acid
<220> FEATURE:
<221> NAME/KEY: misc_feature
<222> LOCATION: (6)..(6)
<223> OTHER INFORMATION: Omega-amino-8 carbon fatty acid
<220> FEATURE:
<221> NAME/KEY: misc_feature
<222> LOCATION: (8)..(8)
<223> OTHER INFORMATION: Omega-amino-8 carbon fatty acid
<220> FEATURE:
<221> NAME/KEY: misc_feature
<222> LOCATION: (10)..(10)
<223> OTHER INFORMATION: Omega-amino-8 carbon fatty acid
<220> FEATURE:
<221> NAME/KEY: misc_feature
<222> LOCATION: (12)..(12)
<223> OTHER INFORMATION: Omega-amino-8 carbon fatty acid

<400> SEQUENCE: 30

Lys Xaa Lys Xaa Lys Xaa Lys Xaa Lys Xaa Lys Xaa Lys
1               5                   10

<210> SEQ ID NO 31
<211> LENGTH: 15
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: N' 8-carbon fatty acid residue conjugated
      lysine
<220> FEATURE:
<221> NAME/KEY: misc_feature
<222> LOCATION: (2)..(2)
```

```
<223> OTHER INFORMATION: Omega-amino-8 carbon fatty acid
<220> FEATURE:
<221> NAME/KEY: misc_feature
<222> LOCATION: (4)..(4)
<223> OTHER INFORMATION: Omega-amino-8 carbon fatty acid
<220> FEATURE:
<221> NAME/KEY: misc_feature
<222> LOCATION: (6)..(6)
<223> OTHER INFORMATION: Omega-amino-8 carbon fatty acid
<220> FEATURE:
<221> NAME/KEY: misc_feature
<222> LOCATION: (8)..(8)
<223> OTHER INFORMATION: Omega-amino-8 carbon fatty acid
<220> FEATURE:
<221> NAME/KEY: misc_feature
<222> LOCATION: (10)..(10)
<223> OTHER INFORMATION: Omega-amino-8 carbon fatty acid
<220> FEATURE:
<221> NAME/KEY: misc_feature
<222> LOCATION: (12)..(12)
<223> OTHER INFORMATION: Omega-amino-8 carbon fatty acid
<220> FEATURE:
<221> NAME/KEY: misc_feature
<222> LOCATION: (14)..(14)
<223> OTHER INFORMATION: Omega-amino-8 carbon fatty acid

<400> SEQUENCE: 31

Lys Xaa Lys Xaa Lys Xaa Lys Xaa Lys Xaa Lys Xaa Lys Xaa Lys
1               5                   10                  15

<210> SEQ ID NO 32
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (2)..(2)
<223> OTHER INFORMATION: Omega-amino-8 carbon fatty acid

<400> SEQUENCE: 32

Lys Xaa Lys
1

<210> SEQ ID NO 33
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (2)..(2)
<223> OTHER INFORMATION: Omega-amino-8 carbon fatty acid
<220> FEATURE:
<221> NAME/KEY: misc_feature
<222> LOCATION: (4)..(4)
<223> OTHER INFORMATION: Omega-amino-8 carbon fatty acid

<400> SEQUENCE: 33

Lys Xaa Lys Xaa Lys
1               5

<210> SEQ ID NO 34
<211> LENGTH: 7
<212> TYPE: PRT
```

```
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (2)..(2)
<223> OTHER INFORMATION: Omega-amino-8 carbon fatty acid
<220> FEATURE:
<221> NAME/KEY: misc_feature
<222> LOCATION: (4)..(4)
<223> OTHER INFORMATION: Omega-amino-8 carbon fatty acid
<220> FEATURE:
<221> NAME/KEY: misc_feature
<222> LOCATION: (6)..(6)
<223> OTHER INFORMATION: Omega-amino-8 carbon fatty acid

<400> SEQUENCE: 34

Lys Xaa Lys Xaa Lys Xaa Lys
1               5

<210> SEQ ID NO 35
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (2)..(2)
<223> OTHER INFORMATION: Omega-amino-8 carbon fatty acid
<220> FEATURE:
<221> NAME/KEY: misc_feature
<222> LOCATION: (4)..(4)
<223> OTHER INFORMATION: Omega-amino-8 carbon fatty acid
<220> FEATURE:
<221> NAME/KEY: misc_feature
<222> LOCATION: (6)..(6)
<223> OTHER INFORMATION: Omega-amino-8 carbon fatty acid
<220> FEATURE:
<221> NAME/KEY: misc_feature
<222> LOCATION: (8)..(8)
<223> OTHER INFORMATION: Omega-amino-8 carbon fatty acid

<400> SEQUENCE: 35

Lys Xaa Lys Xaa Lys Xaa Lys Xaa Lys
1               5

<210> SEQ ID NO 36
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (2)..(2)
<223> OTHER INFORMATION: Omega-amino-8 carbon fatty acid
<220> FEATURE:
<221> NAME/KEY: misc_feature
<222> LOCATION: (4)..(4)
<223> OTHER INFORMATION: Omega-amino-8 carbon fatty acid
<220> FEATURE:
<221> NAME/KEY: misc_feature
<222> LOCATION: (6)..(6)
<223> OTHER INFORMATION: Omega-amino-8 carbon fatty acid
<220> FEATURE:
```

```
<221> NAME/KEY: misc_feature
<222> LOCATION: (8)..(8)
<223> OTHER INFORMATION: Omega-amino-8 carbon fatty acid
<220> FEATURE:
<221> NAME/KEY: misc_feature
<222> LOCATION: (10)..(10)
<223> OTHER INFORMATION: Omega-amino-8 carbon fatty acid

<400> SEQUENCE: 36

Lys Xaa Lys Xaa Lys Xaa Lys Xaa Lys Xaa Lys
1               5                   10

<210> SEQ ID NO 37
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (2)..(2)
<223> OTHER INFORMATION: Omega-amino-8 carbon fatty acid
<220> FEATURE:
<221> NAME/KEY: misc_feature
<222> LOCATION: (4)..(4)
<223> OTHER INFORMATION: Omega-amino-8 carbon fatty acid
<220> FEATURE:
<221> NAME/KEY: misc_feature
<222> LOCATION: (6)..(6)
<223> OTHER INFORMATION: Omega-amino-8 carbon fatty acid
<220> FEATURE:
<221> NAME/KEY: misc_feature
<222> LOCATION: (8)..(8)
<223> OTHER INFORMATION: Omega-amino-8 carbon fatty acid
<220> FEATURE:
<221> NAME/KEY: misc_feature
<222> LOCATION: (10)..(10)
<223> OTHER INFORMATION: Omega-amino-8 carbon fatty acid
<220> FEATURE:
<221> NAME/KEY: misc_feature
<222> LOCATION: (12)..(12)
<223> OTHER INFORMATION: Omega-amino-8 carbon fatty acid

<400> SEQUENCE: 37

Lys Xaa Lys Xaa Lys Xaa Lys Xaa Lys Xaa Lys Xaa Lys
1               5                   10

<210> SEQ ID NO 38
<211> LENGTH: 15
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (2)..(2)
<223> OTHER INFORMATION: Omega-amino-8 carbon fatty acid
<220> FEATURE:
<221> NAME/KEY: misc_feature
<222> LOCATION: (4)..(4)
<223> OTHER INFORMATION: Omega-amino-8 carbon fatty acid
<220> FEATURE:
<221> NAME/KEY: misc_feature
<222> LOCATION: (6)..(6)
<223> OTHER INFORMATION: Omega-amino-8 carbon fatty acid
<220> FEATURE:
<221> NAME/KEY: misc_feature
<222> LOCATION: (8)..(8)
<223> OTHER INFORMATION: Omega-amino-8 carbon fatty acid
```

```
<220> FEATURE:
<221> NAME/KEY: misc_feature
<222> LOCATION: (10)..(10)
<223> OTHER INFORMATION: Omega-amino-8 carbon fatty acid
<220> FEATURE:
<221> NAME/KEY: misc_feature
<222> LOCATION: (12)..(12)
<223> OTHER INFORMATION: Omega-amino-8 carbon fatty acid
<220> FEATURE:
<221> NAME/KEY: misc_feature
<222> LOCATION: (14)..(14)
<223> OTHER INFORMATION: Omega-amino-8 carbon fatty acid

<400> SEQUENCE: 38

Lys Xaa Lys Xaa Lys Xaa Lys Xaa Lys Xaa Lys Xaa Lys Xaa Lys
1               5                   10                  15

<210> SEQ ID NO 39
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: N' 12-carbon fatty acid residue conjugated
      lysine
<220> FEATURE:
<221> NAME/KEY: misc_feature
<222> LOCATION: (2)..(2)
<223> OTHER INFORMATION: Omega-amino-8 carbon fatty acid

<400> SEQUENCE: 39

Lys Xaa Lys
1

<210> SEQ ID NO 40
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: N' 12-carbon fatty acid residue conjugated
      lysine
<220> FEATURE:
<221> NAME/KEY: misc_feature
<222> LOCATION: (2)..(2)
<223> OTHER INFORMATION: Omega-amino-8 carbon fatty acid
<220> FEATURE:
<221> NAME/KEY: misc_feature
<222> LOCATION: (4)..(4)
<223> OTHER INFORMATION: Omega-amino-8 carbon fatty acid

<400> SEQUENCE: 40

Lys Xaa Lys Xaa Lys
1               5

<210> SEQ ID NO 41
<211> LENGTH: 7
<212> TYPE: PRT
<213> ORGANISM: Artificial sequence
<220> FEATURE:
<223> OTHER INFORMATION: Synthetic peptide
```

```
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: N' 12-carbon fatty acid residue conjugated
      lysine
<220> FEATURE:
<221> NAME/KEY: misc_feature
<222> LOCATION: (2)..(2)
<223> OTHER INFORMATION: Omega-amino-8 carbon fatty acid
<220> FEATURE:
<221> NAME/KEY: misc_feature
<222> LOCATION: (4)..(4)
<223> OTHER INFORMATION: Omega-amino-8 carbon fatty acid
<220> FEATURE:
<221> NAME/KEY: misc_feature
<222> LOCATION: (6)..(6)
<223> OTHER INFORMATION: Omega-amino-8 carbon fatty acid

<400> SEQUENCE: 41

Lys Xaa Lys Xaa Lys Xaa Lys
1               5

<210> SEQ ID NO 42
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: N' 12-carbon fatty acid residue conjugated
      lysine
<220> FEATURE:
<221> NAME/KEY: misc_feature
<222> LOCATION: (2)..(2)
<223> OTHER INFORMATION: Omega-amino-8 carbon fatty acid
<220> FEATURE:
<221> NAME/KEY: misc_feature
<222> LOCATION: (4)..(4)
<223> OTHER INFORMATION: Omega-amino-8 carbon fatty acid
<220> FEATURE:
<221> NAME/KEY: misc_feature
<222> LOCATION: (6)..(6)
<223> OTHER INFORMATION: Omega-amino-8 carbon fatty acid
<220> FEATURE:
<221> NAME/KEY: misc_feature
<222> LOCATION: (8)..(8)
<223> OTHER INFORMATION: Omega-amino-8 carbon fatty acid

<400> SEQUENCE: 42

Lys Xaa Lys Xaa Lys Xaa Lys Xaa Lys
1               5

<210> SEQ ID NO 43
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: N' 12-carbon fatty acid residue conjugated
      lysine
<220> FEATURE:
```

```
<221> NAME/KEY: misc_feature
<222> LOCATION: (2)..(2)
<223> OTHER INFORMATION: Omega-amino-8 carbon fatty acid
<220> FEATURE:
<221> NAME/KEY: misc_feature
<222> LOCATION: (4)..(4)
<223> OTHER INFORMATION: Omega-amino-8 carbon fatty acid
<220> FEATURE:
<221> NAME/KEY: misc_feature
<222> LOCATION: (6)..(6)
<223> OTHER INFORMATION: Omega-amino-8 carbon fatty acid
<220> FEATURE:
<221> NAME/KEY: misc_feature
<222> LOCATION: (8)..(8)
<223> OTHER INFORMATION: Omega-amino-8 carbon fatty acid
<220> FEATURE:
<221> NAME/KEY: misc_feature
<222> LOCATION: (10)..(10)
<223> OTHER INFORMATION: Omega-amino-8 carbon fatty acid

<400> SEQUENCE: 43

Lys Xaa Lys Xaa Lys Xaa Lys Xaa Lys Xaa Lys
1               5                   10

<210> SEQ ID NO 44
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: N' 12-carbon fatty acid residue conjugated
      lysine
<220> FEATURE:
<221> NAME/KEY: misc_feature
<222> LOCATION: (2)..(2)
<223> OTHER INFORMATION: Omega-amino-8 carbon fatty acid
<220> FEATURE:
<221> NAME/KEY: misc_feature
<222> LOCATION: (4)..(4)
<223> OTHER INFORMATION: Omega-amino-8 carbon fatty acid
<220> FEATURE:
<221> NAME/KEY: misc_feature
<222> LOCATION: (6)..(6)
<223> OTHER INFORMATION: Omega-amino-8 carbon fatty acid
<220> FEATURE:
<221> NAME/KEY: misc_feature
<222> LOCATION: (8)..(8)
<223> OTHER INFORMATION: Omega-amino-8 carbon fatty acid
<220> FEATURE:
<221> NAME/KEY: misc_feature
<222> LOCATION: (10)..(10)
<223> OTHER INFORMATION: Omega-amino-8 carbon fatty acid
<220> FEATURE:
<221> NAME/KEY: misc_feature
<222> LOCATION: (12)..(12)
<223> OTHER INFORMATION: Omega-amino-8 carbon fatty acid

<400> SEQUENCE: 44

Lys Xaa Lys Xaa Lys Xaa Lys Xaa Lys Xaa Lys Xaa Lys
1               5                   10

<210> SEQ ID NO 45
<211> LENGTH: 15
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
```

```
<223> OTHER INFORMATION: C' amidated peptide
<220> FEATURE:
<221> NAME/KEY: misc_feature
<222> LOCATION: (1)..(1)
<223> OTHER INFORMATION: N' 12-carbon fatty acid residue conjugated
      lysine
<220> FEATURE:
<221> NAME/KEY: misc_feature
<222> LOCATION: (2)..(2)
<223> OTHER INFORMATION: Omega-amino-8 carbon fatty acid
<220> FEATURE:
<221> NAME/KEY: misc_feature
<222> LOCATION: (4)..(4)
<223> OTHER INFORMATION: Omega-amino-8 carbon fatty acid
<220> FEATURE:
<221> NAME/KEY: misc_feature
<222> LOCATION: (6)..(6)
<223> OTHER INFORMATION: Omega-amino-8 carbon fatty acid
<220> FEATURE:
<221> NAME/KEY: misc_feature
<222> LOCATION: (8)..(8)
<223> OTHER INFORMATION: Omega-amino-8 carbon fatty acid
<220> FEATURE:
<221> NAME/KEY: misc_feature
<222> LOCATION: (10)..(10)
<223> OTHER INFORMATION: Omega-amino-8 carbon fatty acid
<220> FEATURE:
<221> NAME/KEY: misc_feature
<222> LOCATION: (12)..(12)
<223> OTHER INFORMATION: Omega-amino-8 carbon fatty acid
<220> FEATURE:
<221> NAME/KEY: misc_feature
<222> LOCATION: (14)..(14)
<223> OTHER INFORMATION: Omega-amino-8 carbon fatty acid

<400> SEQUENCE: 45

Lys Xaa Lys Xaa Lys Xaa Lys Xaa Lys Xaa Lys Xaa Lys Xaa Lys
1               5                   10                  15

<210> SEQ ID NO 46
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: Omega-amino-12 carbon fatty acid
<220> FEATURE:
<221> NAME/KEY: misc_feature
<222> LOCATION: (3)..(3)
<223> OTHER INFORMATION: Omega-amino-8 carbon fatty acid

<400> SEQUENCE: 46

Xaa Lys Xaa Lys
1

<210> SEQ ID NO 47
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: Omega-amino-12 carbon fatty acid
<220> FEATURE:
```

```
<221> NAME/KEY: misc_feature
<222> LOCATION: (3)..(3)
<223> OTHER INFORMATION: Omega-amino-8 carbon fatty acid
<220> FEATURE:
<221> NAME/KEY: misc_feature
<222> LOCATION: (5)..(5)
<223> OTHER INFORMATION: Omega-amino-8 carbon fatty acid

<400> SEQUENCE: 47

Xaa Lys Xaa Lys Xaa Lys
1               5

<210> SEQ ID NO 48
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: Omega-amino-12 carbon fatty acid
<220> FEATURE:
<221> NAME/KEY: misc_feature
<222> LOCATION: (3)..(3)
<223> OTHER INFORMATION: Omega-amino-8 carbon fatty acid
<220> FEATURE:
<221> NAME/KEY: misc_feature
<222> LOCATION: (5)..(5)
<223> OTHER INFORMATION: Omega-amino-8 carbon fatty acid
<220> FEATURE:
<221> NAME/KEY: misc_feature
<222> LOCATION: (7)..(7)
<223> OTHER INFORMATION: Omega-amino-8 carbon fatty acid

<400> SEQUENCE: 48

Xaa Lys Xaa Lys Xaa Lys Xaa Lys
1               5

<210> SEQ ID NO 49
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: Omega-amino-12 carbon fatty acid
<220> FEATURE:
<221> NAME/KEY: misc_feature
<222> LOCATION: (3)..(3)
<223> OTHER INFORMATION: Omega-amino-8 carbon fatty acid
<220> FEATURE:
<221> NAME/KEY: misc_feature
<222> LOCATION: (5)..(5)
<223> OTHER INFORMATION: Omega-amino-8 carbon fatty acid
<220> FEATURE:
<221> NAME/KEY: misc_feature
<222> LOCATION: (7)..(7)
<223> OTHER INFORMATION: Omega-amino-8 carbon fatty acid
<220> FEATURE:
<221> NAME/KEY: misc_feature
<222> LOCATION: (9)..(9)
<223> OTHER INFORMATION: Omega-amino-8 carbon fatty acid

<400> SEQUENCE: 49

Xaa Lys Xaa Lys Xaa Lys Xaa Lys Xaa Lys
```

-continued

```
1               5                   10

<210> SEQ ID NO 50
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: Omega-amino-12 carbon fatty acid
<220> FEATURE:
<221> NAME/KEY: misc_feature
<222> LOCATION: (3)..(3)
<223> OTHER INFORMATION: Omega-amino-8 carbon fatty acid
<220> FEATURE:
<221> NAME/KEY: misc_feature
<222> LOCATION: (5)..(5)
<223> OTHER INFORMATION: Omega-amino-8 carbon fatty acid
<220> FEATURE:
<221> NAME/KEY: misc_feature
<222> LOCATION: (7)..(7)
<223> OTHER INFORMATION: Omega-amino-8 carbon fatty acid
<220> FEATURE:
<221> NAME/KEY: misc_feature
<222> LOCATION: (9)..(9)
<223> OTHER INFORMATION: Omega-amino-8 carbon fatty acid
<220> FEATURE:
<221> NAME/KEY: misc_feature
<222> LOCATION: (11)..(11)
<223> OTHER INFORMATION: Omega-amino-8 carbon fatty acid

<400> SEQUENCE: 50

Xaa Lys Xaa Lys Xaa Lys Xaa Lys Xaa Lys Xaa Lys
1               5                   10

<210> SEQ ID NO 51
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: Omega-amino-12 carbon fatty acid
<220> FEATURE:
<221> NAME/KEY: misc_feature
<222> LOCATION: (3)..(3)
<223> OTHER INFORMATION: Omega-amino-8 carbon fatty acid
<220> FEATURE:
<221> NAME/KEY: misc_feature
<222> LOCATION: (5)..(5)
<223> OTHER INFORMATION: Omega-amino-8 carbon fatty acid
<220> FEATURE:
<221> NAME/KEY: misc_feature
<222> LOCATION: (7)..(7)
<223> OTHER INFORMATION: Omega-amino-8 carbon fatty acid
<220> FEATURE:
<221> NAME/KEY: misc_feature
<222> LOCATION: (9)..(9)
<223> OTHER INFORMATION: Omega-amino-8 carbon fatty acid
<220> FEATURE:
<221> NAME/KEY: misc_feature
<222> LOCATION: (11)..(11)
<223> OTHER INFORMATION: Omega-amino-8 carbon fatty acid
<220> FEATURE:
<221> NAME/KEY: misc_feature
<222> LOCATION: (13)..(13)
```

<223> OTHER INFORMATION: Omega-amino-8 carbon fatty acid

<400> SEQUENCE: 51

Xaa Lys Xaa Lys Xaa Lys Xaa Lys Xaa Lys Xaa Lys Xaa Lys
1               5                   10

<210> SEQ ID NO 52
<211> LENGTH: 16
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: Omega-amino-12 carbon fatty acid
<220> FEATURE:
<221> NAME/KEY: misc_feature
<222> LOCATION: (3)..(3)
<223> OTHER INFORMATION: Omega-amino-8 carbon fatty acid
<220> FEATURE:
<221> NAME/KEY: misc_feature
<222> LOCATION: (5)..(5)
<223> OTHER INFORMATION: Omega-amino-8 carbon fatty acid
<220> FEATURE:
<221> NAME/KEY: misc_feature
<222> LOCATION: (7)..(7)
<223> OTHER INFORMATION: Omega-amino-8 carbon fatty acid
<220> FEATURE:
<221> NAME/KEY: misc_feature
<222> LOCATION: (9)..(9)
<223> OTHER INFORMATION: Omega-amino-8 carbon fatty acid
<220> FEATURE:
<221> NAME/KEY: misc_feature
<222> LOCATION: (11)..(11)
<223> OTHER INFORMATION: Omega-amino-8 carbon fatty acid
<220> FEATURE:
<221> NAME/KEY: misc_feature
<222> LOCATION: (13)..(13)
<223> OTHER INFORMATION: Omega-amino-8 carbon fatty acid
<220> FEATURE:
<221> NAME/KEY: misc_feature
<222> LOCATION: (15)..(15)
<223> OTHER INFORMATION: Omega-amino-8 carbon fatty acid

<400> SEQUENCE: 52

Xaa Lys Xaa Lys Xaa Lys Xaa Lys Xaa Lys Xaa Lys Xaa Lys Xaa Lys
1               5                   10                  15

<210> SEQ ID NO 53
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: N' 12-carbon fatty acid residue conjugated
      lysine
<220> FEATURE:
<221> NAME/KEY: misc_feature
<222> LOCATION: (2)..(2)
<223> OTHER INFORMATION: Omega-amino-8 carbon fatty acid
<220> FEATURE:
<221> NAME/KEY: misc_feature
<222> LOCATION: (3)..(3)
<223> OTHER INFORMATION: Xaa can be any naturally occurring amino acid
<220> FEATURE:

```
<221> NAME/KEY: misc_feature
<222> LOCATION: (4)..(4)
<223> OTHER INFORMATION: Omega-amino-8 carbon fatty acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Omega-amino-8 carbon fatty acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Omega-amino-8 carbon fatty acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 53

Lys Lys Xaa Lys Xaa Lys Xaa Lys Xaa Lys
1               5                   10

<210> SEQ ID NO 54
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: N' 12-carbon fatty acid residue conjugated
      lysine
<220> FEATURE:
<221> NAME/KEY: misc_feature
<222> LOCATION: (2)..(2)
<223> OTHER INFORMATION: Omega-amino-12 carbon fatty acid

<400> SEQUENCE: 54

Lys Xaa Lys
1

<210> SEQ ID NO 55
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: N' 12-carbon fatty acid residue conjugated
      lysine
<220> FEATURE:
<221> NAME/KEY: misc_feature
<222> LOCATION: (2)..(2)
<223> OTHER INFORMATION: Omega-amino-12 carbon fatty acid
<220> FEATURE:
<221> NAME/KEY: misc_feature
<222> LOCATION: (4)..(4)
<223> OTHER INFORMATION: Omega-amino-12 carbon fatty acid

<400> SEQUENCE: 55
```

-continued

Lys Xaa Lys Xaa Lys
1               5

<210> SEQ ID NO 56
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: N' 12-carbon fatty acid residue conjugated
      lysine
<220> FEATURE:
<221> NAME/KEY: misc_feature
<222> LOCATION: (2)..(2)
<223> OTHER INFORMATION: Omega-amino-12 carbon fatty acid
<220> FEATURE:
<221> NAME/KEY: misc_feature
<222> LOCATION: (4)..(4)
<223> OTHER INFORMATION: Omega-amino-12 carbon fatty acid
<220> FEATURE:
<221> NAME/KEY: misc_feature
<222> LOCATION: (6)..(6)
<223> OTHER INFORMATION: Omega-amino-12 carbon fatty acid

<400> SEQUENCE: 56

Lys Xaa Lys Xaa Lys Xaa Lys
1               5

<210> SEQ ID NO 57
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: N' 12-carbon fatty acid residue conjugated
      lysine
<220> FEATURE:
<221> NAME/KEY: misc_feature
<222> LOCATION: (2)..(2)
<223> OTHER INFORMATION: Omega-amino-12 carbon fatty acid
<220> FEATURE:
<221> NAME/KEY: misc_feature
<222> LOCATION: (4)..(4)
<223> OTHER INFORMATION: Omega-amino-12 carbon fatty acid
<220> FEATURE:
<221> NAME/KEY: misc_feature
<222> LOCATION: (6)..(6)
<223> OTHER INFORMATION: Omega-amino-12 carbon fatty acid
<220> FEATURE:
<221> NAME/KEY: misc_feature
<222> LOCATION: (8)..(8)
<223> OTHER INFORMATION: Omega-amino-12 carbon fatty acid

<400> SEQUENCE: 57

Lys Xaa Lys Xaa Lys Xaa Lys Xaa Lys
1               5

<210> SEQ ID NO 58
<211> LENGTH: 3
<212> TYPE: PRT
<213> ORGANISM: Artificial sequence

```
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (2)..(2)
<223> OTHER INFORMATION: Omega-amino-12 carbon fatty acid

<400> SEQUENCE: 58

Lys Xaa Lys
1

<210> SEQ ID NO 59
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (2)..(2)
<223> OTHER INFORMATION: Omega-amino-12 carbon fatty acid
<220> FEATURE:
<221> NAME/KEY: misc_feature
<222> LOCATION: (4)..(4)
<223> OTHER INFORMATION: Omega-amino-12 carbon fatty acid

<400> SEQUENCE: 59

Lys Xaa Lys Xaa Lys
1               5

<210> SEQ ID NO 60
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (2)..(2)
<223> OTHER INFORMATION: Omega-amino-12 carbon fatty acid
<220> FEATURE:
<221> NAME/KEY: misc_feature
<222> LOCATION: (4)..(4)
<223> OTHER INFORMATION: Omega-amino-12 carbon fatty acid
<220> FEATURE:
<221> NAME/KEY: misc_feature
<222> LOCATION: (6)..(6)
<223> OTHER INFORMATION: Omega-amino-12 carbon fatty acid

<400> SEQUENCE: 60

Lys Xaa Lys Xaa Lys Xaa Lys
1               5

<210> SEQ ID NO 61
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
```

```
<222> LOCATION: (2)..(2)
<223> OTHER INFORMATION: Omega-amino-12 carbon fatty acid
<220> FEATURE:
<221> NAME/KEY: misc_feature
<222> LOCATION: (4)..(4)
<223> OTHER INFORMATION: Omega-amino-12 carbon fatty acid
<220> FEATURE:
<221> NAME/KEY: misc_feature
<222> LOCATION: (6)..(6)
<223> OTHER INFORMATION: Omega-amino-12 carbon fatty acid
<220> FEATURE:
<221> NAME/KEY: misc_feature
<222> LOCATION: (8)..(8)
<223> OTHER INFORMATION: Omega-amino-12 carbon fatty acid

<400> SEQUENCE: 61

Lys Xaa Lys Xaa Lys Xaa Lys Xaa Lys
1               5

<210> SEQ ID NO 62
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (2)..(2)
<223> OTHER INFORMATION: Omega-amino-12 carbon fatty acid
<220> FEATURE:
<221> NAME/KEY: misc_feature
<222> LOCATION: (4)..(4)
<223> OTHER INFORMATION: Omega-amino-12 carbon fatty acid
<220> FEATURE:
<221> NAME/KEY: misc_feature
<222> LOCATION: (6)..(6)
<223> OTHER INFORMATION: Omega-amino-12 carbon fatty acid
<220> FEATURE:
<221> NAME/KEY: misc_feature
<222> LOCATION: (8)..(8)
<223> OTHER INFORMATION: Omega-amino-12 carbon fatty acid
<220> FEATURE:
<221> NAME/KEY: misc_feature
<222> LOCATION: (10)..(10)
<223> OTHER INFORMATION: Omega-amino-12 carbon fatty acid

<400> SEQUENCE: 62

Lys Xaa Lys Xaa Lys Xaa Lys Xaa Lys Xaa Lys
1               5                   10

<210> SEQ ID NO 63
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (2)..(2)
<223> OTHER INFORMATION: Omega-amino-12 carbon fatty acid
<220> FEATURE:
<221> NAME/KEY: misc_feature
<222> LOCATION: (4)..(4)
<223> OTHER INFORMATION: Omega-amino-12 carbon fatty acid
<220> FEATURE:
<221> NAME/KEY: misc_feature
<222> LOCATION: (6)..(6)
<223> OTHER INFORMATION: Omega-amino-12 carbon fatty acid
<220> FEATURE:
```

<221> NAME/KEY: misc_feature
<222> LOCATION: (8)..(8)
<223> OTHER INFORMATION: Omega-amino-12 carbon fatty acid
<220> FEATURE:
<221> NAME/KEY: misc_feature
<222> LOCATION: (10)..(10)
<223> OTHER INFORMATION: Omega-amino-12 carbon fatty acid
<220> FEATURE:
<221> NAME/KEY: misc_feature
<222> LOCATION: (12)..(12)
<223> OTHER INFORMATION: Omega-amino-12 carbon fatty acid

<400> SEQUENCE: 63

Lys Xaa Lys Xaa Lys Xaa Lys Xaa Lys Xaa Lys Xaa Lys
1               5                   10

<210> SEQ ID NO 64
<211> LENGTH: 15
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (2)..(2)
<223> OTHER INFORMATION: Omega-amino-12 carbon fatty acid
<220> FEATURE:
<221> NAME/KEY: misc_feature
<222> LOCATION: (4)..(4)
<223> OTHER INFORMATION: Omega-amino-12 carbon fatty acid
<220> FEATURE:
<221> NAME/KEY: misc_feature
<222> LOCATION: (6)..(6)
<223> OTHER INFORMATION: Omega-amino-12 carbon fatty acid
<220> FEATURE:
<221> NAME/KEY: misc_feature
<222> LOCATION: (8)..(8)
<223> OTHER INFORMATION: Omega-amino-12 carbon fatty acid
<220> FEATURE:
<221> NAME/KEY: misc_feature
<222> LOCATION: (10)..(10)
<223> OTHER INFORMATION: Omega-amino-12 carbon fatty acid
<220> FEATURE:
<221> NAME/KEY: misc_feature
<222> LOCATION: (12)..(12)
<223> OTHER INFORMATION: Omega-amino-12 carbon fatty acid
<220> FEATURE:
<221> NAME/KEY: misc_feature
<222> LOCATION: (14)..(14)
<223> OTHER INFORMATION: Omega-amino-12 carbon fatty acid

<400> SEQUENCE: 64

Lys Xaa Lys Xaa Lys Xaa Lys Xaa Lys Xaa Lys Xaa Lys Xaa Lys
1               5                   10                  15

<210> SEQ ID NO 65
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: Omega-amino-12 carbon fatty acid
<220> FEATURE:
<221> NAME/KEY: misc_feature
<222> LOCATION: (3)..(3)
<223> OTHER INFORMATION: Omega-amino-12 carbon fatty acid

```
<400> SEQUENCE: 65

Xaa Lys Xaa Lys
1

<210> SEQ ID NO 66
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: Omega-amino-12 carbon fatty acid
<220> FEATURE:
<221> NAME/KEY: misc_feature
<222> LOCATION: (3)..(3)
<223> OTHER INFORMATION: Omega-amino-12 carbon fatty acid
<220> FEATURE:
<221> NAME/KEY: misc_feature
<222> LOCATION: (5)..(5)
<223> OTHER INFORMATION: Omega-amino-12 carbon fatty acid

<400> SEQUENCE: 66

Xaa Lys Xaa Lys Xaa Lys
1               5

<210> SEQ ID NO 67
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: Omega-amino-12 carbon fatty acid
<220> FEATURE:
<221> NAME/KEY: misc_feature
<222> LOCATION: (3)..(3)
<223> OTHER INFORMATION: Omega-amino-12 carbon fatty acid
<220> FEATURE:
<221> NAME/KEY: misc_feature
<222> LOCATION: (5)..(5)
<223> OTHER INFORMATION: Omega-amino-12 carbon fatty acid
<220> FEATURE:
<221> NAME/KEY: misc_feature
<222> LOCATION: (7)..(7)
<223> OTHER INFORMATION: Omega-amino-12 carbon fatty acid

<400> SEQUENCE: 67

Xaa Lys Xaa Lys Xaa Lys Xaa Lys
1               5

<210> SEQ ID NO 68
<211> LENGTH: 10
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
```

```
<223> OTHER INFORMATION: Omega-amino-12 carbon fatty acid
<220> FEATURE:
<221> NAME/KEY: misc_feature
<222> LOCATION: (3)..(3)
<223> OTHER INFORMATION: Omega-amino-12 carbon fatty acid
<220> FEATURE:
<221> NAME/KEY: misc_feature
<222> LOCATION: (5)..(5)
<223> OTHER INFORMATION: Omega-amino-12 carbon fatty acid
<220> FEATURE:
<221> NAME/KEY: misc_feature
<222> LOCATION: (7)..(7)
<223> OTHER INFORMATION: Omega-amino-12 carbon fatty acid
<220> FEATURE:
<221> NAME/KEY: misc_feature
<222> LOCATION: (9)..(9)
<223> OTHER INFORMATION: Omega-amino-12 carbon fatty acid

<400> SEQUENCE: 68

Xaa Lys Xaa Lys Xaa Lys Xaa Lys Xaa Lys
1               5                   10

<210> SEQ ID NO 69
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: Omega-amino-12 carbon fatty acid
<220> FEATURE:
<221> NAME/KEY: misc_feature
<222> LOCATION: (3)..(3)
<223> OTHER INFORMATION: Omega-amino-12 carbon fatty acid
<220> FEATURE:
<221> NAME/KEY: misc_feature
<222> LOCATION: (5)..(5)
<223> OTHER INFORMATION: Omega-amino-12 carbon fatty acid
<220> FEATURE:
<221> NAME/KEY: misc_feature
<222> LOCATION: (7)..(7)
<223> OTHER INFORMATION: Omega-amino-12 carbon fatty acid
<220> FEATURE:
<221> NAME/KEY: misc_feature
<222> LOCATION: (9)..(9)
<223> OTHER INFORMATION: Omega-amino-12 carbon fatty acid
<220> FEATURE:
<221> NAME/KEY: misc_feature
<222> LOCATION: (11)..(11)
<223> OTHER INFORMATION: Omega-amino-12 carbon fatty acid

<400> SEQUENCE: 69

Xaa Lys Xaa Lys Xaa Lys Xaa Lys Xaa Lys Xaa Lys
1               5                   10

<210> SEQ ID NO 70
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: Omega-amino-12 carbon fatty acid
<220> FEATURE:
<221> NAME/KEY: misc_feature
```

```
<222> LOCATION: (3)..(3)
<223> OTHER INFORMATION: Omega-amino-12 carbon fatty acid
<220> FEATURE:
<221> NAME/KEY: misc_feature
<222> LOCATION: (5)..(5)
<223> OTHER INFORMATION: Omega-amino-12 carbon fatty acid
<220> FEATURE:
<221> NAME/KEY: misc_feature
<222> LOCATION: (7)..(7)
<223> OTHER INFORMATION: Omega-amino-12 carbon fatty acid
<220> FEATURE:
<221> NAME/KEY: misc_feature
<222> LOCATION: (9)..(9)
<223> OTHER INFORMATION: Omega-amino-12 carbon fatty acid
<220> FEATURE:
<221> NAME/KEY: misc_feature
<222> LOCATION: (11)..(11)
<223> OTHER INFORMATION: Omega-amino-12 carbon fatty acid
<220> FEATURE:
<221> NAME/KEY: misc_feature
<222> LOCATION: (13)..(13)
<223> OTHER INFORMATION: Omega-amino-12 carbon fatty acid

<400> SEQUENCE: 70

Xaa Lys Xaa Lys Xaa Lys Xaa Lys Xaa Lys Xaa Lys Xaa Lys
1               5                   10

<210> SEQ ID NO 71
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: Omega-amino-12 carbon fatty acid
<220> FEATURE:
<221> NAME/KEY: misc_feature
<222> LOCATION: (3)..(3)
<223> OTHER INFORMATION: Omega-amino-12 carbon fatty acid
<220> FEATURE:
<221> NAME/KEY: misc_feature
<222> LOCATION: (5)..(5)
<223> OTHER INFORMATION: Omega-amino-12 carbon fatty acid
<220> FEATURE:
<221> NAME/KEY: misc_feature
<222> LOCATION: (7)..(7)
<223> OTHER INFORMATION: Omega-amino-12 carbon fatty acid
<220> FEATURE:
<221> NAME/KEY: misc_feature
<222> LOCATION: (9)..(9)
<223> OTHER INFORMATION: Omega-amino-12 carbon fatty acid
<220> FEATURE:
<221> NAME/KEY: misc_feature
<222> LOCATION: (11)..(11)
<223> OTHER INFORMATION: Omega-amino-12 carbon fatty acid
<220> FEATURE:
<221> NAME/KEY: misc_feature
<222> LOCATION: (13)..(13)
<223> OTHER INFORMATION: Omega-amino-12 carbon fatty acid
<220> FEATURE:
<221> NAME/KEY: misc_feature
<222> LOCATION: (15)..(15)
<223> OTHER INFORMATION: Omega-amino-12 carbon fatty acid

<400> SEQUENCE: 71

Xaa Lys Xaa Lys Xaa Lys Xaa Lys Xaa Lys Xaa Lys Xaa Lys
1               5                   10

<210> SEQ ID NO 72
<211> LENGTH: 4
```

```
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (3)..(3)
<223> OTHER INFORMATION: Omega-amino-12 carbon fatty acid

<400> SEQUENCE: 72

Lys Lys Xaa Lys
1

<210> SEQ ID NO 73
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (2)..(2)
<223> OTHER INFORMATION: Omega-amino-12 carbon fatty acid
<220> FEATURE:
<221> NAME/KEY: misc_feature
<222> LOCATION: (5)..(5)
<223> OTHER INFORMATION: Omega-amino-12 carbon fatty acid

<400> SEQUENCE: 73

Lys Xaa Lys Lys Xaa Lys
1               5

<210> SEQ ID NO 74
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (3)..(3)
<223> OTHER INFORMATION: Omega-amino-12 carbon fatty acid
<220> FEATURE:
<221> NAME/KEY: misc_feature
<222> LOCATION: (6)..(6)
<223> OTHER INFORMATION: Omega-amino-12 carbon fatty acid

<400> SEQUENCE: 74

Lys Lys Xaa Lys Lys Xaa Lys
1               5

<210> SEQ ID NO 75
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: N' 8-carbon fatty acid residue conjugated
```

```
            lysine
<220> FEATURE:
<221> NAME/KEY: misc_feature
<222> LOCATION: (3)..(3)
<223> OTHER INFORMATION: Omega-amino-12 carbon fatty acid

<400> SEQUENCE: 75

Lys Lys Xaa Lys
1

<210> SEQ ID NO 76
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: N' 8-carbon fatty acid residue conjugated
      lysine
<220> FEATURE:
<221> NAME/KEY: misc_feature
<222> LOCATION: (2)..(2)
<223> OTHER INFORMATION: Omega-amino-12 carbon fatty acid
<220> FEATURE:
<221> NAME/KEY: misc_feature
<222> LOCATION: (5)..(5)
<223> OTHER INFORMATION: Omega-amino-12 carbon fatty acid

<400> SEQUENCE: 76

Lys Xaa Lys Lys Xaa Lys
1               5

<210> SEQ ID NO 77
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: N' 8-carbon fatty acid residue conjugated
      lysine
<220> FEATURE:
<221> NAME/KEY: misc_feature
<222> LOCATION: (3)..(3)
<223> OTHER INFORMATION: Omega-amino-12 carbon fatty acid
<220> FEATURE:
<221> NAME/KEY: misc_feature
<222> LOCATION: (6)..(6)
<223> OTHER INFORMATION: Omega-amino-12 carbon fatty acid

<400> SEQUENCE: 77

Lys Lys Xaa Lys Lys Xaa Lys
1               5

<210> SEQ ID NO 78
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
```

```
<220> FEATURE:
<221> NAME/KEY: misc_feature
<222> LOCATION: (1)..(1)
<223> OTHER INFORMATION: N' 12-carbon fatty acid residue conjugated
      lysine
<220> FEATURE:
<221> NAME/KEY: misc_feature
<222> LOCATION: (3)..(3)
<223> OTHER INFORMATION: Omega-amino-12 carbon fatty acid

<400> SEQUENCE: 78

Lys Lys Xaa Lys
1

<210> SEQ ID NO 79
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: N' 12-carbon fatty acid residue conjugated
      lysine
<220> FEATURE:
<221> NAME/KEY: misc_feature
<222> LOCATION: (2)..(2)
<223> OTHER INFORMATION: Omega-amino-12 carbon fatty acid
<220> FEATURE:
<221> NAME/KEY: misc_feature
<222> LOCATION: (5)..(5)
<223> OTHER INFORMATION: Omega-amino-12 carbon fatty acid

<400> SEQUENCE: 79

Lys Xaa Lys Lys Xaa Lys
1               5

<210> SEQ ID NO 80
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: N' 12-carbon fatty acid residue conjugated
      lysine
<220> FEATURE:
<221> NAME/KEY: misc_feature
<222> LOCATION: (3)..(3)
<223> OTHER INFORMATION: Omega-amino-12 carbon fatty acid
<220> FEATURE:
<221> NAME/KEY: misc_feature
<222> LOCATION: (6)..(6)
<223> OTHER INFORMATION: Omega-amino-12 carbon fatty acid

<400> SEQUENCE: 80

Lys Lys Xaa Lys Lys Xaa Lys
1               5

<210> SEQ ID NO 81
<211> LENGTH: 5
<212> TYPE: PRT
<213> ORGANISM: Artificial sequence
<220> FEATURE:
```

<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: Omega-amino-12 carbon fatty acid
<220> FEATURE:
<221> NAME/KEY: misc_feature
<222> LOCATION: (4)..(4)
<223> OTHER INFORMATION: Omega-amino-12 carbon fatty acid

<400> SEQUENCE: 81

Xaa Lys Lys Xaa Lys
1               5

<210> SEQ ID NO 82
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: Omega-amino-12 carbon fatty acid
<220> FEATURE:
<221> NAME/KEY: misc_feature
<222> LOCATION: (3)..(3)
<223> OTHER INFORMATION: Omega-amino-12 carbon fatty acid
<220> FEATURE:
<221> NAME/KEY: misc_feature
<222> LOCATION: (6)..(6)
<223> OTHER INFORMATION: Omega-amino-12 carbon fatty acid

<400> SEQUENCE: 82

Xaa Lys Xaa Lys Lys Xaa Lys
1               5

<210> SEQ ID NO 83
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: Omega-amino-12 carbon fatty acid
<220> FEATURE:
<221> NAME/KEY: misc_feature
<222> LOCATION: (4)..(4)
<223> OTHER INFORMATION: Omega-amino-12 carbon fatty acid
<220> FEATURE:
<221> NAME/KEY: misc_feature
<222> LOCATION: (7)..(7)
<223> OTHER INFORMATION: Omega-amino-12 carbon fatty acid

<400> SEQUENCE: 83

Xaa Lys Lys Xaa Lys Lys Xaa Lys
1               5

<210> SEQ ID NO 84
<211> LENGTH: 3
<212> TYPE: PRT
<213> ORGANISM: Artificial sequence

```
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: N' 12-carbon fatty acid residue conjugated
      Ornithine
<220> FEATURE:
<221> NAME/KEY: misc_feature
<222> LOCATION: (2)..(2)
<223> OTHER INFORMATION: Omega-amino-12 carbon fatty acid
<220> FEATURE:
<221> NAME/KEY: misc_feature
<222> LOCATION: (3)..(3)
<223> OTHER INFORMATION: Ornithine

<400> SEQUENCE: 84

Xaa Xaa Xaa
1

<210> SEQ ID NO 85
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: C' amidated peptide
<220> FEATURE:
<221> NAME/KEY: misc_feature
<222> LOCATION: (1)..(1)
<223> OTHER INFORMATION: N' 12-carbon fatty acid residue conjugated
      Arginine
<220> FEATURE:
<221> NAME/KEY: misc_feature
<222> LOCATION: (2)..(2)
<223> OTHER INFORMATION: Omega-amino-12 carbon fatty acid

<400> SEQUENCE: 85

Arg Xaa Arg
1

<210> SEQ ID NO 86
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: N' 12-carbon fatty acid residue conjugated
      lysine
<220> FEATURE:
<221> NAME/KEY: misc_feature
<222> LOCATION: (2)..(2)
<223> OTHER INFORMATION: Omega-amino-12 carbon fatty acid

<400> SEQUENCE: 86

Lys Xaa Lys
1

<210> SEQ ID NO 87
<211> LENGTH: 5
<212> TYPE: PRT
<213> ORGANISM: Artificial sequence
<220> FEATURE:
<223> OTHER INFORMATION: Synthetic peptide
<220> FEATURE:
```

```
<221> NAME/KEY: misc_feature
<222> LOCATION: (1)..(1)
<223> OTHER INFORMATION: N' 12-carbon fatty acid residue conjugated
      lysine
<220> FEATURE:
<221> NAME/KEY: misc_feature
<222> LOCATION: (2)..(2)
<223> OTHER INFORMATION: Omega-amino-12 carbon fatty acid
<220> FEATURE:
<221> NAME/KEY: misc_feature
<222> LOCATION: (4)..(4)
<223> OTHER INFORMATION: Omega-amino-12 carbon fatty acid

<400> SEQUENCE: 87

Lys Xaa Lys Xaa Lys
1               5

<210> SEQ ID NO 88
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: N' 12-carbon fatty acid residue conjugated
      lysine
<220> FEATURE:
<221> NAME/KEY: misc_feature
<222> LOCATION: (2)..(2)
<223> OTHER INFORMATION: Omega-amino-12 carbon fatty acid
<220> FEATURE:
<221> NAME/KEY: misc_feature
<222> LOCATION: (4)..(4)
<223> OTHER INFORMATION: Omega-amino-12 carbon fatty acid
<220> FEATURE:
<221> NAME/KEY: misc_feature
<222> LOCATION: (6)..(6)
<223> OTHER INFORMATION: Omega-amino-12 carbon fatty acid

<400> SEQUENCE: 88

Lys Xaa Lys Xaa Lys Xaa Lys
1               5

<210> SEQ ID NO 89
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Omega-amino-12 carbon fatty acid

<400> SEQUENCE: 89

Lys Xaa Lys
1

<210> SEQ ID NO 90
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Omega-amino-12 carbon fatty acid
<220> FEATURE:
<221> NAME/KEY: misc_feature
<222> LOCATION: (4)..(4)
```

```
<223> OTHER INFORMATION: Omega-amino-12 carbon fatty acid

<400> SEQUENCE: 90

Lys Xaa Lys Xaa Lys
1               5

<210> SEQ ID NO 91
<211> LENGTH: 7
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Omega-amino-12 carbon fatty acid
<220> FEATURE:
<221> NAME/KEY: misc_feature
<222> LOCATION: (4)..(4)
<223> OTHER INFORMATION: Omega-amino-12 carbon fatty acid
<220> FEATURE:
<221> NAME/KEY: misc_feature
<222> LOCATION: (6)..(6)
<223> OTHER INFORMATION: Omega-amino-12 carbon fatty acid

<400> SEQUENCE: 91

Lys Xaa Lys Xaa Lys Xaa Lys
1               5

<210> SEQ ID NO 92
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Omega-amino-12 carbon fatty acid
<220> FEATURE:
<221> NAME/KEY: misc_feature
<222> LOCATION: (3)..(3)
<223> OTHER INFORMATION: Omega-amino-12 carbon fatty acid

<400> SEQUENCE: 92

Xaa Lys Xaa Lys
1

<210> SEQ ID NO 93
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Omega-amino-12 carbon fatty acid
<220> FEATURE:
<221> NAME/KEY: misc_feature
<222> LOCATION: (3)..(3)
<223> OTHER INFORMATION: Omega-amino-12 carbon fatty acid
<220> FEATURE:
<221> NAME/KEY: misc_feature
<222> LOCATION: (5)..(5)
<223> OTHER INFORMATION: Omega-amino-12 carbon fatty acid

<400> SEQUENCE: 93

Xaa Lys Xaa Lys Xaa Lys
1               5
```

<210> SEQ ID NO 94
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Omega-amino-12 carbon fatty acid
<220> FEATURE:
<221> NAME/KEY: misc_feature
<222> LOCATION: (3)..(3)
<223> OTHER INFORMATION: Omega-amino-12 carbon fatty acid
<220> FEATURE:
<221> NAME/KEY: misc_feature
<222> LOCATION: (5)..(5)
<223> OTHER INFORMATION: Omega-amino-12 carbon fatty acid
<220> FEATURE:
<221> NAME/KEY: misc_feature
<222> LOCATION: (7)..(7)
<223> OTHER INFORMATION: Omega-amino-12 carbon fatty acid

<400> SEQUENCE: 94

Xaa Lys Xaa Lys Xaa Lys Xaa Lys
1               5

<210> SEQ ID NO 95
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Fmoc conjugated lysine
<220> FEATURE:
<221> NAME/KEY: misc_feature
<222> LOCATION: (2)..(2)
<223> OTHER INFORMATION: Omega-amino-12 carbon fatty acid
<220> FEATURE:
<221> NAME/KEY: misc_feature
<222> LOCATION: (4)..(4)
<223> OTHER INFORMATION: Omega-amino-12 carbon fatty acid

<400> SEQUENCE: 95

Lys Xaa Lys Xaa Lys
1               5

<210> SEQ ID NO 96
<211> LENGTH: 17
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<223> OTHER INFORMATION: IB-367 peptide

<400> SEQUENCE: 96

Arg Gly Gly Leu Cys Tyr Cys Arg Gly Arg Phe Cys Val Cys Val Gly
1               5                   10                  15

Arg

<210> SEQ ID NO 97
<211> LENGTH: 15
<212> TYPE: PRT
<213> ORGANISM: Artificial sequence
<220> FEATURE:
<223> OTHER INFORMATION: Synthetic peptide
<220> FEATURE:

-continued

```
<221> NAME/KEY: misc_feature
<222> LOCATION: (4)..(4)
<223> OTHER INFORMATION: Omega-amino-12 carbon fatty acid

<400> SEQUENCE: 97

Ala Leu Trp Xaa Lys Thr Leu Leu Lys Lys Val Leu Lys Ala Ala
1               5                   10                  15

<210> SEQ ID NO 98
<211> LENGTH: 16
<212> TYPE: PRT
<213> ORGANISM: Artificial sequence
<220> FEATURE:
<223> OTHER INFORMATION: Synthetic peptide

<400> SEQUENCE: 98

Ala Leu Trp Met Thr Leu Leu Lys Lys Val Leu Lys Ala Ala Ala Lys
1               5                   10                  15

<210> SEQ ID NO 99
<211> LENGTH: 8
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: N' 8-carbon fatty acid residue conjugated
      lysine

<400> SEQUENCE: 99

Lys Lys Lys Lys Lys Lys Lys Lys
1               5
```